(12) United States Patent
Kim et al.

(10) Patent No.: US 10,333,071 B2
(45) Date of Patent: Jun. 25, 2019

(54) ORGANIC LIGHT EMITTING DEVICE

(71) Applicants: Samsung Display Co., Ltd., Yongin-si, Gyeonggi-do (KR); SEOUL NATIONAL UNIVERSITY R&DB FOUNDATION, Seoul (KR)

(72) Inventors: Sehun Kim, Yongin-si (KR); Jongin Hong, Seoul (KR); Seongjin Jeong, Seoul (KR); Samil Kho, Yongin-si (KR); Hyoungkun Kim, Yongin-si (KR); Hyein Jeong, Yongin-si (KR)

(73) Assignees: Samsung Display Co., Ltd., Yongin-si (KR); Seoul National University R&DB Foundation, Seoul (KR)

( * ) Notice: Subject to any disclaimer, the term of this patent is extended or adjusted under 35 U.S.C. 154(b) by 181 days.

(21) Appl. No.: 15/228,818

(22) Filed: Aug. 4, 2016

(65) Prior Publication Data

US 2017/0117478 A1    Apr. 27, 2017

(30) Foreign Application Priority Data

Oct. 27, 2015  (KR) .......................... 10-2015-0149739

(51) Int. Cl.
*H01L 51/54* (2006.01)
*C09K 11/06* (2006.01)
(Continued)

(52) U.S. Cl.
CPC ........ *H01L 51/0052* (2013.01); *C07D 215/14* (2013.01); *C07D 471/04* (2013.01); *C09K 11/025* (2013.01); *C09K 11/06* (2013.01); *H01L 51/0058* (2013.01); *H01L 51/0072* (2013.01); *C09K 2211/1007* (2013.01);
(Continued)

(58) Field of Classification Search
CPC ............ C09K 2211/00; C09K 2211/10; C09K 2211/1007; C09K 2211/1011; C09K 2211/1029; C09K 2211/1044; C09K 11/025; C09K 11/06; C07D 215/12; C07D 215/14; C07D 471/00; C07D 471/02; C07D 471/04; H01L 51/0032; H01L 51/005; H01L 51/0051; H01L 51/0052; H01L 51/0059; H01L 51/0058; H01L 51/0062; H01L 51/0071; H01L 51/0072; H01L 51/50; H01L 51/5012; H01L 51/5024; H01L 51/5056; H01L 51/5072;
(Continued)

(56) References Cited

U.S. PATENT DOCUMENTS 5,635,308 A     6/1997  Inoue et al.
5,759,444 A *   6/1998  Enokida ................ C07C 211/61
                                                       252/301.16
(Continued)

FOREIGN PATENT DOCUMENTS

JP      07-138561 A    5/1995
JP       8-12600 A     1/1996
(Continued)

OTHER PUBLICATIONS

Haykir et al. Thin Solid Films 2013, 548, 171-177. (Year: 2013).*
Tang, C. W. et al.; "Organic electroluminescent diodes"; Appl. Phys. Lett.; vol. 51; Sep. 21, 1987; pp. 913-915.

*Primary Examiner* — Andrew K Bohaty
(74) *Attorney, Agent, or Firm* — Lewis Roca Rothgerber Christie LLP

(57) ABSTRACT

An organic light-emitting device having high efficiency and long lifespan including: a first electrode; a second electrode facing the first electrode; and an organic layer between the first electrode and the second electrode and including an emission layer, wherein the organic layer includes a first compound represented by Formula 1 and a second compound represented by Formula 2:

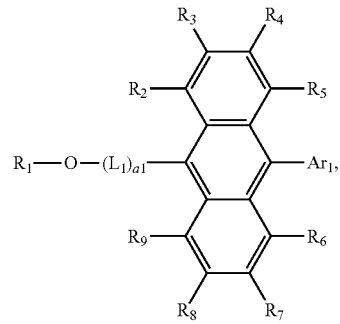

Formula 1

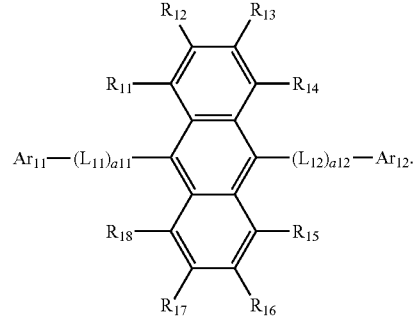

Formula 2

When compounds represented by Formulae 1 and 2 are included in the emission layer, organic light-emitting (Continued)

devices may exhibit improved driving voltage, improved luminance, improved efficiency, and/or improved lifespans.

19 Claims, 7 Drawing Sheets

(51) Int. Cl.
| | |
|---|---|
| *H01L 51/00* | (2006.01) |
| *C09K 11/02* | (2006.01) |
| *C07D 215/14* | (2006.01) |
| *C07D 471/04* | (2006.01) |
| *H01L 51/52* | (2006.01) |
| *H01L 51/50* | (2006.01) |

(52) U.S. Cl.
CPC ............. *C09K 2211/1011* (2013.01); *C09K 2211/1029* (2013.01); *C09K 2211/1044* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01); *H01L 2251/558* (2013.01)

(58) Field of Classification Search
CPC ........... H01L 51/5088; H01L 51/5092; H01L 51/5096; H01L 2251/558
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | |
|---|---|---|---|
| 2004/0161633 A1* | 8/2004 | Seo .................... | H01L 51/0052 428/690 |
| 2005/0064233 A1 | 3/2005 | Matsuura et al. | |
| 2006/0159957 A1* | 7/2006 | Yabunouchi ......... | C07C 211/54 428/690 |
| 2006/0222886 A1* | 10/2006 | Kwong ................. | C09K 11/06 428/690 |
| 2007/0122656 A1* | 5/2007 | Klubek ............... | H01L 51/0052 428/690 |
| 2009/0146139 A1 | 6/2009 | Stoessel et al. | |
| 2010/0327270 A1 | 12/2010 | Buesing et al. | |

FOREIGN PATENT DOCUMENTS

| | | |
|---|---|---|
| JP | 8-239655 A | 9/1996 |
| KR | 10-2005-0019907 A | 3/2005 |
| KR | 10-2008-0114812 A | 12/2008 |
| KR | 10-2009-0111355 A | 10/2009 |
| KR | 10-2010-0094413 A | 8/2010 |
| KR | 10-2010-0110895 A | 10/2010 |
| KR | 10-2011-0123701 A | 11/2011 |
| KR | 10-2012-0117675 A | 10/2012 |
| KR | 10-2015-0001966 A | 1/2015 |
| KR | 10-2015-0043020 A | 4/2015 |

* cited by examiner

ORGANIC LIGHT EMITTING DEVICE

CROSS-REFERENCE TO RELATED APPLICATION

This application claims priority to and the benefit of Korean Patent Application No. 10-2015-0149739, filed on Oct. 27, 2015, in the Korean Intellectual Property Office, the entire content of which is incorporated herein by reference.

BACKGROUND

1. Field

One or more aspects of example embodiments of the present disclosure are related to an organic light-emitting device.

2. Description of the Related Art

Organic light emitting devices are self-emission devices that may have wide viewing angles, high contrast ratios, short response times, and/or excellent brightness, driving voltage, and/or response speed characteristics compared to devices in the related art, and may produce full-color images.

An example organic light-emitting device may include a first electrode on a substrate, and a hole transport region, an emission layer, an electron transport region, and a second electrode sequentially positioned on the first electrode. Holes provided from the first electrode may move toward the emission layer through the hole transport region, and electrons provided from the second electrode may move toward the emission layer through the electron transport region. Carriers (such as holes and electrons) may recombine in the emission layer to produce excitons. These excitons may change (e.g., transition or radiatively decay) from an excited state to the ground state to thereby generate light.

SUMMARY

One or more aspects of example embodiments of the present disclosure are directed toward an organic light-emitting device having high efficiency and a long lifespan.

Additional aspects will be set forth in part in the description which follows and, in part, will be apparent from the description, or may be learned by practice of the presented embodiments.

One or more example embodiments of the present disclosure provide an organic light-emitting device including:

a first electrode;

a second electrode facing the first electrode; and an organic layer between the first electrode and the second electrode and including an emission layer, wherein the organic layer includes a first compound represented by Formula 1 and a second compound represented by Formula 2:

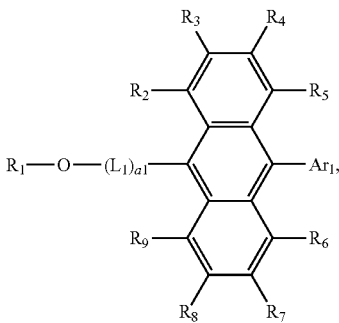

Formula 1

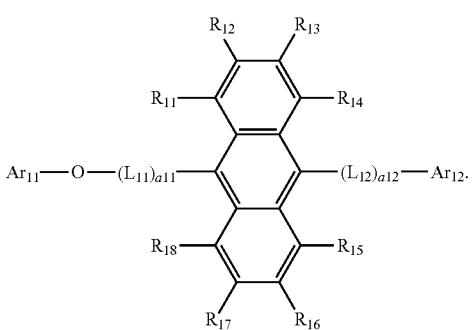

Formula 2

In Formulae 1 and 2, $L_1$, $L_{11}$, and $L_{12}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1, a11, and a12 may each independently be an integer selected from 0 to 5. When a1 is 2 or more, a plurality of $L_1$ groups may be identical to or different from each other, when a11 is 2 or more, a plurality of $L_{11}$ groups may be identical to or different from each other, and when a12 is 2 or more, a plurality of $L_{12}$ groups may be identical to or different from each other, $Ar_1$ may be a substituted or unsubstituted electron transport group, $Ar_{11}$ and $Ar_{12}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_1$ may be selected from the group consisting of:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{60}$ alkyl group; and a $C_1$-$C_{60}$ alkyl group substituted with at least one selected from deuterium, —F, —Cl, —Br, —I, a hydroxyl group, a cyano group, a nitro group, a carboxylic acid group or a salt thereof, a sulfonic acid group or a salt thereof, and a phosphoric acid group or a salt thereof, $R_2$ to $R_9$ and $R_{11}$ to $R_{18}$ may each independently be selected from:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), and at least one substituent of the substituted electron transport group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

BRIEF DESCRIPTION OF THE DRAWINGS

These and/or other aspects will become apparent and more readily appreciated from the following descriptions of example embodiments, taken in conjunction with the accompanying drawings in which.

DETAILED DESCRIPTION

Figure 1:
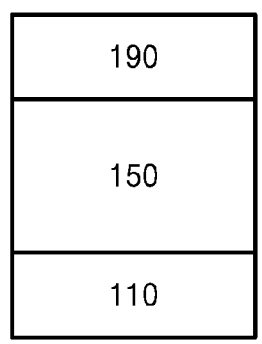
FIG. 1 is a schematic view showing the structure of an organic light-emitting device according to an embodiment of the present disclosure.
Figure 2:
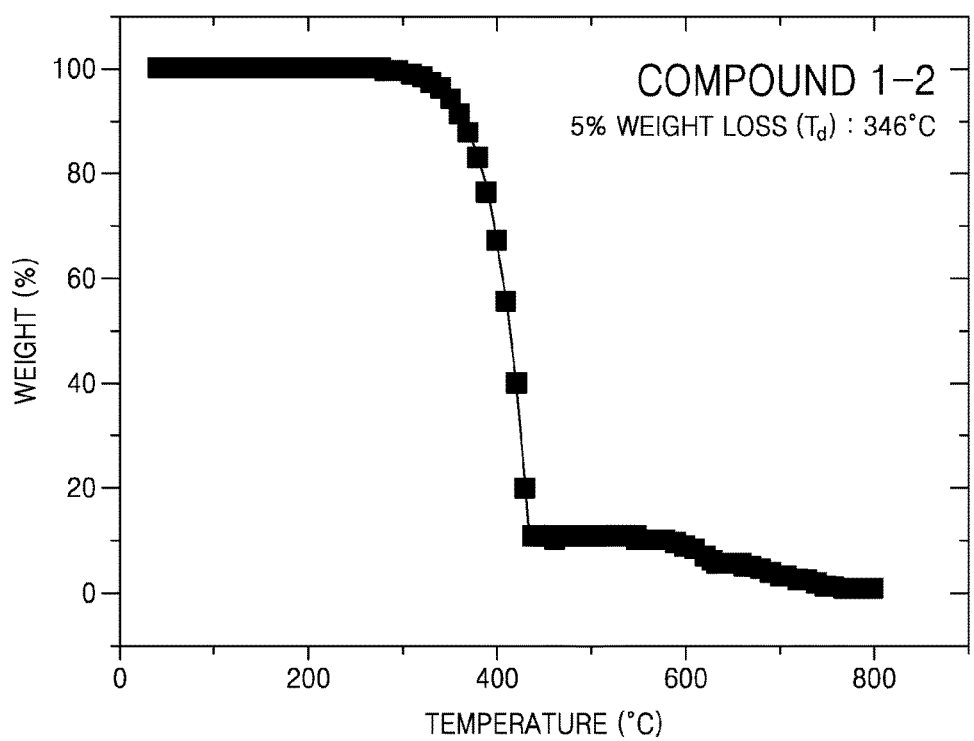
FIG. 2 is a graph of weight (percent, %) versus temperature (Celsius degree, ° C.), illustrating the results of thermogravimetric analysis (TGA) performed on Compound 1-2.
Figure 3:
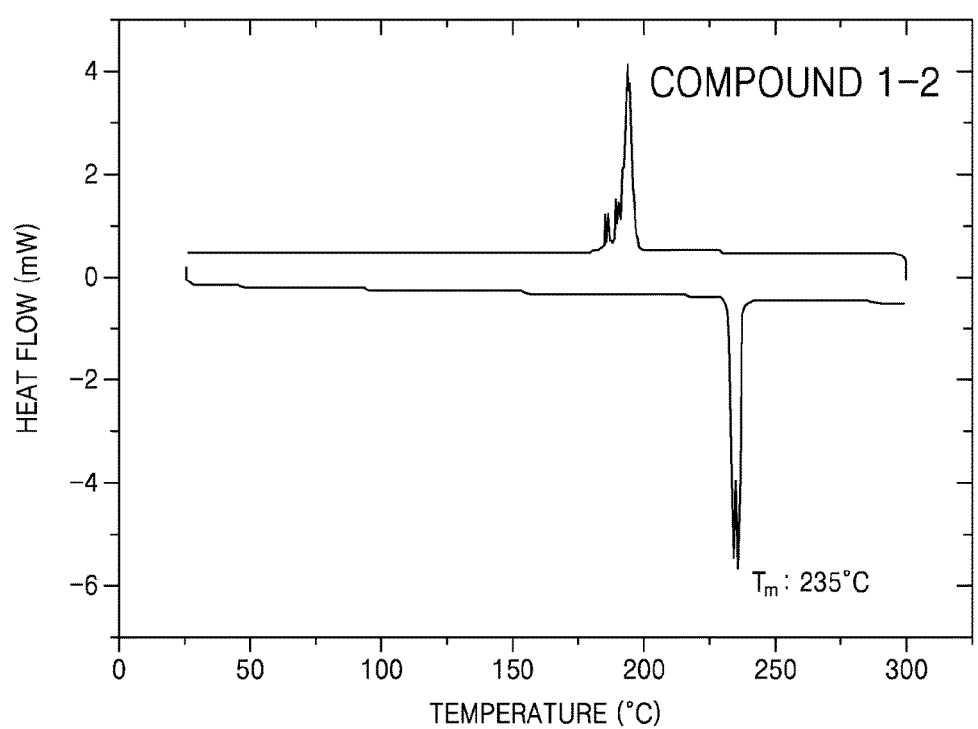
FIG. 3 is a graph of heat flow (mW) versus temperature (° C.), illustrating the results of differential scanning calorimetry (DSC) performed on Compound 1-2.
Figure 4:
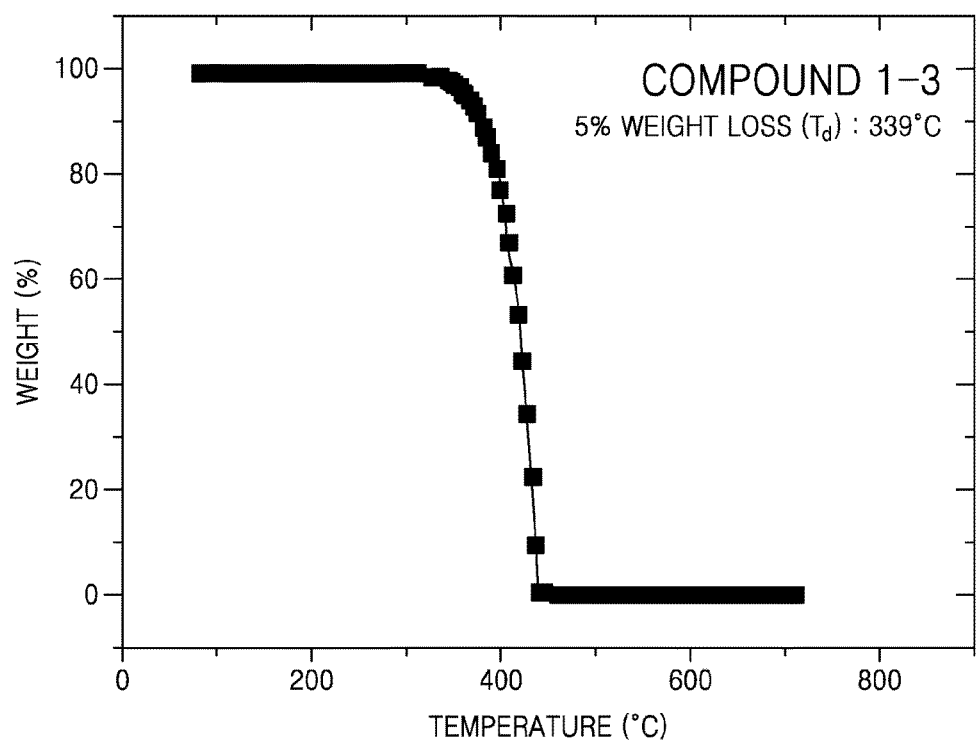
FIG. 4 is a graph of weight (%) versus temperature (° C.), illustrating the results of TGA performed on Compound 1-3.
Figure 5:
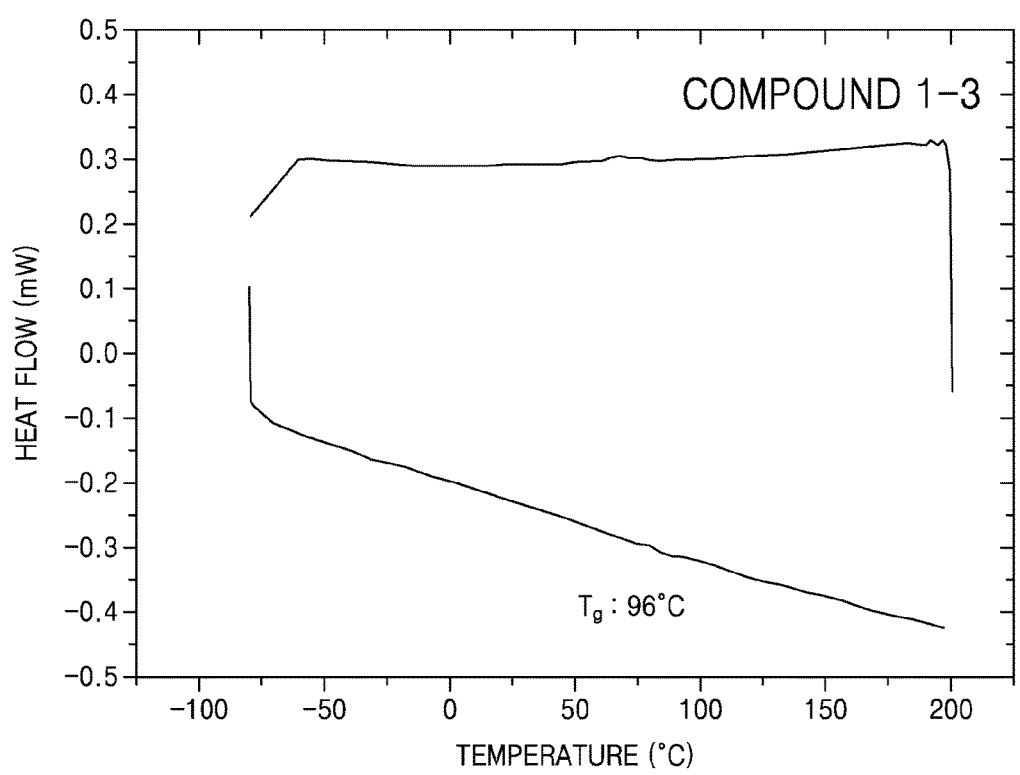
FIG. 5 is a graph of heat flow (mW) versus temperature (° C.), illustrating the results of DSC performed on Compound 1-3.
Figure 6:
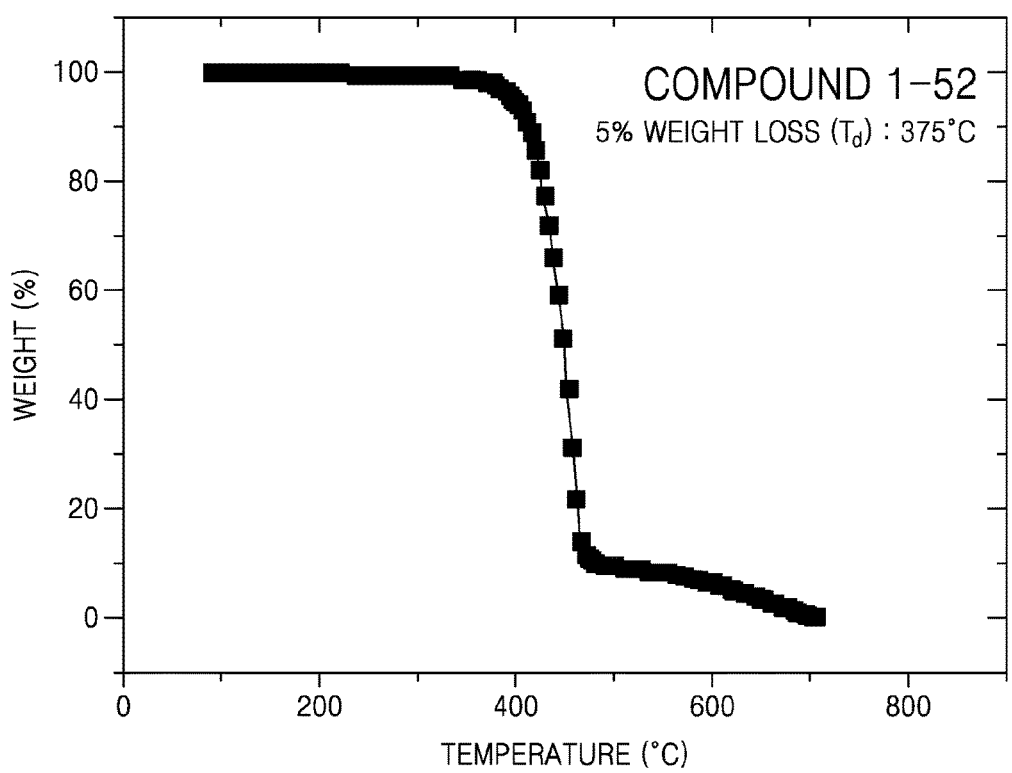
FIG. 6 is a graph of weight (%) versus temperature (° C.), illustrating the results of TGA performed on Compound 1-52.
Figure 7:
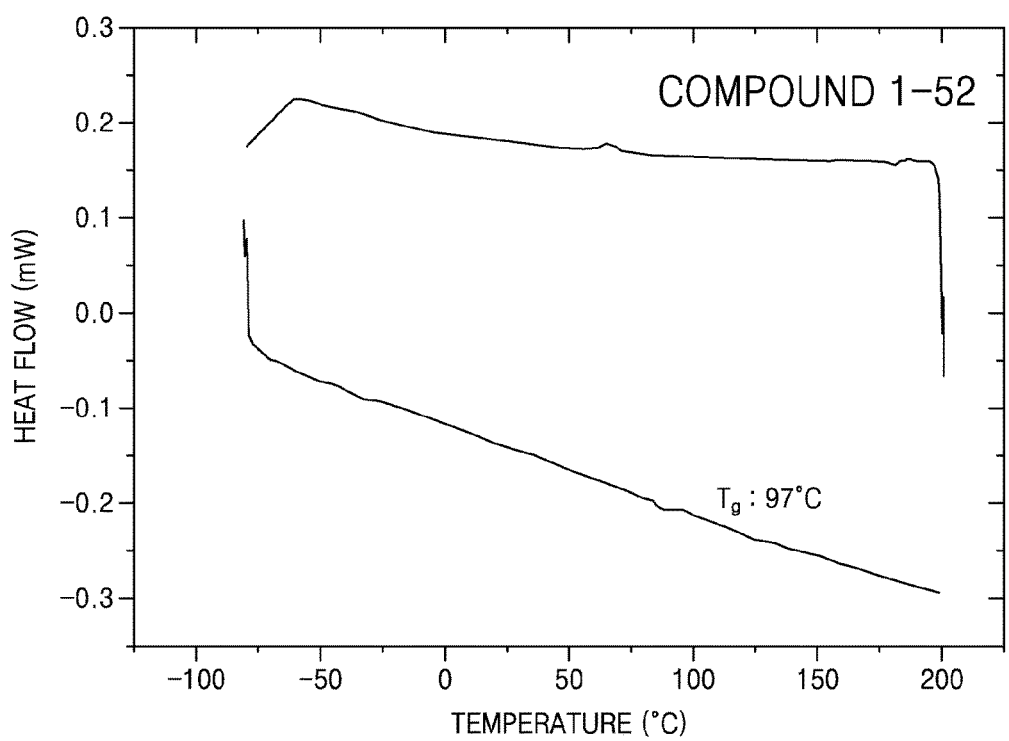
FIG. 7 is a graph of heat flow (mW) versus temperature (° C.), illustrating the results of DSC performed on Compound 1-52.

Reference will now be made in more detail to embodiments, examples of which are illustrated in the accompanying drawings, wherein like reference numerals refer to like elements throughout and duplicative descriptions thereof will not be provided. In this regard, the present embodiments may have different forms and should not be construed as being limited to the descriptions set forth herein. Accordingly, the embodiments are merely described below, by referring to the drawings, to explain aspects of the present description. As used herein, the term "and/or" includes any and all combinations of one or more of the associated listed items.

In the drawings, the thicknesses of layers, films, panels, regions, etc., may be exaggerated for clarity. Like reference numerals designate like elements throughout the specification, and duplicative descriptions thereof may not be provided. It will be understood that when an element such as a layer, film, region, or substrate is referred to as being "on" another element, it can be directly on the other element, or intervening element(s) may also be present. In contrast, when an element is referred to as being "directly on" another element, no intervening elements are present.

An organic light-emitting device according to an embodiment of the present disclosure may include a first electrode, a second electrode facing the first electrode, an emission layer between the first electrode and the second electrode, a hole transport region between the first electrode and the emission layer, and an electron transport region between the emission layer and the second electrode.

The first electrode may be an anode. The second electrode may be a cathode. Descriptions of the first electrode and the second electrode may be understood by referring to the description provided herein.

The organic layer may include a first compound represented by Formula 1 and a second compound represented by Formula 2:

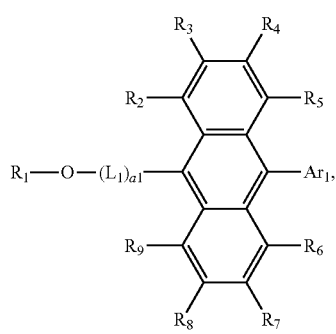

Formula 1

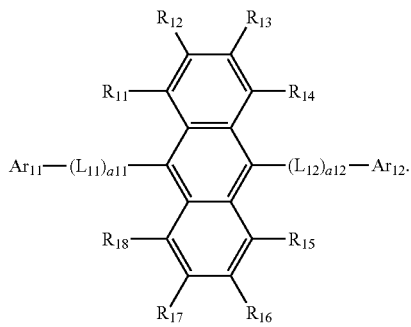

Formula 2

In Formulae 1 and 2, $L_1$, $L_{11}$, and $L_{12}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In one or more embodiments, $L_1$, $L_{11}$, and $L_{12}$ may each independently be selected from the group consisting of:

a phenylene group, a pentalenylene group, an indenylene group, a naphthylene group, an azulenylene group, a heptalenylene group, an indacenylene group, an acenaphthylene group, a fluorenylene group, a spirobifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a benzoisoquinolinylene group, a phthalazinylene group, a naphthyridinylene group, a benzonaphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spirobifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a benzoisoquinolinylene group, a phthalazinylene group, a naphthyridinylene group, a benzonaphthyridinylene group, a quinoxalinylene group, a quinazolinylene group, a cinnolinylene group, a carbazolylene group, a phenanthridinylene group, an achdinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a Iriazolylene group, a tetrazolylene group, an oxadiazolylene group, a Iriazinylene group, a dibenzofuranylene group, a dibsnzothiophenylene group, a dibenzosilolylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino croup, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a benzoisoquinolinyl group, a phthalazinyl group, a naphthyridinyl group, a benzonaphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolylene group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, $L_1$, $L_{11}$, and $L_{12}$ may each independently be selected from groups represented by Formulae 3-1 to 3-43:

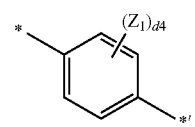

Formula 3-1

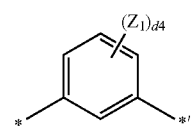

Formula 3-2

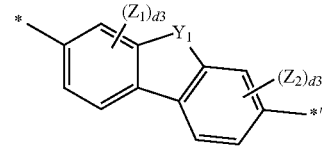

Formula 3-3

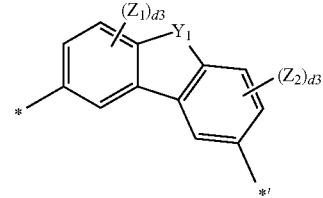

Formula 3-4

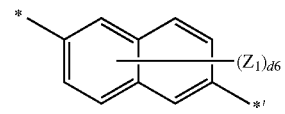

Formula 3-5

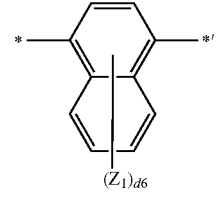

Formula 3-6

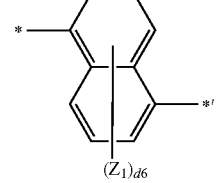

Formula 3-7

-continued
Formula 3-8
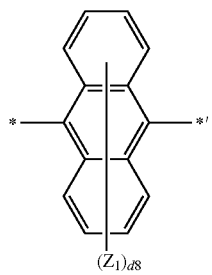
Formula 3-9
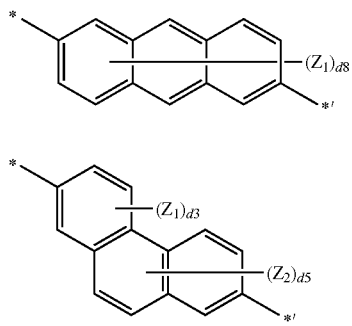
Formula 3-10
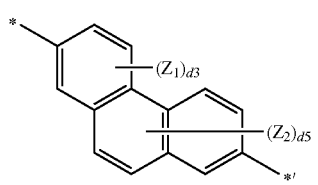
Formula 3-11
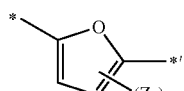
Formula 3-12
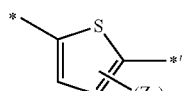
Formula 3-13
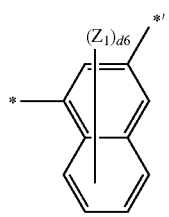
Formula 3-14
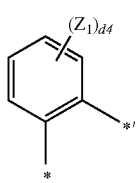
Formula 3-15
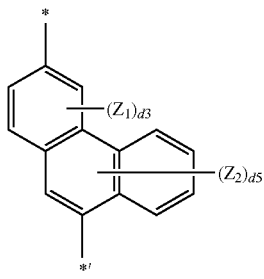
Formula 3-16
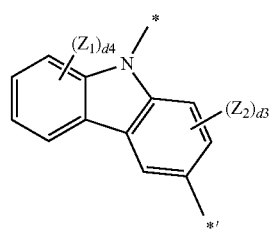
Formula 3-17
Formula 3-18
Formula 3-19
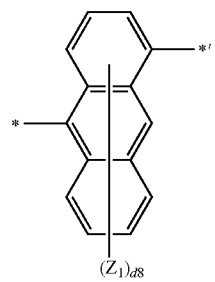
Formula 3-20

Formula 3-21
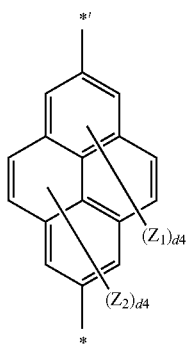
Formula 3-22
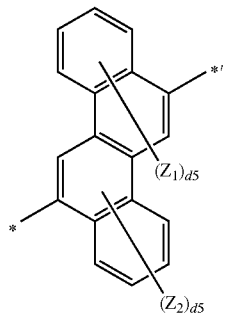
Formula 3-23
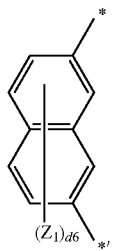
Formula 3-24
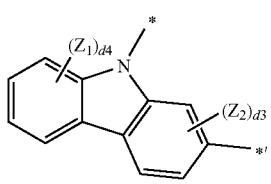
Formula 3-25
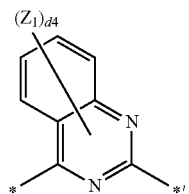
Formula 3-26
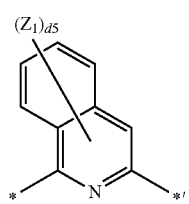
Formula 3-27
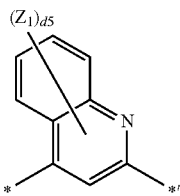
Formula 3-28
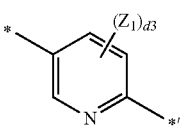
Formula 3-29
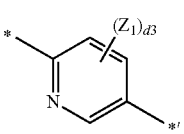
Formula 3-30
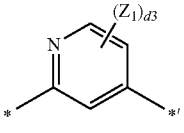
Formula 3-31
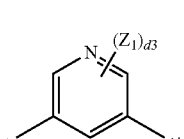
Formula 3-32
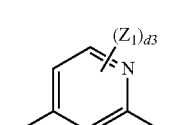
Formula 3-33
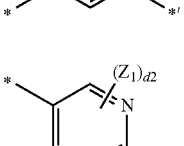
Formula 3-34
Formula 3-35
Formula 3-36

-continued

Formula 3-37

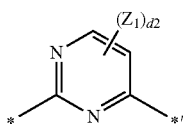
Formula 3-38

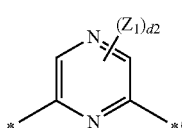
Formula 3-39

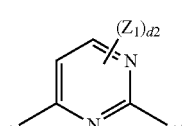
Formula 3-40

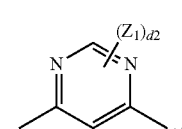
Formula 3-41

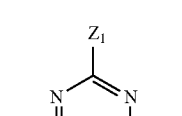
Formula 3-42

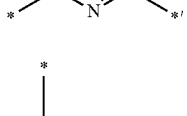
Formula 3-43

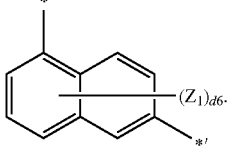

In Formulae 3-1 to 3-43, $Y_1$ may be selected from O, S, $C(Z_3)(Z_4)$, $N(Z_5)$, and $Si(Z_6)(Z_7)$, and $Z_1$ to $Z_7$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, d2 may be an integer selected from 1 and 2, d3 may be an integer selected from 1 to 3, d4 may be an integer selected from 1 to 4, d5 may be an integer selected from 1 to 5, d6 may be an integer selected from 1 to 6, and d8 may be an integer selected from 1 to 8.

In some embodiments, $L_1$, $L_{11}$, and $L_{12}$ may each independently be selected from the group consisting of:

a phenylene group, a naphthylene group, a fluorenylene group, a benzofluorenylene group, a phenanthrenylene group, an anthracenylene group, a pyrenylene group, a chrysenylene group; and a phenylene group, a naphthylene group, a fluorenylene group, a benzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

a1 in Formula 1 indicates the number of $L_1$ groups, and a1 may be an integer selected from 0 to 5. In some embodiments, a1 may be selected from 1 and 2, but embodiments of the present disclosure are not limited thereto. When a1 is 0, *-$(L_1)_{a1}$-*' may be a single bond. When a1 is 2, two $L_1$ groups may be identical to or different from each other.

a11 in Formula 2 indicates the number of $L_{11}$ groups, and a1 may be an integer selected from 0 to 5. In some embodiments, a11 may be selected from 0 and 1, but embodiments of the present disclosure are not limited thereto. When a11 is 0, *-$(L_{11})_{a11}$-*' may be a single bond.

a12 in Formula 2 indicates the number of $L_{12}$ groups, and a1 may be an integer selected from 0 to 5. In some embodiments, a12 may be selected from 0 and 1, but embodiments of the present disclosure are not limited thereto. When a12 is 0, *-$(L_{12})_{a12}$-*' may be a single bond.

In Formula 1, $Ar_1$ may be a substituted or unsubstituted electron transport group.

In one or more embodiments, $Ar_1$ may be selected from the group consisting of:

an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a quinolinyl group, an isoquinolinyl group, a benzoquinolinyl group, a benzoisoquinolinyl group, a phthalazinyl group, a naphthyridinyl group, a benzonaphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, a pyrimidobenzothiophenyl group; and an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a quinolinyl group, an isoquinolinyl group, a benzoquinolinyl group, a benzoisoquinolinyl group, a phthalazinyl group, a naphthyridinyl group, a benzonaphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a pyridinyl group, a pyrimidinyl group, a triazinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, $Ar_1$ may be selected from the group consisting of:

a pyridinyl group, a pyrazinyl group, a pyrimidinyl group, a quinolinyl group, an isoquinolinyl group, a benzoquinolinyl group, a benzoisoquinolinyl group, a naphthyridinyl group, a benzonaphthyridinyl group, a quinoxalinyl group, a quinazolinyl group, a phenanthridinyl group, a phenanthrolinyl group, a benzophenanthrolinyl group, a benzimidazolyl group, a naphthoimidazolyl group, a triazolyl group, an imidazopyridinyl group, an imidazopyrimidinyl group, an imidazoquinolinyl group, an imidazoisoquinolinyl group; and a pyridinyl group, a pyrazinyl group, a pyrimidinyl group, a quinolinyl group, an isoquinolinyl group, a benzoquinolinyl group, a benzoisoquinolinyl group, a naphthyridinyl group, a benzonaphthyridinyl group, a quinoxalinyl group, a quinazolinyl group, a phenanthridinyl group, a phenanthrolinyl group, a benzophenanthrolinyl group, a benzimidazolyl group, a naphthoimidazolyl group, a triazinyl group, an imidazopyridinyl group, an imidazopyrimidinyl group, an imidazoquinolinyl group, and an imidazoisoquinolinyl group, each substituted with at least one selected from deuterium, a $C_1$-$C_{20}$ alkyl group, a phenyl group, a biphenyl group, a terphenyl group, a naphthyl group, a fluorenyl group, a carbazolyl group, a pyridinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, $Ar_1$ may be selected from groups represented by Formulae 7-1 to 7-101:

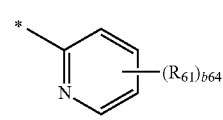
7-1

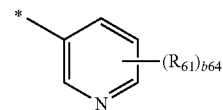
7-2

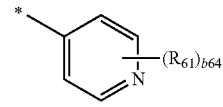
7-3

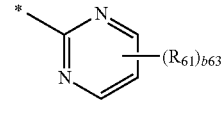
7-4

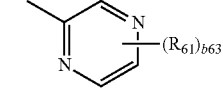
7-5

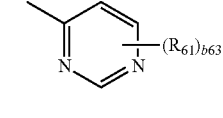
7-6

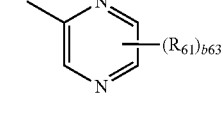
7-7

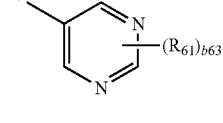
7-8

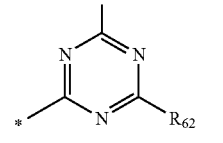
7-9

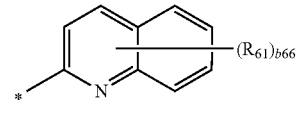
7-10

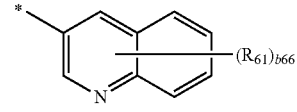
7-11

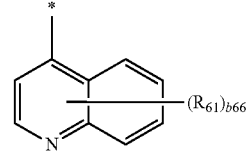
7-12

17
-continued
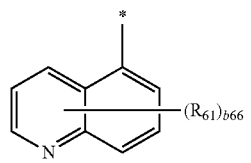
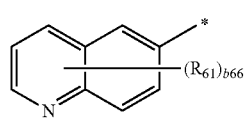
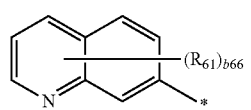
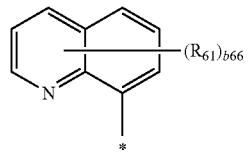
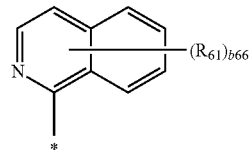
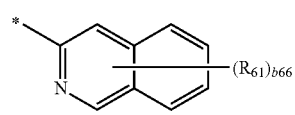
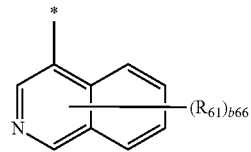
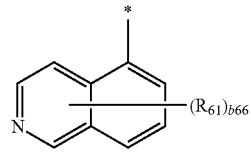
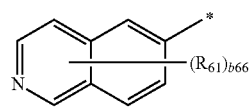
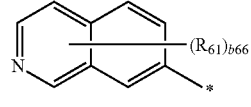
18
-continued
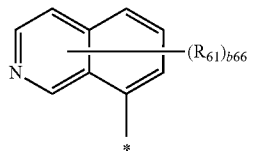 7-13
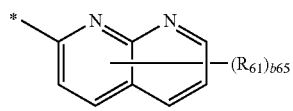 7-14
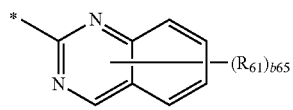 7-15
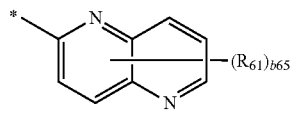 7-16
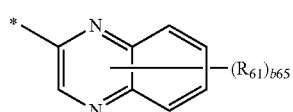 7-17
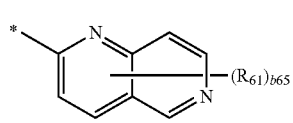 7-18
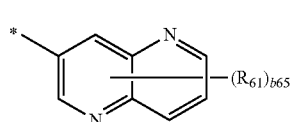 7-19
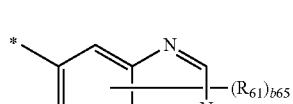 7-20
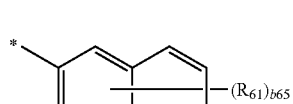 7-21
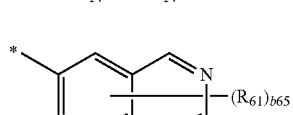 7-22
7-23
7-24
7-25
7-26
7-27
7-28
7-29
7-30
7-31
7-32
7-33
7-34

-continued
| | |
|---|---|
| 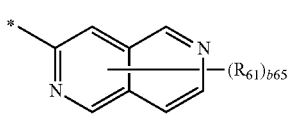 | 7-35 |
| 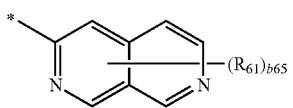 | 7-36 |
| 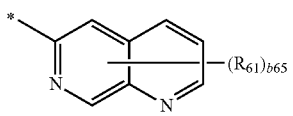 | 7-37 |
| 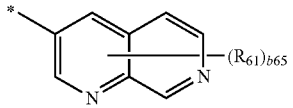 | 7-38 |
| 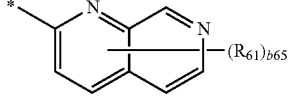 | 7-39 |
| 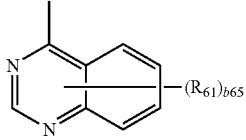 | 7-40 |
| 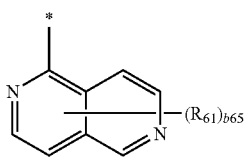 | 7-41 |
| 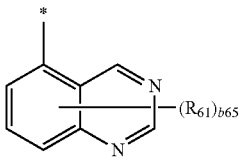 | 7-42 |
| 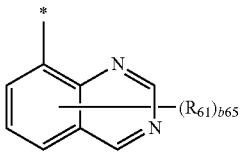 | 7-43 |
| 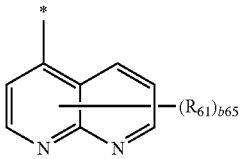 | 7-44 |
-continued
| | |
|---|---|
| 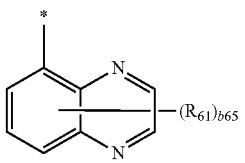 | 7-45 |
| 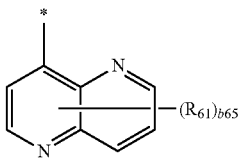 | 7-46 |
| 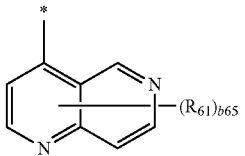 | 7-47 |
| 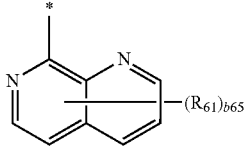 | 7-48 |
| 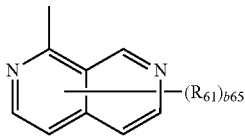 | 7-49 |
| 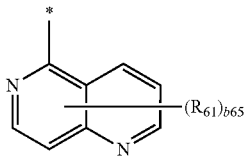 | 7-50 |
| 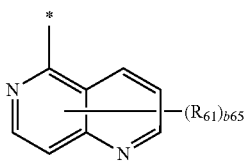 | 7-50 |
| 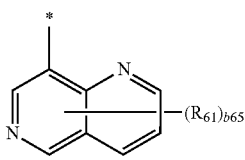 | 7-51 |
| 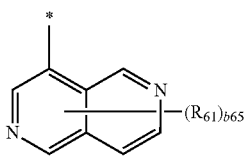 | 7-52 |

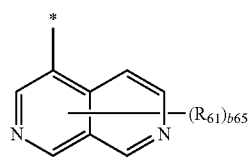
7-53
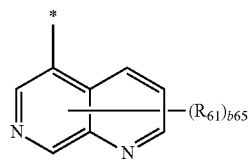
7-54
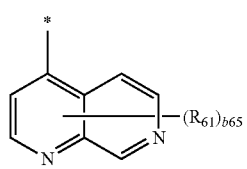
7-55
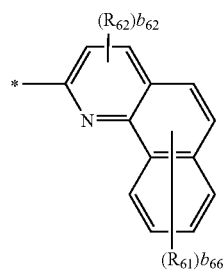
7-56
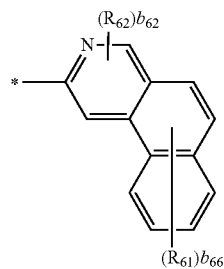
7-57
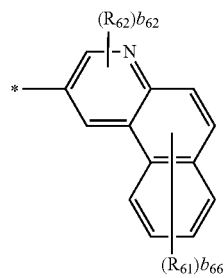
7-58
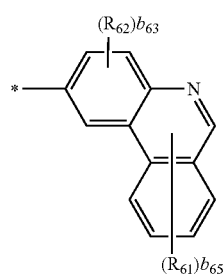
7-59
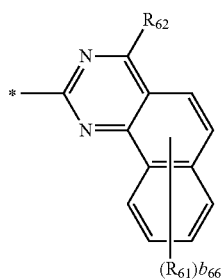
7-60
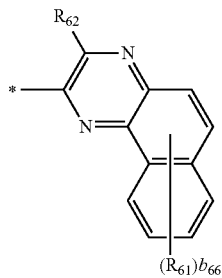
7-61
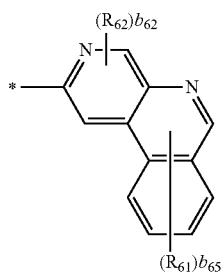
7-62
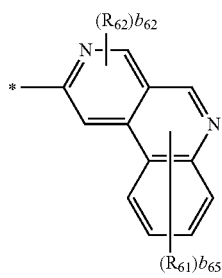
7-63
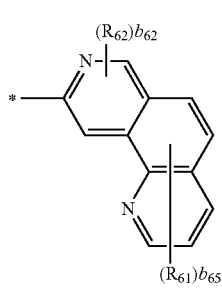
7-64

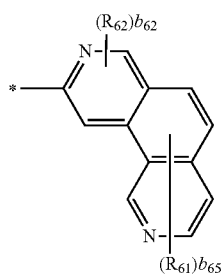
7-65
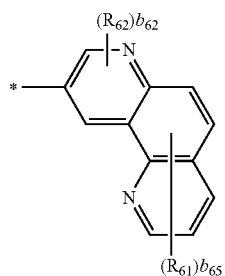
7-70
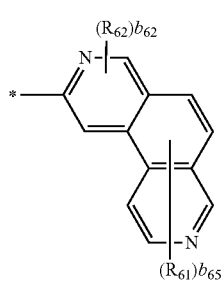
7-66
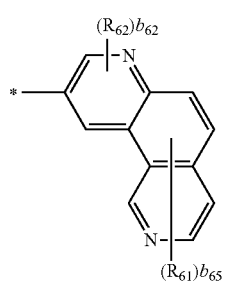
7-71
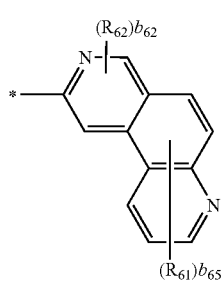
7-67
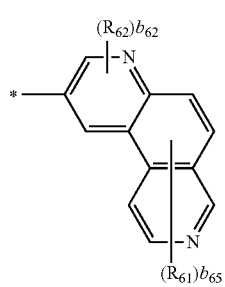
7-72
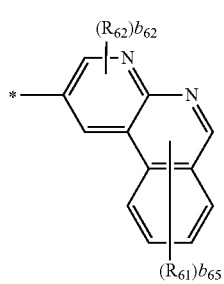
7-68
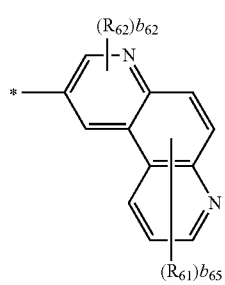
7-73
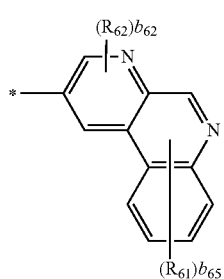
7-69
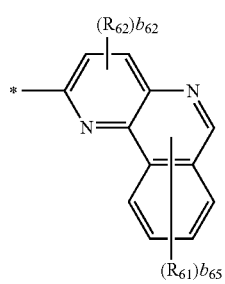
7-74

-continued
7-75 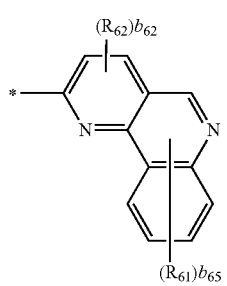
7-76 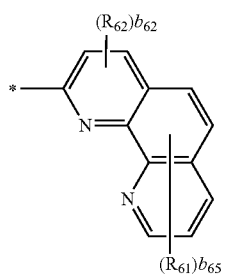
7-77 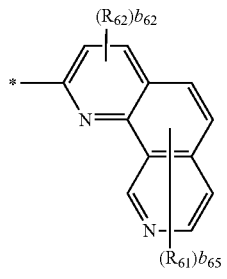
7-78 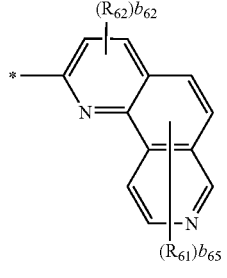
7-79 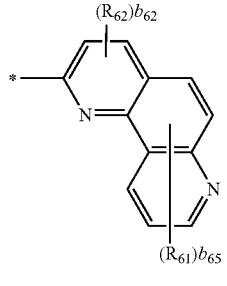
7-80 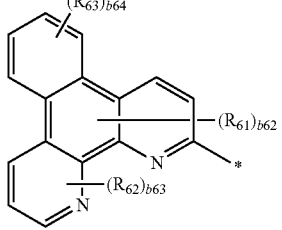
-continued
7-81 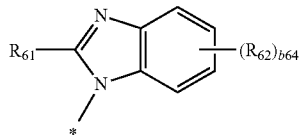
7-82 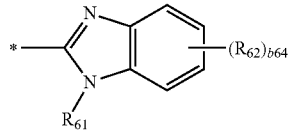
7-83 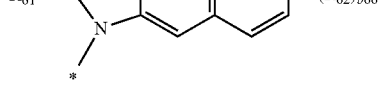
7-84 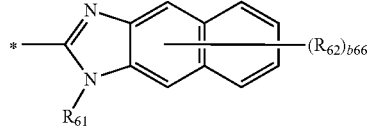
7-85 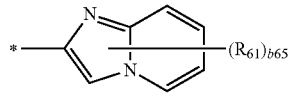
7-86 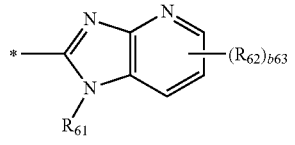
7-87 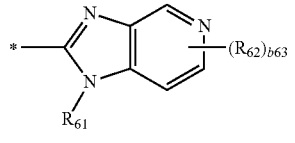
7-88 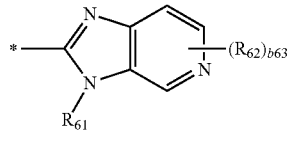
7-89 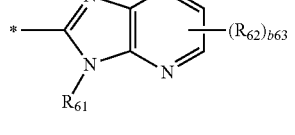
7-90 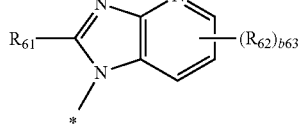

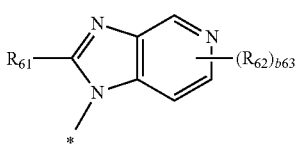
7-91

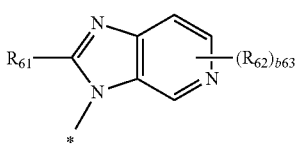
7-92

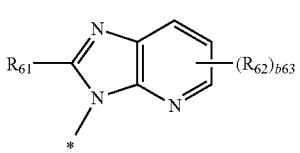
7-93

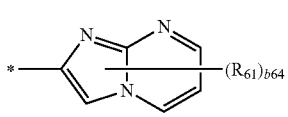
7-94

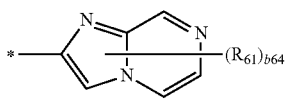
7-95

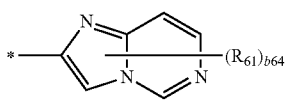
7-96

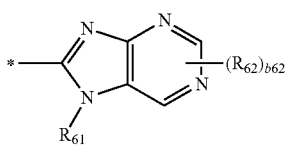
7-97

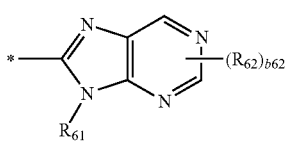
7-98

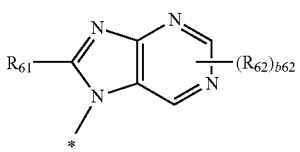
7-99

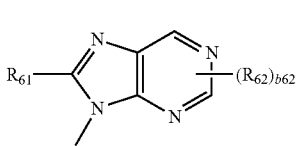
7-100

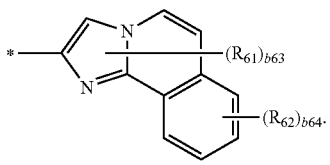
7-101

In Formulae 7-1 to 7-101, $R_{61}$ to $R_{63}$ may each independently be selected from hydrogen, deuterium, a $C_1$-$C_{20}$ alkyl group, a phenyl group, a biphenyl group, a terphenyl group, a naphthyl group, a fluorenyl group, a carbazolyl group, a pyridinyl group, and —Si$(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, b62 may be an integer selected from 1 and 2, b63 may be an integer selected from 1 to 3, b64 may be an integer selected from 1 to 4, b65 may be an integer selected from 1 to 5, b66 may be an integer selected from 1 to 6, and * may indicate a binding site to an adjacent atom.

In some embodiments, $Ar_1$ may be selected from the group consisting of:

a pyridinyl group, a pyrazinyl group, a pyrimidinyl group, a quinolinyl group, an isoquinolinyl group, a benzoquinolinyl group, a benzoisoquinolinyl group, a naphthyridinyl group, a benzonaphthyridinyl group, a quinoxalinyl group, a quinazolinyl group, a phenanthridinyl group, a phenanthrolinyl group, a benzophenanthrolinyl group; and a pyridinyl group, a pyrazinyl group, a pyrimidinyl group, a quinolinyl group, an isoquinolinyl group, a benzoquinolinyl group, a benzoisoquinolinyl group, a naphthyridinyl group, a benzonaphthyridinyl group, a quinoxalinyl group, a quinazolinyl group, a phenanthridinyl group, a phenanthrolinyl group, and a benzophenanthrolinyl group, each substituted with at least one selected from deuterium, a $C_1$-$C_{20}$ alkyl group, a phenyl group, a biphenyl group, a terphenyl group, a naphthyl group, a fluorenyl group, a carbazolyl group, a pyridinyl group, and —Si$(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In Formulae 1 and 2, $Ar_{11}$ and $Ar_{12}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, $Ar_{11}$ and $Ar_{12}$ may each independently be selected from the group consisting of:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a dibenzofuranyl group, a benzothiophenyl group, a dibenzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, an imidazopyrimidinyl group, a naphthoxanthenyl group, a dibenzosilolyl group, a benzonaphthofuranyl group, a benzopyrenyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a dibenzofuranyl group, a benzothiophenyl group, a dibenzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, an imidazopyrimidinyl group, a naphthoxanthenyl group, a dibenzosilolyl group, a benzonaphthofuranyl group, and a benzopyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In some embodiments, $Ar_{11}$ and $Ar_{12}$ may each independently be selected from groups represented by Formulae 5-1 to 5-23:

Formula 5-1

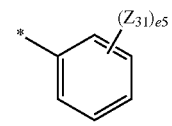

Formula 5-2

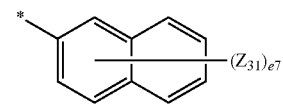

Formula 5-3

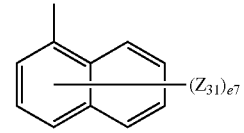

Formula 5-4

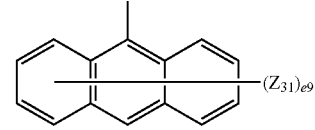

Formula 5-5

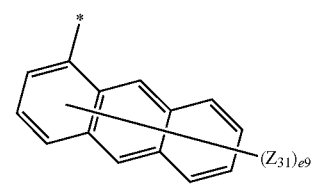

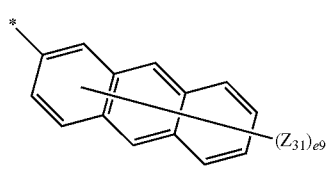
Formula 5-6
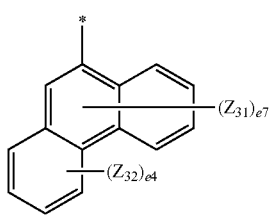
Formula 5-7
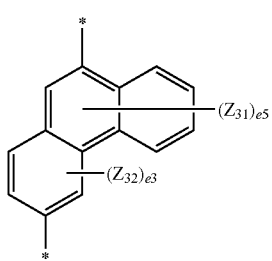
Formula 5-8
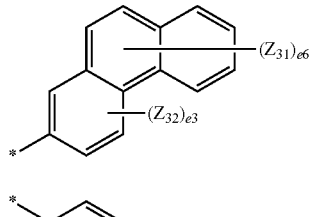
Formula 5-9
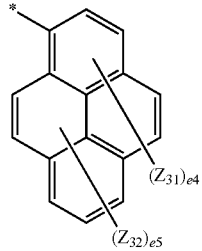
Formula 5-10
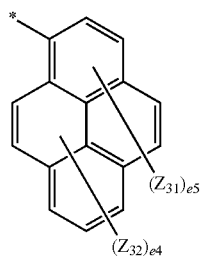
Formula 5-11
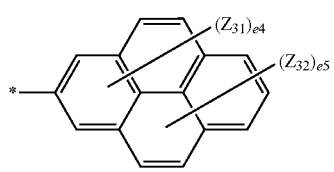
Formula 5-12
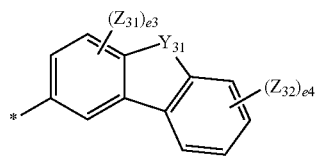
Formula 5-13
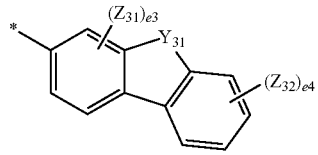
Formula 5-14
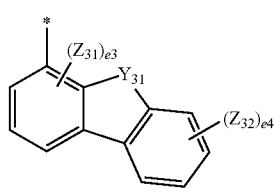
Formula 5-15
Formula 5-16
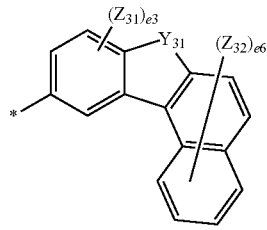
Formula 5-17
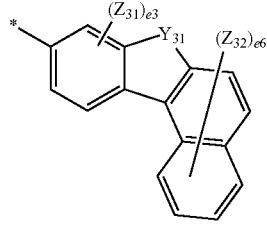
Formula 5-18
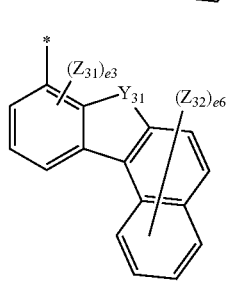
Formula 5-19
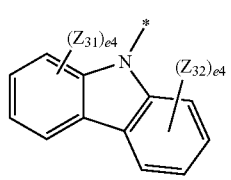
Formula 5-20

-continued

Formula 5-21
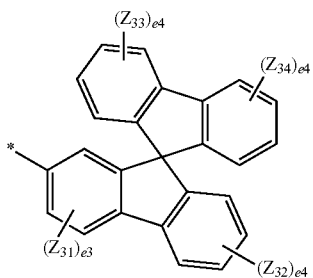

Formula 5-22
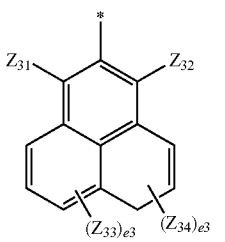

Formula 5-23
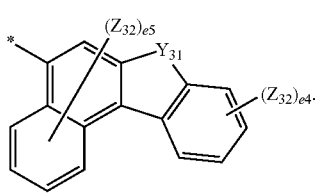

In Formulae 5-1 to 5-23,

Y$_{31}$ may be selected from O, S, C(Z$_{33}$)(Z$_{34}$), N(Z$_{35}$), and Si(Z$_{36}$)(Z$_{37}$), and Z$_{31}$ to Z$_{37}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a triazinyl group, and —Si(Q$_{31}$)(Q$_{32}$)(Q$_{33}$), wherein Q$_{31}$ to Q$_{33}$ may each independently be selected from a C$_1$-C$_{10}$ alkyl group, a C$_1$-C$_{10}$ alkoxy group, a phenyl group, a biphenyl group, a terphenyl group, and a naphthyl group, e3 may be an integer selected from 1 to 3, e4 may be an integer selected from 1 to 4, e5 may be an integer selected from 1 to 5, e6 may be an integer selected from 1 to 6, e7 may be an integer selected from 1 to 7, e8 may be an integer selected from 1 to 8, e9 may be an integer selected from 1 to 9, and * may indicate a binding site to an adjacent atom.

In some embodiments, Ar$_{11}$ and Ar$_{12}$ may each independently be selected from groups represented by Formulae 6-1 to 6-54, but embodiments of the present disclosure are not limited thereto:

Formula 6-1
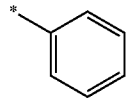

Formula 6-2
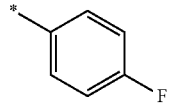

Formula 6-3
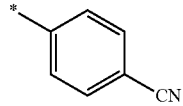

Formula 6-4
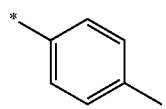

Formula 6-5
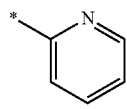

Formula 6-6
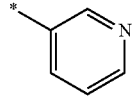

Formula 6-7

Formula 6-8
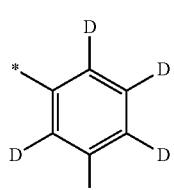

Formula 6-9
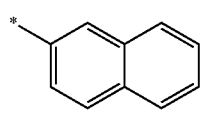

Formula 6-10
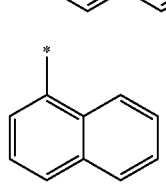

Formula 6-11
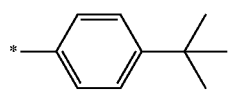

Formula 6-12
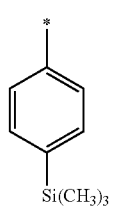

-continued
Formula 6-13
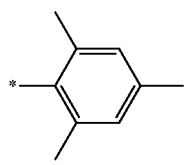
Formula 6-14
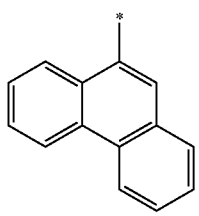
Formula 6-15
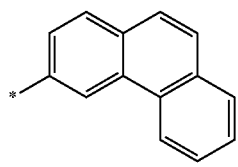
Formula 6-16
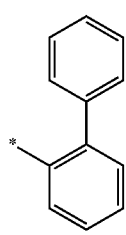
Formula 6-17
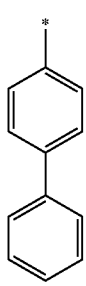
Formula 6-18
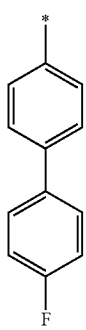
-continued
Formula 6-19
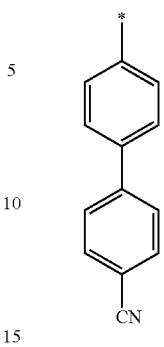
Formula 6-20
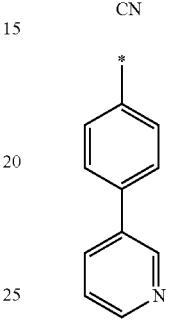
Formula 6-21
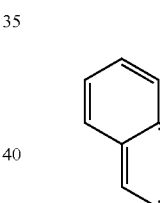
Formula 6-22
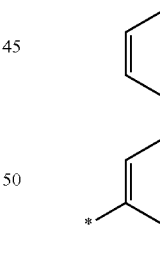
Formula 6-23
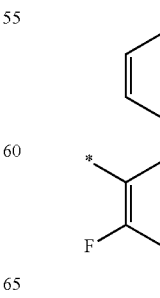
Formula 6-24
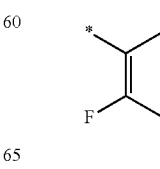

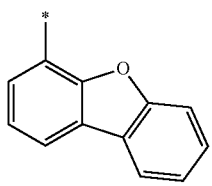
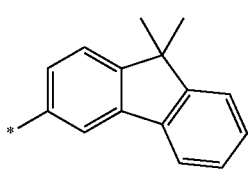

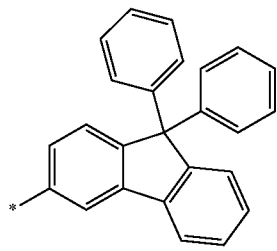
Formula 6-42
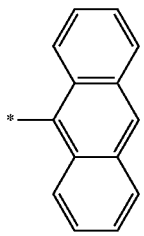
Formula 6-48
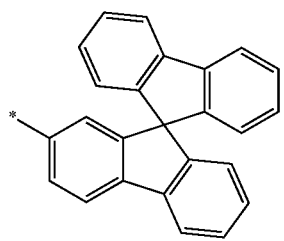
Formula 6-43
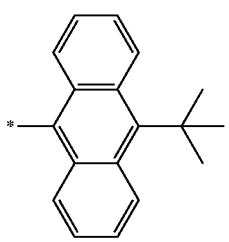
Formula 6-49
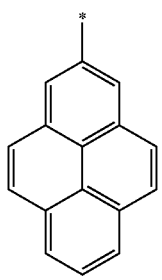
Formula 6-44
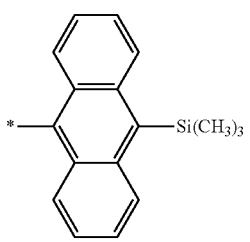
Formula 6-50
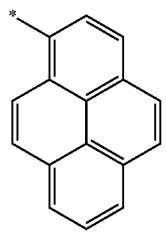
Formula 6-45
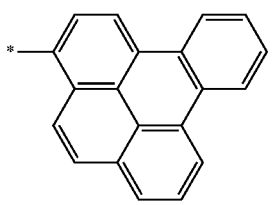
Formula 6-51
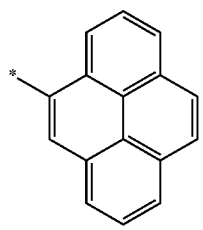
Formula 6-46
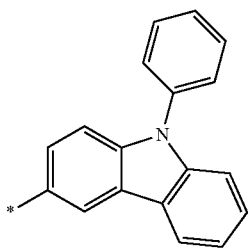
Formula 6-52
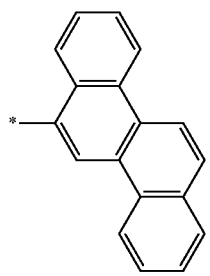
Formula 6-47
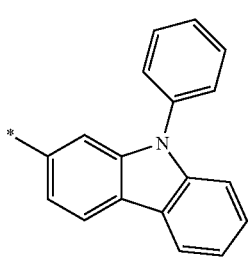
Formula 6-53

-continued

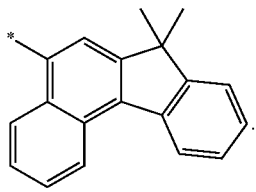

Formula 6-54

In Formulae 6-1 to 6-54, * may indicate a binding site to an adjacent atom.

In Formulae 1 and 2, $R_1$ may be selected from the group consisting of:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{60}$ alkyl group; and a $C_1$-$C_{60}$ alkyl group substituted with at least one selected from deuterium, —F, —Cl, —Br, —I, a hydroxyl group, a cyano group, a nitro group, a carboxylic acid group or a salt thereof, a sulfonic acid group or a salt thereof, and a phosphoric acid group or a salt thereof, and $R_2$ to $R_9$ and $R_{11}$ to $R_{18}$ may each independently be selected from:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$).

In one or more embodiments, $R_1$ may be selected from the group consisting of:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{60}$ alkyl group; and a $C_1$-$C_{60}$ alkyl group substituted with at least one selected from deuterium, —F, —Cl, —Br, —I, a hydroxyl group, a cyano group, a nitro group, a carboxylic acid group or a salt thereof, a sulfonic acid group or a salt thereof, and a phosphoric acid group or a salt thereof, and $R_2$ to $R_9$ and $R_{11}$ to $R_{18}$ may each independently be selected from the group consisting of:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group;

a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, an imidazopyrimidinyl group;

a $C_1$-$C_{20}$ alkyl group, a $C_1$-$C_{20}$ alkoxy group, a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, and an imidazopyrimidinyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, a dibenzosilolyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a phenyl group, a biphenyl group, a terphenyl group, and a naphthyl group.

In some embodiments, $R_1$ may be selected from the group consisting of:

hydrogen, deuterium, a $C_1$-$C_{20}$ alkyl group; and a $C_1$-$C_{20}$ alkyl group substituted with at least one selected from deuterium, —F, —Cl, —Br, —I, a hydroxyl group, a cyano group, a nitro group, a carboxylic acid group or a salt thereof, a sulfonic acid group or a salt thereof, and a phosphoric acid group or a salt thereof, but embodiments of the present disclosure are not limited thereto.

In some embodiments, $R_2$ to $R_9$ and $R_{11}$ to $R_{18}$ may each independently be selected from the group consisting of:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group;

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a phenyl group, a biphenyl group, a terphenyl group, and a naphthyl group, but embodiments of the present disclosure are not limited thereto.

In some embodiments, the first compound may be represented by Formula 1A, and the second compound may be represented by one selected from Formulae 2A to 2C, but embodiments of the present disclosure are not limited thereto:

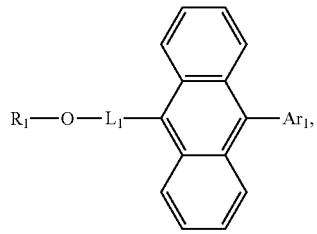

Formula 1A

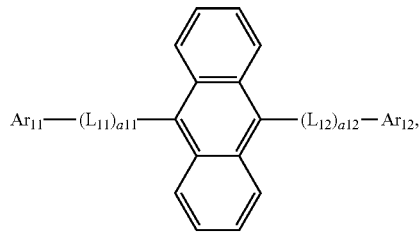

Formula 2A

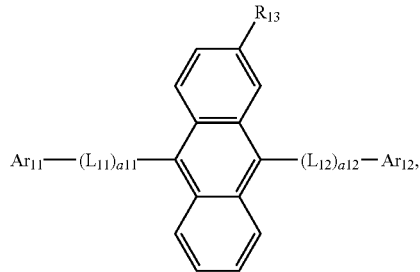

Formula 2B

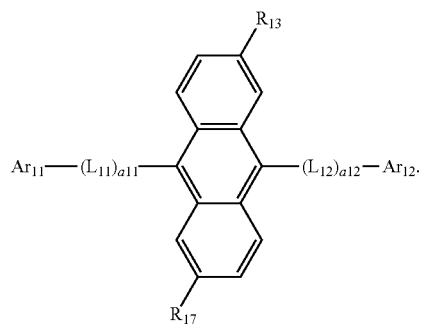

Formula 2C

In Formulae 1A, 2A, 2B, and 2C, $L_1$, $L_{11}$, $L_{12}$, a11, a12, $Ar_1$, $Ar_{11}$, $Ar_{12}$, $R_1$, $R_{13}$, and $R_{17}$ may each be the same as described herein in connection with Formulae 1 and 2, provided that $R_{13}$ and $R_{17}$ are both not hydrogen.

In some embodiments, $L_1$, $L_{11}$, and $L_{12}$ may each independently be selected from the group consisting of:

a phenylene group, a naphthylene group, a fluorenylene group, a benzofluorenylene group, a phenanthrenylene group, an anthracenylene group, a pyrenylene group, a chrysenylene group; and a phenylene group, a naphthylene group, a fluorenylene group, a benzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$), a11 and a12 may each independently be selected from 0 and 1, $Ar_1$ may be selected from the group consisting of:

a pyridinyl group, a pyrazinyl group, a pyrimidinyl group, a quinolinyl group, an isoquinolinyl group, a benzoquinolinyl group, a benzoisoquinolinyl group, a naphthyridinyl group, a benzonaphthyridinyl group, a quinoxalinyl group, a quinazolinyl group, a phenanthridinyl group, a phenanthrolinyl group, a benzophenanthrolinyl group; and a pyridinyl group, a pyrazinyl group, a pyrimidinyl group, a quinolinyl group, an isoquinolinyl group, a benzoquinolinyl group, a benzoisoquinolinyl group, a naphthyridinyl group, a benzonaphthyridinyl group, a quinoxalinyl group, a quinazolinyl group, a phenanthridinyl group, a phenanthrolinyl group, and a benzophenanthrolinyl group, each substituted with at least one selected from deuterium, a $C_1$-$C_{20}$ alkyl group, a phenyl group, a biphenyl group, a terphenyl group, a naphthyl group, a fluorenyl group, a carbazolyl group, a pyridinyl group, and —Si($Q_{31}$)($Q_{32}$)($Q_{33}$), $Ar_{11}$ and $Ar_{12}$ may each independently be selected from the group consisting of:

a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a naphthacenyl group, a carbazolyl group, a benzofuranyl group, a dibenzofuranyl group, a benzothiophenyl group, a dibenzothiophenyl group; and a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a naphthacenyl group, a carbazolyl group, a benzofuranyl group, a dibenzofuranyl group, a benzothiophenyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$), $R_1$ may be selected from the group consisting of:

hydrogen, deuterium, a $C_1$-$C_{20}$ alkyl group; and a $C_1$-$C_{20}$ alkyl group substituted with at least one selected from deuterium, —F, —Cl, —Br, —I, a hydroxyl group, a cyano group, a nitro group, a carboxylic acid group or a salt thereof, a sulfonic acid group or a salt thereof, and a phosphoric acid group or a salt thereof, and $R_{13}$ to $R_{17}$ may each independently be selected from the group consisting of:

deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group;

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from a methyl group, an ethyl group, an n-propyl group, an iso-propyl group, an n-butyl group, an iso-butyl group, a sec-butyl group, a tert-butyl group, a phenyl group, a biphenyl group, a terphenyl group, a naphthyl group, and a fluorenyl group, but embodiments of the present disclosure are not limited thereto.

In some embodiments, the first compound may be represented by Formula 1A-1, and the second compound may be represented by one selected from Formulae 2A to 2C, but embodiments of the present disclosure are not limited thereto:

Formula 1A-1

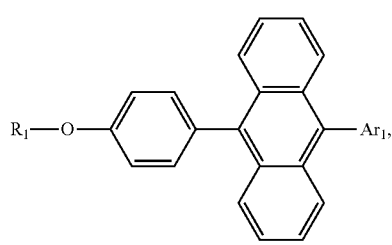

Formula 2A

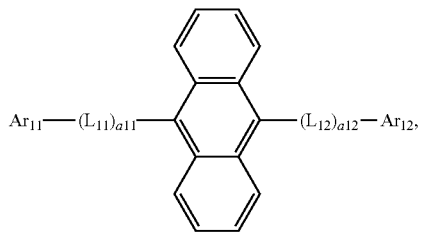

Formula 2B

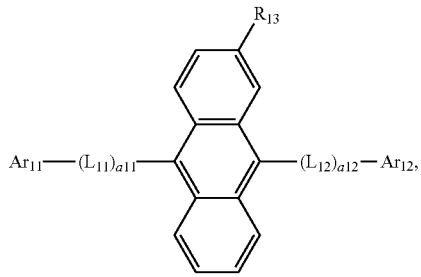

Formula 2C

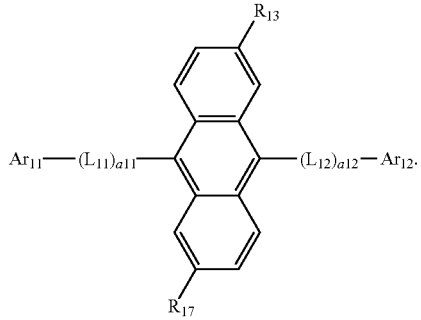

In Formulae 1A-1, 2A, 2B, and 2C, $L_{11}$, $L_{12}$, a11, a12, $Ar_1$, $Ar_{11}$, $Ar_{12}$, $R_1$, $R_{13}$, and $R_{17}$ may each be the same as described herein in connection with Formulae 1 and 2, provided that $R_{13}$ and $R_{17}$ are both not hydrogen.

In some embodiments, the first electrode may be an anode, the second electrode may be a cathode, the organic layer may include a hole transport region between the first electrode and the emission layer and an electron transport region between the emission layer and the second electrode, the hole transport region may include at least one selected from a hole injection layer, a hole transport layer, a buffer layer, and an electron blocking layer, and the electron transport region may include at least one selected from a hole blocking layer, an electron transport layer, and an electron injection layer.

In some embodiments, the emission layer may include a dopant and a host. The dopant may include the first compound, the host may include the second compound, and the amount of the host may be greater than the amount of the dopant.

In some embodiments, the first compound may be represented by one selected from Compounds 1-1 to 1-59, and the second compound may be represented by one selected from Compounds 2-1 to 2-81, but embodiments of the present disclosure are not limited thereto:

-continued
1-1
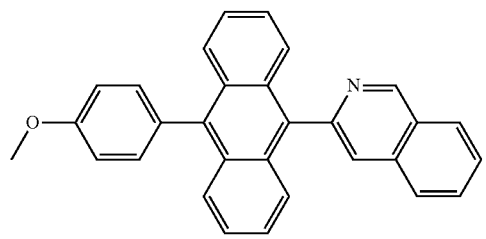
1-2
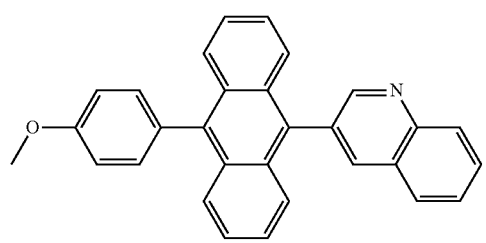
1-3
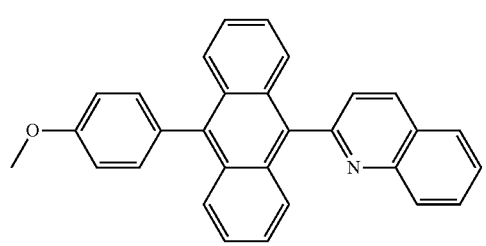
1-4
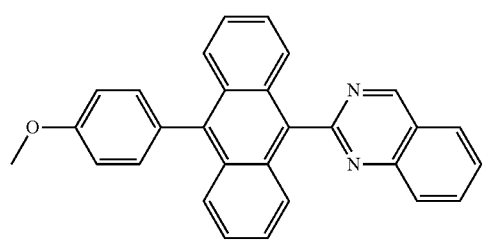
1-5
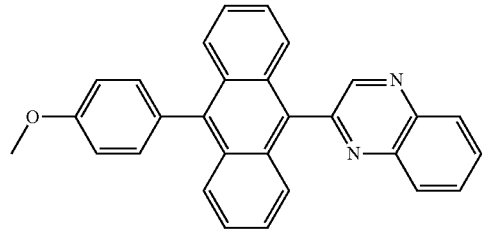
1-6
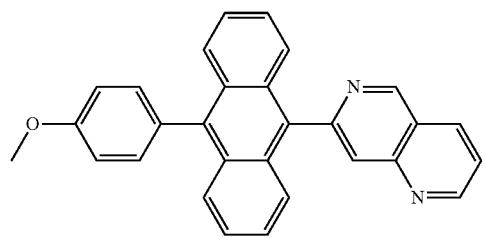
1-7
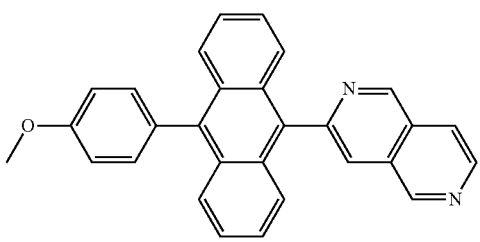
1-8
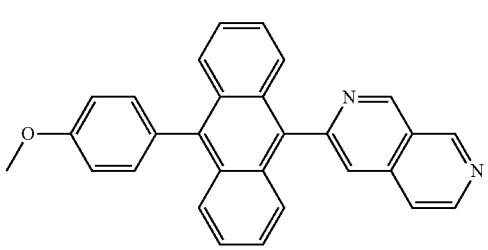
1-9
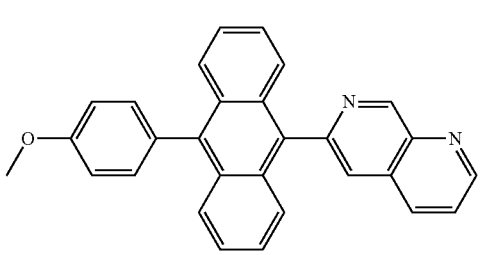
1-10
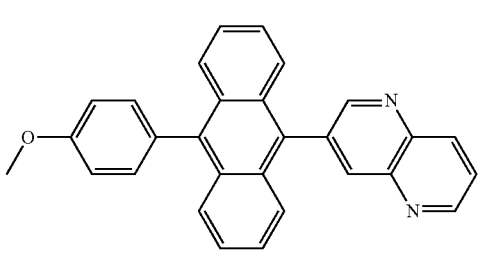
1-11
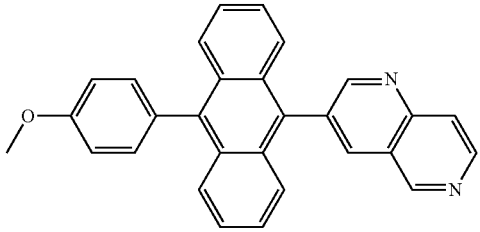
1-12
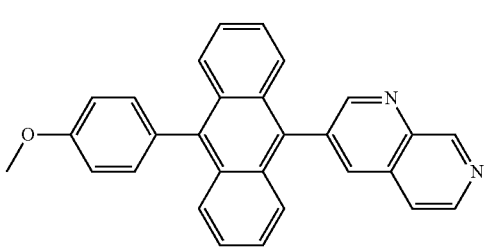

1-13
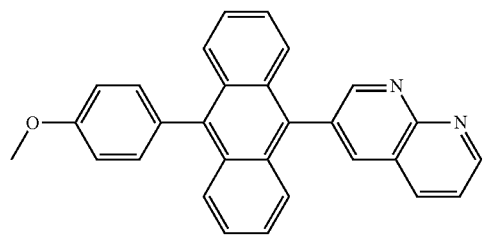
1-19
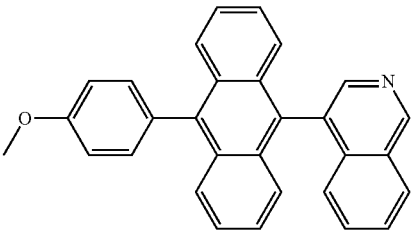
1-14
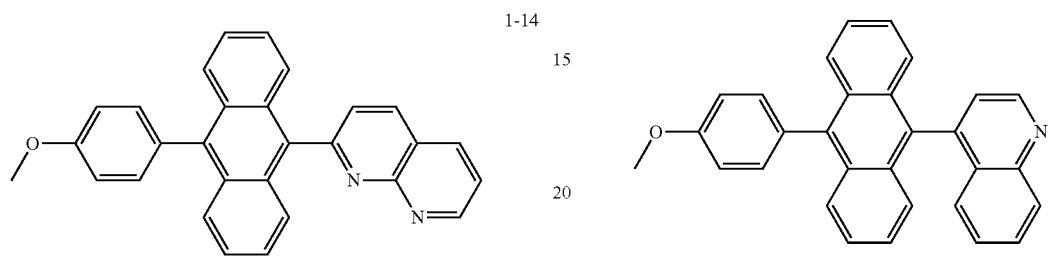
1-20
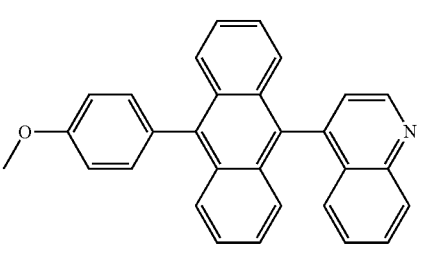
1-15
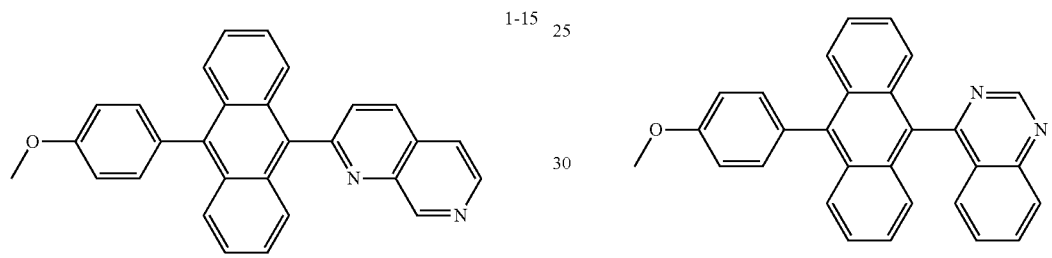
1-21
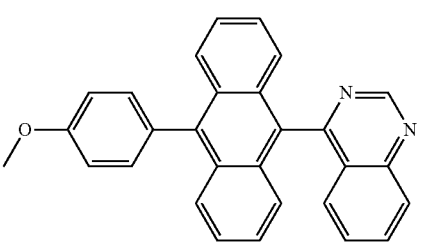
1-16
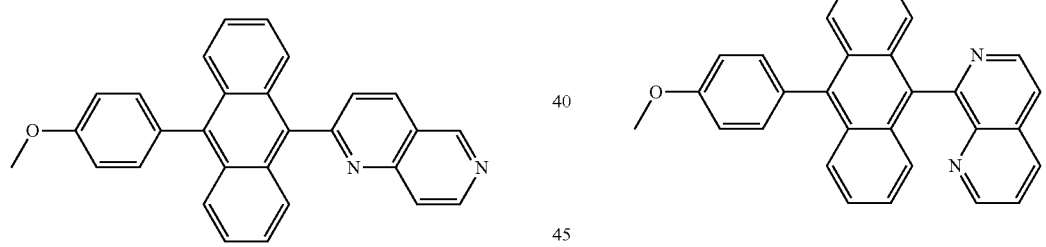
1-22
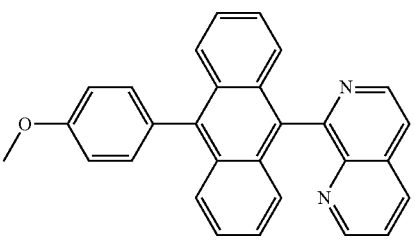
1-17
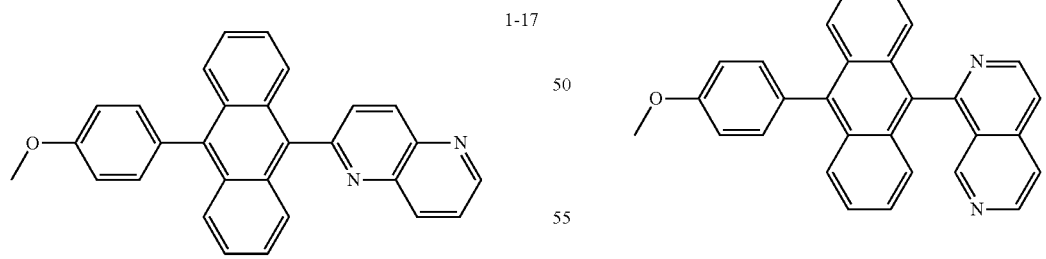
1-23
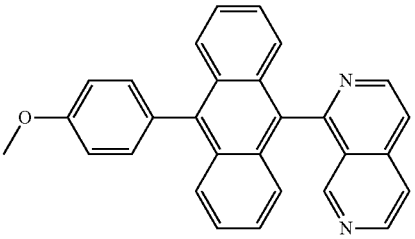
1-18
1-24
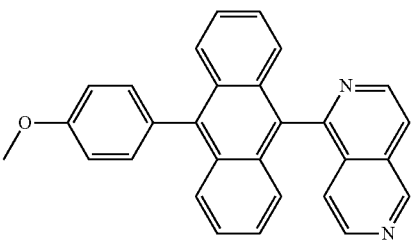

1-25
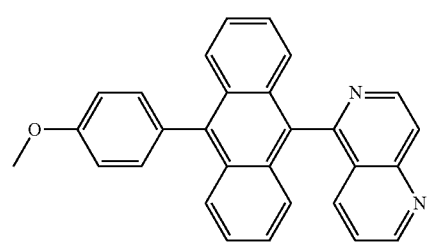
1-26
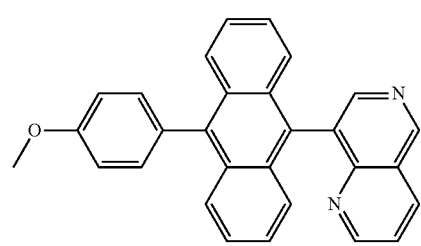
1-27
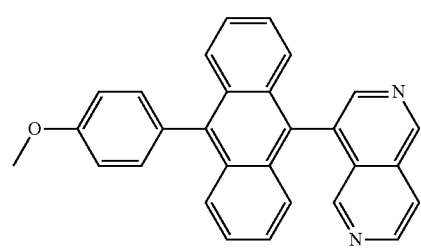
1-28
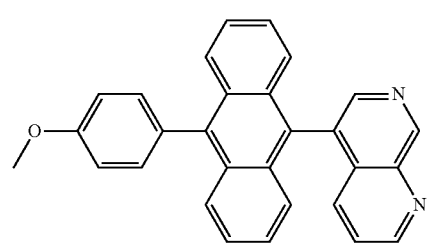
1-29
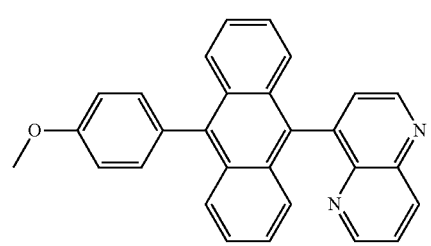
1-30
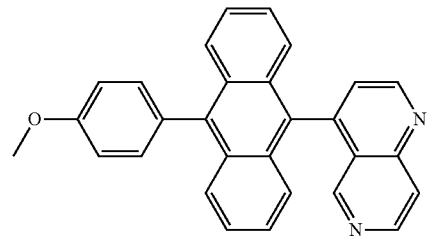
1-31
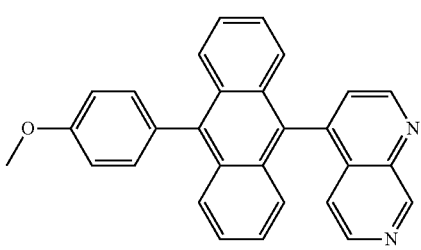
1-32
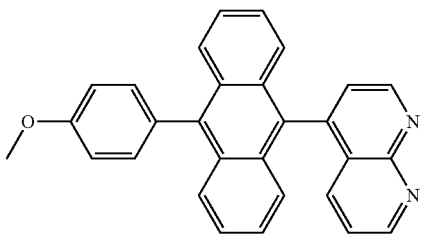
1-33
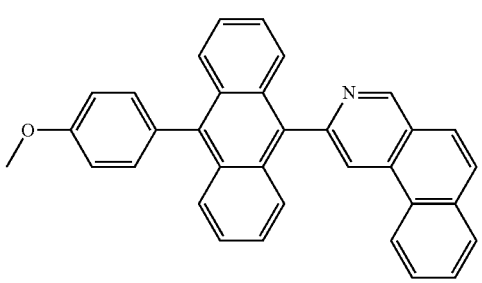
1-34
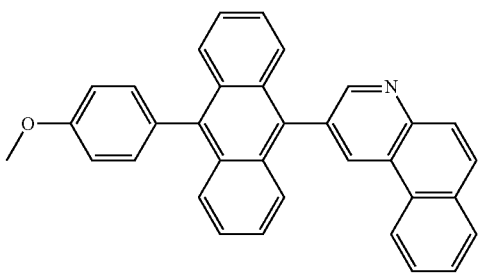
1-35
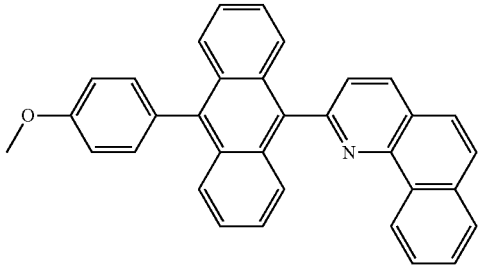
1-36
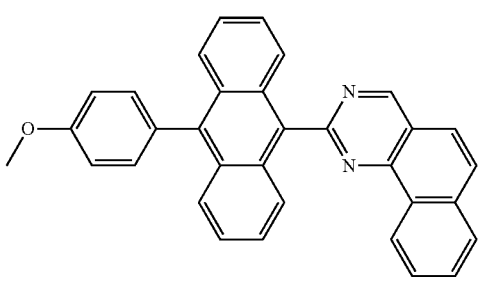

1-37
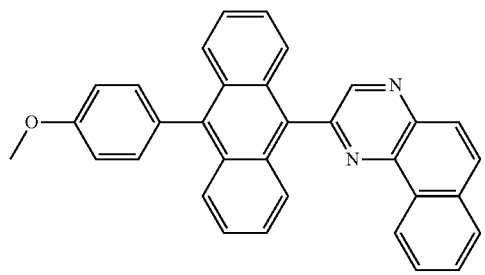
1-38
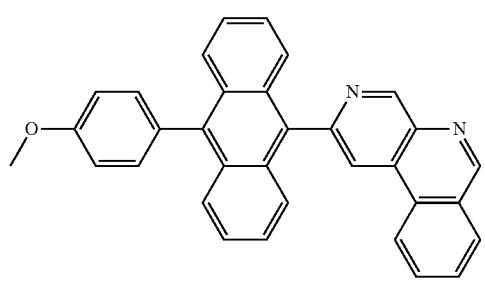
1-39
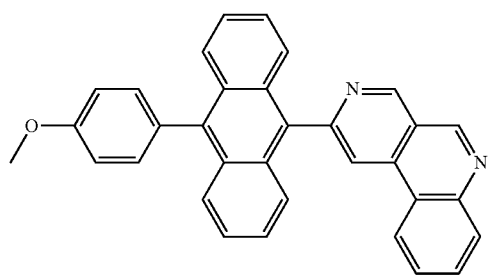
1-40
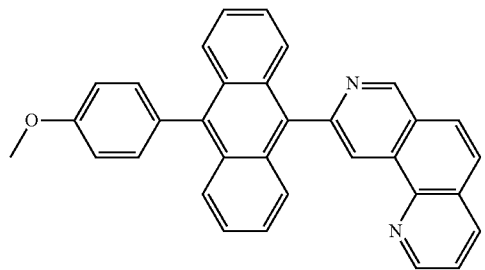
1-41
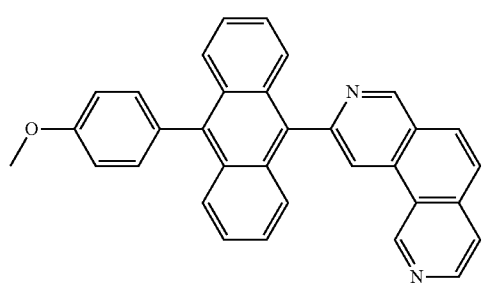
1-42
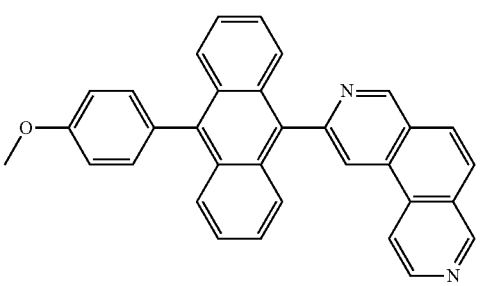
1-43
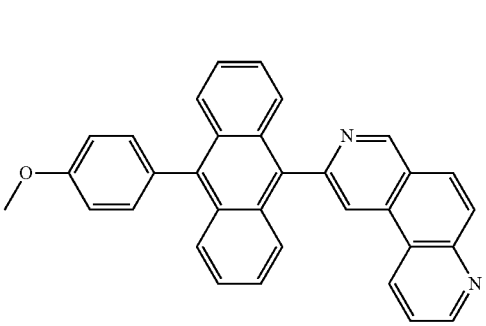
1-44
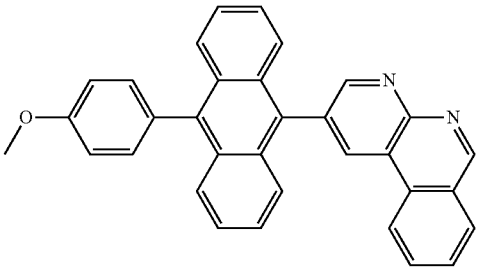
1-45
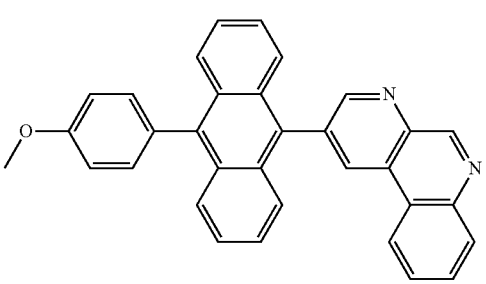
1-46
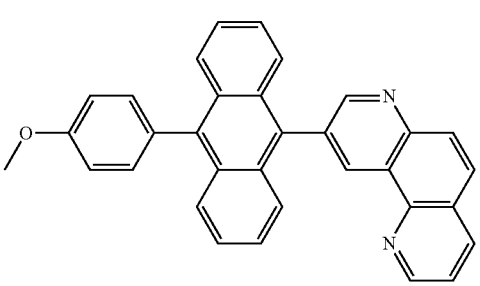

1-47
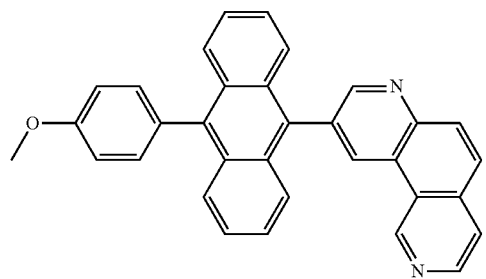
1-48
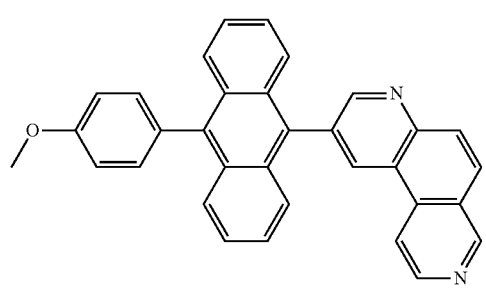
1-49
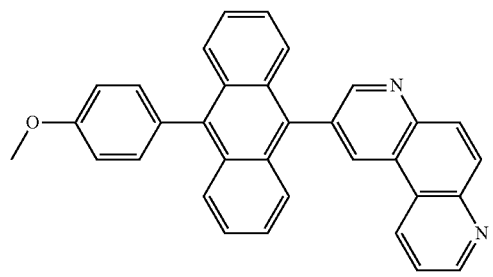
1-50
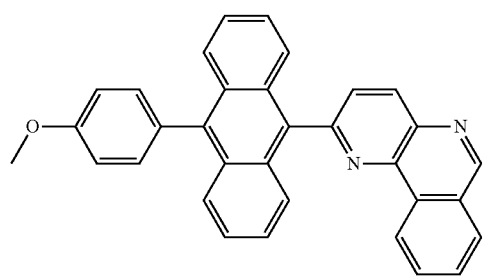
1-51
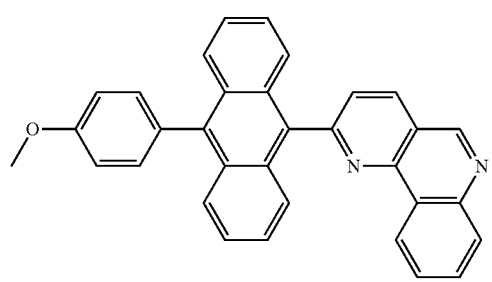
1-52
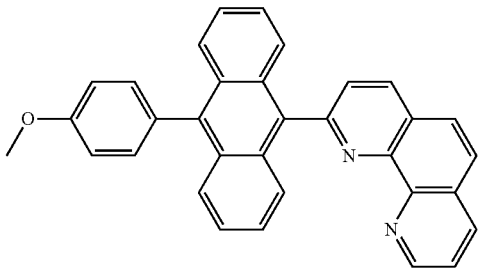
1-53
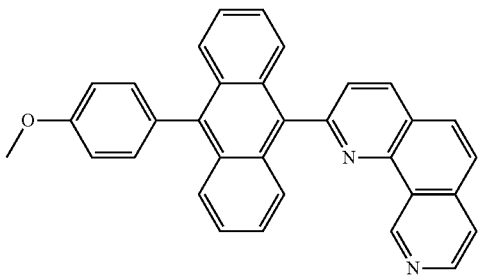
1-54
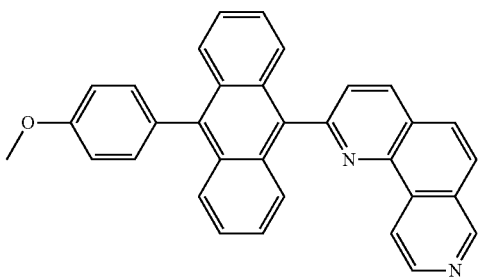
1-55
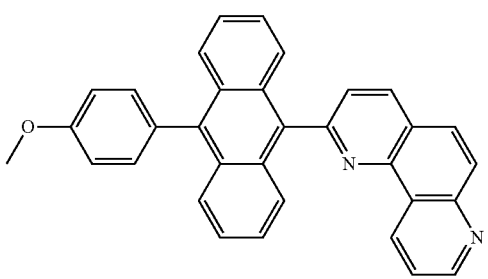
1-56
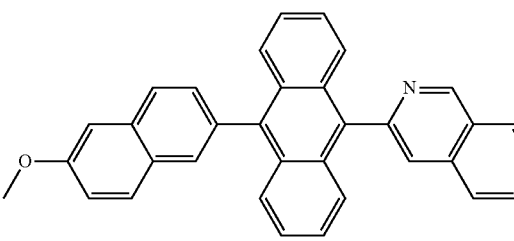
1-57
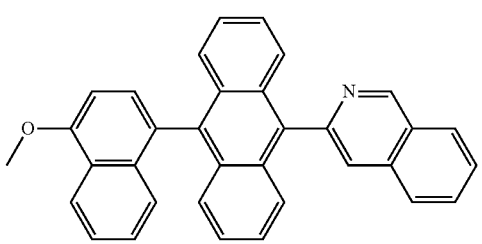

1-58
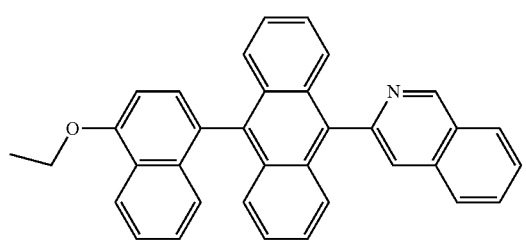
1-59
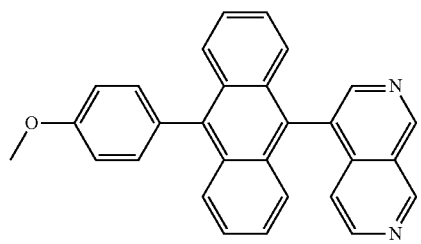
2-1
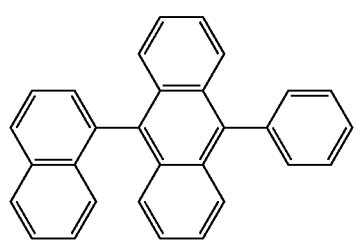
2-2
2-3
2-4
2-5
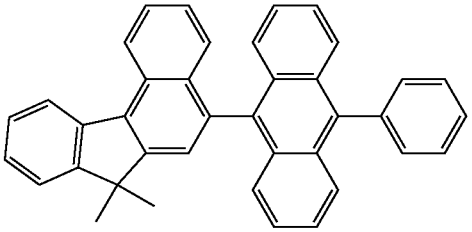
2-6
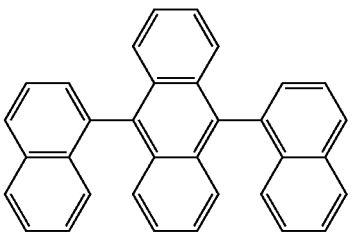
2-7
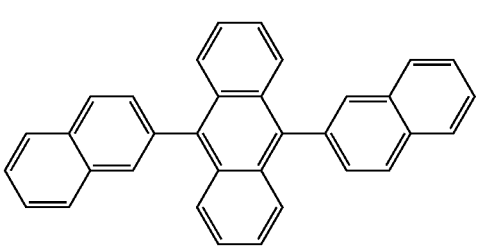
2-8
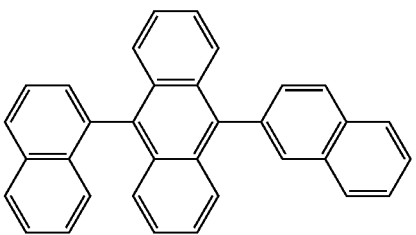
2-9
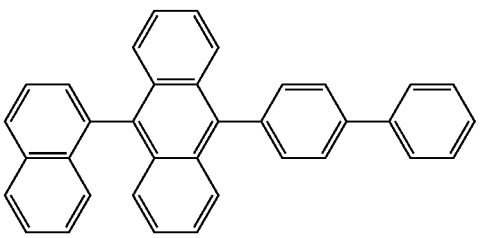
2-10
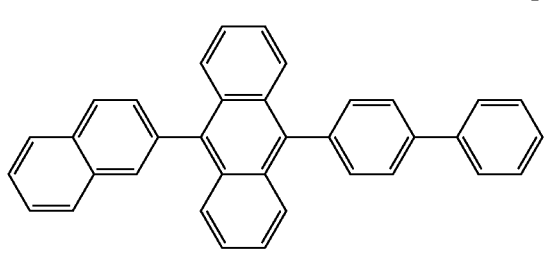

2-11
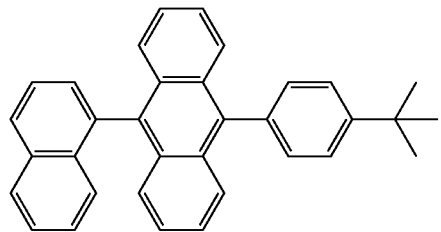
2-12
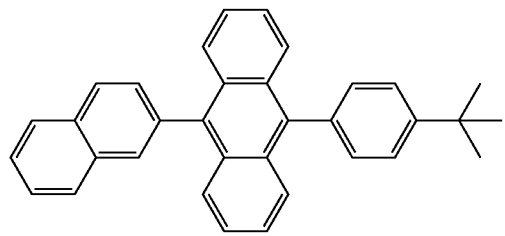
2-13
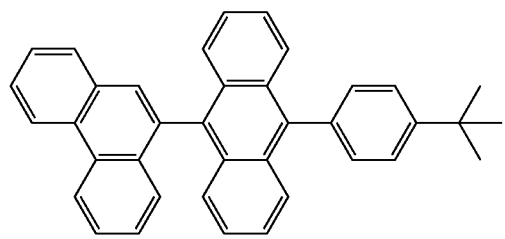
2-14
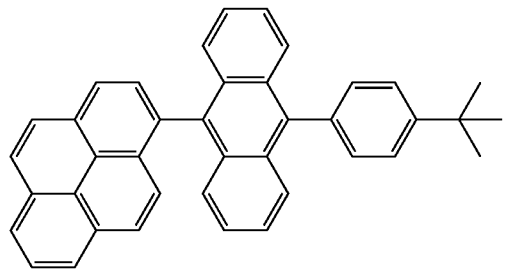
2-15
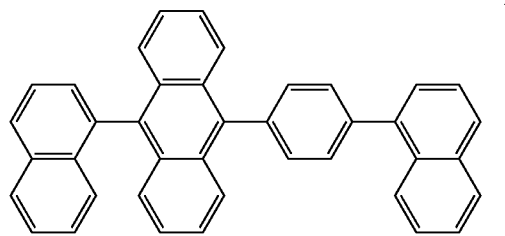
2-16
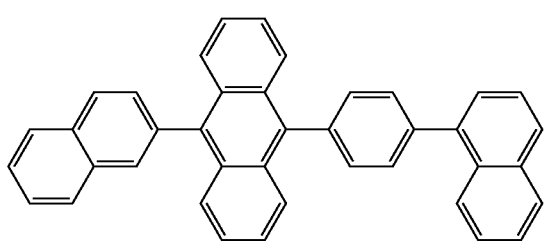
2-17
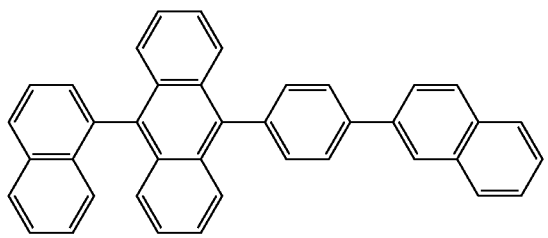
2-18
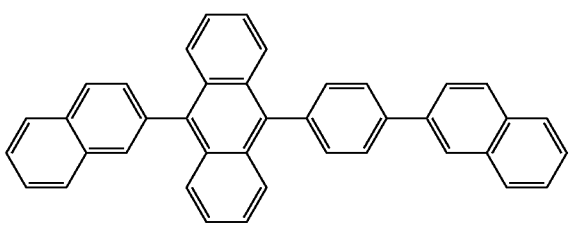
2-19
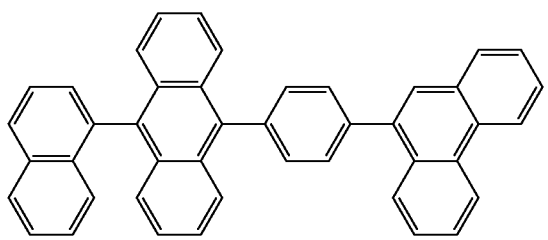
2-20
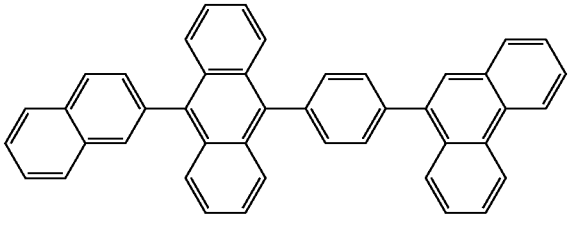
2-21
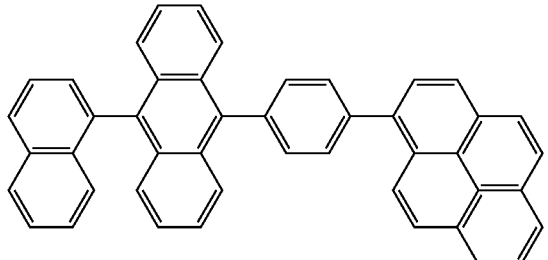
2-22
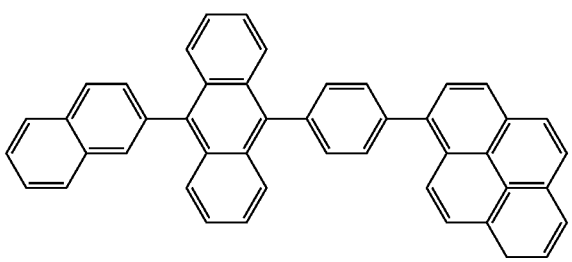

-continued
2-23
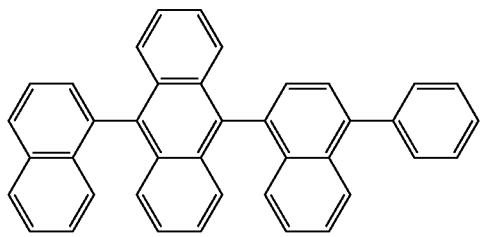
2-24
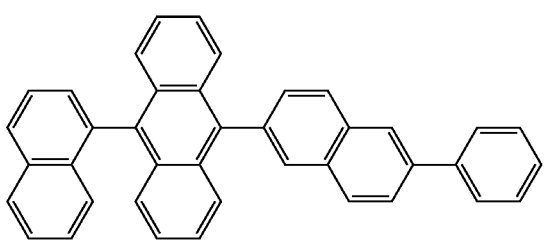
2-25
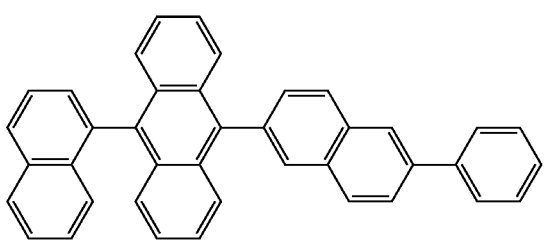
2-26
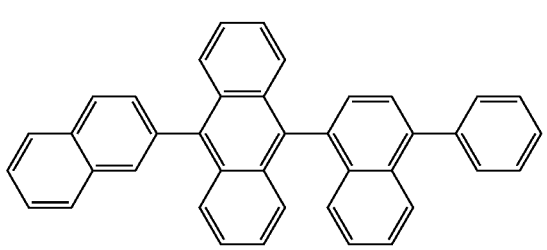
2-27
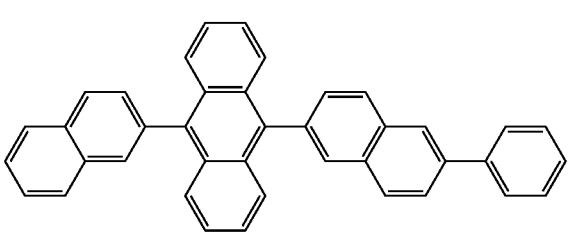
2-28
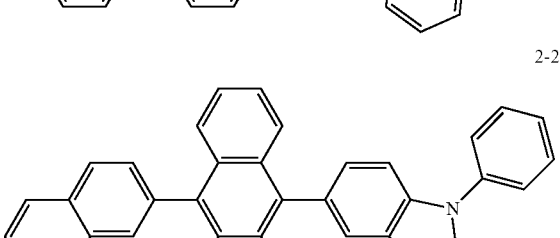
-continued
2-29
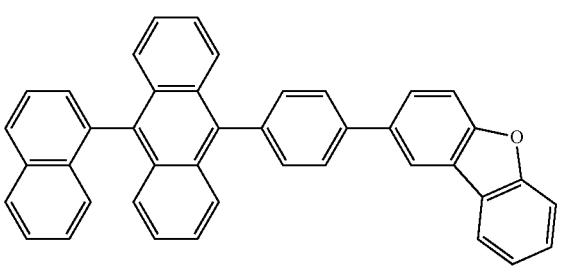
2-30
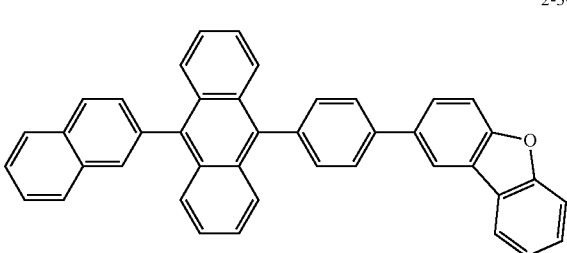
2-31
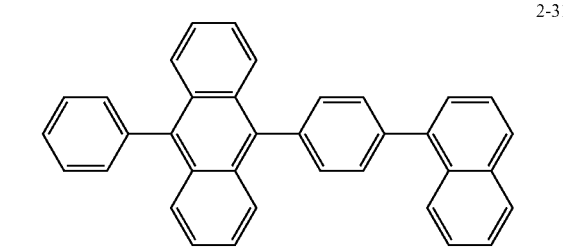
2-32
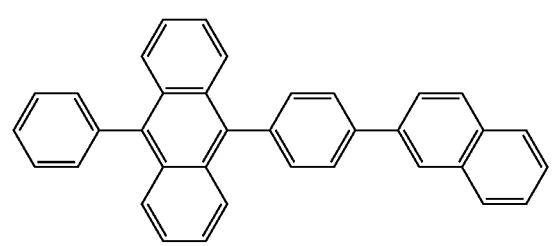
2-33
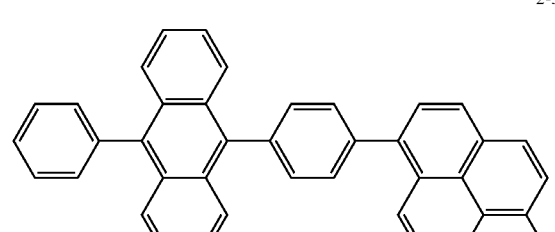
2-34
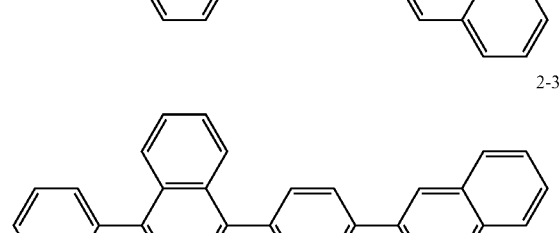

2-35
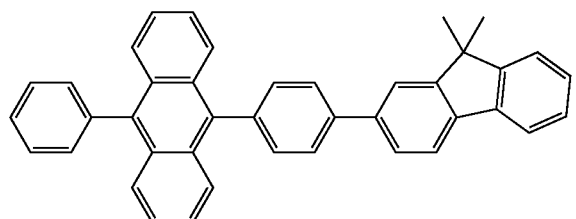
2-36
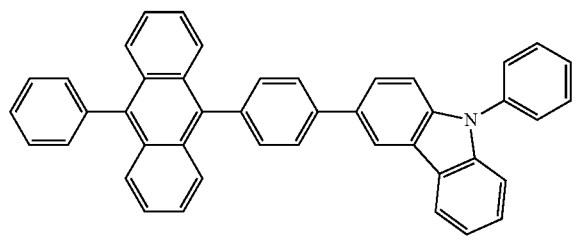
2-37
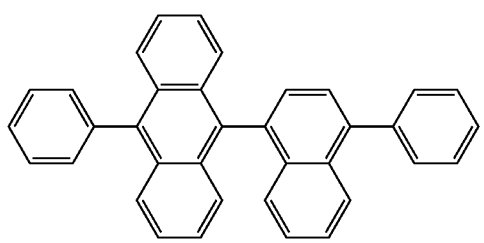
2-38
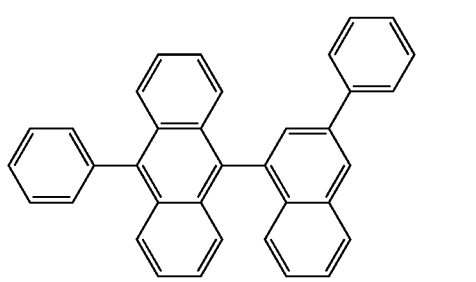
2-39
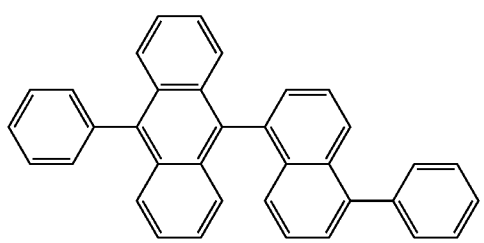
2-40
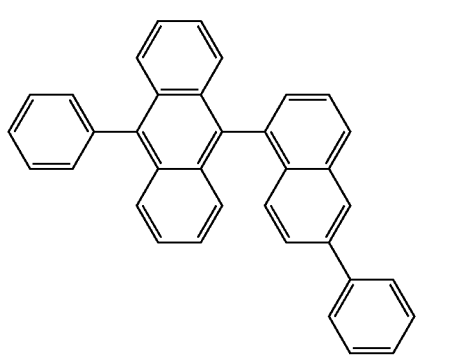
2-41
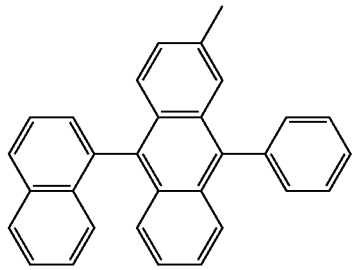
2-42
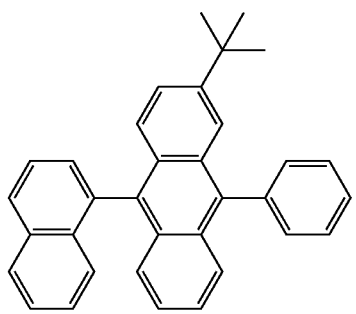
2-43
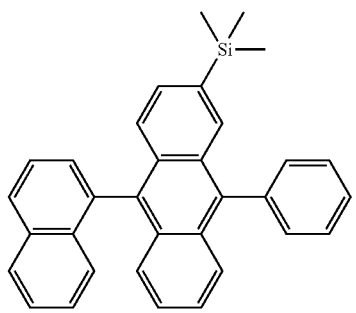
2-44
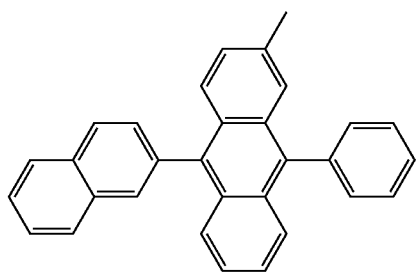
2-45
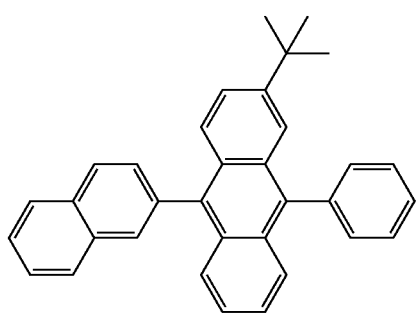

2-46 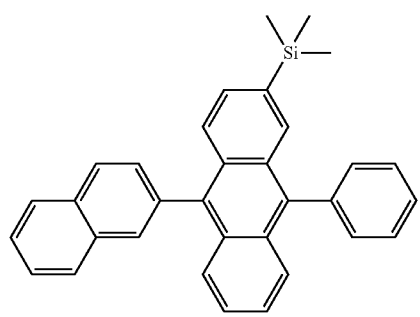
2-47 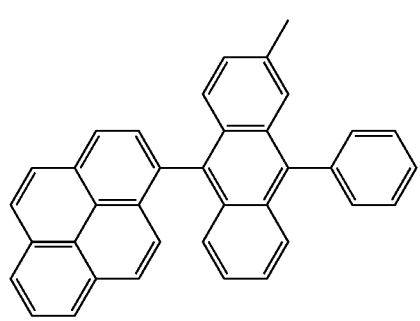
2-48 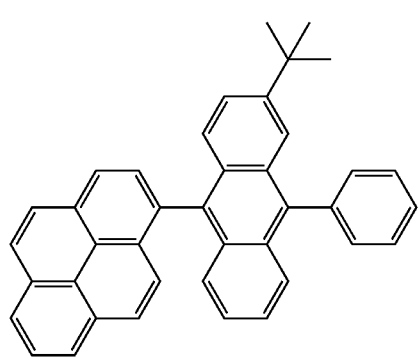
2-49 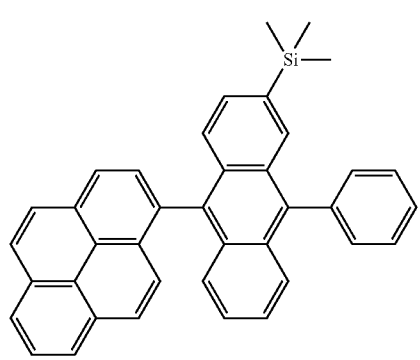
2-50 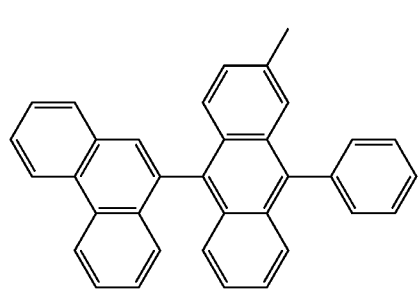
2-51 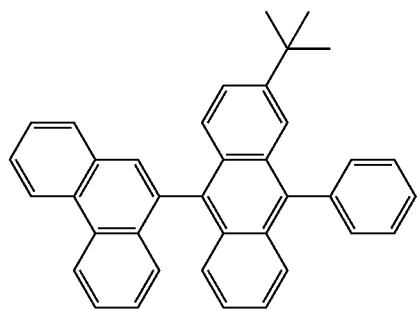
2-52 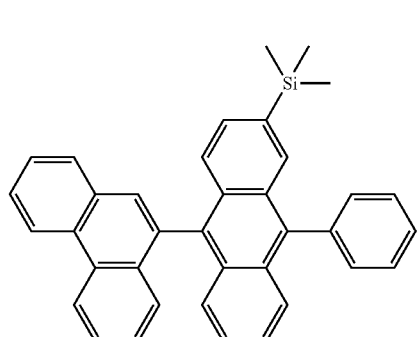
2-53 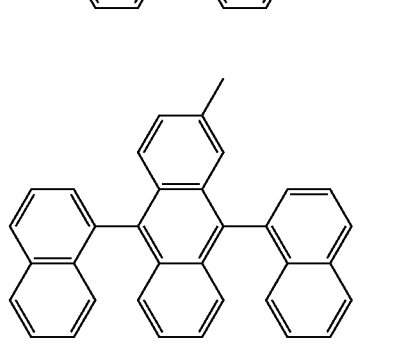
2-54 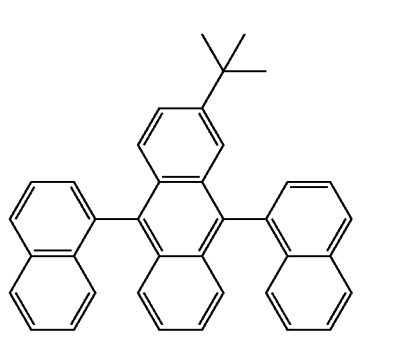
2-55 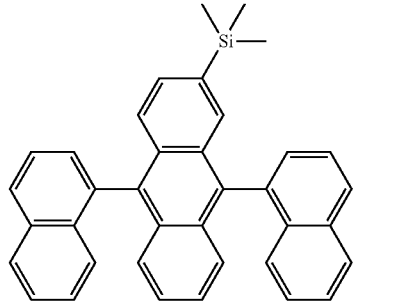

-continued
2-56
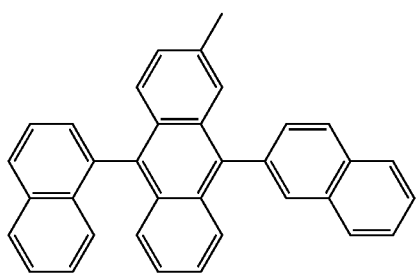
2-57
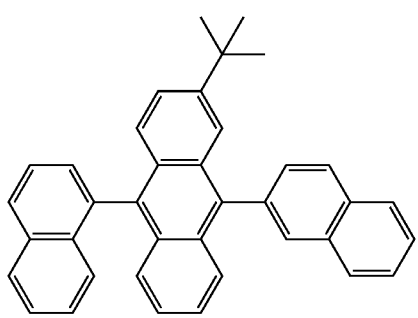
2-58
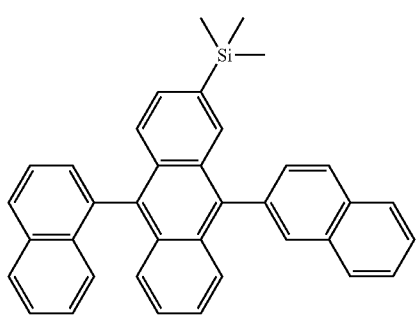
2-59
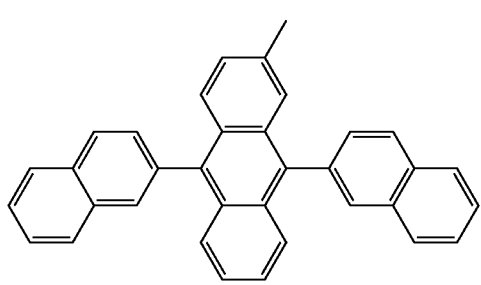
2-60
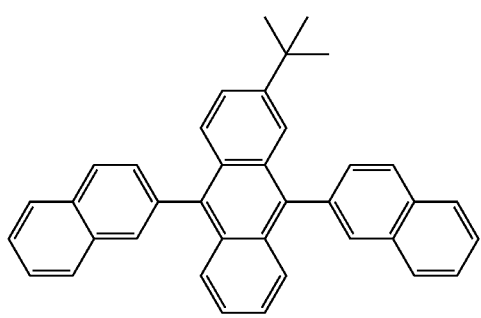
-continued
2-61
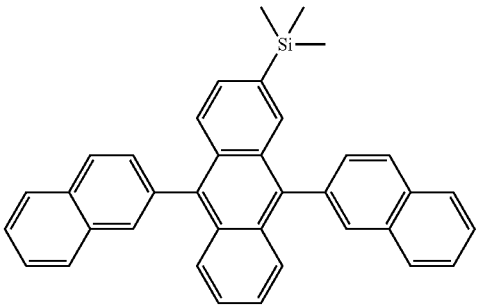
2-62
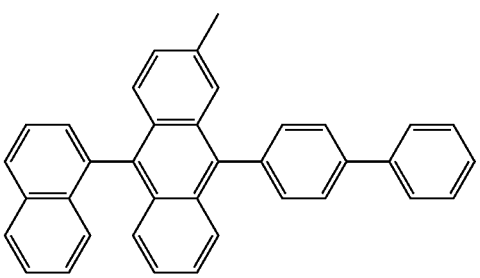
2-63
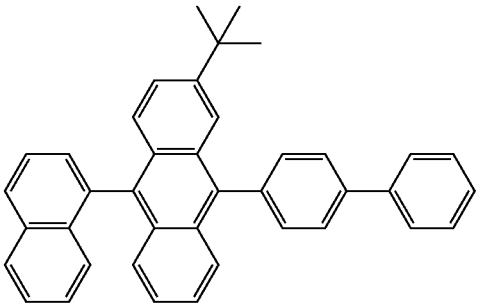
2-64
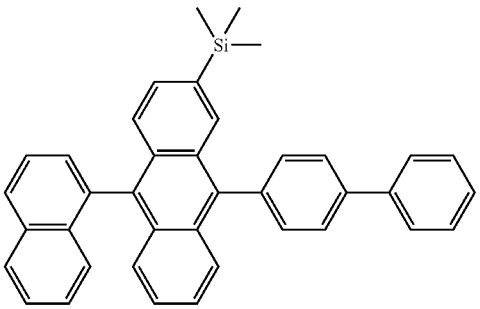
2-65
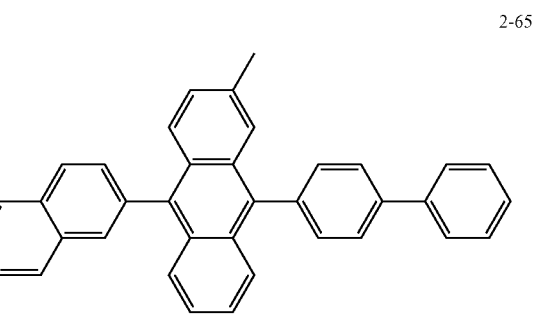

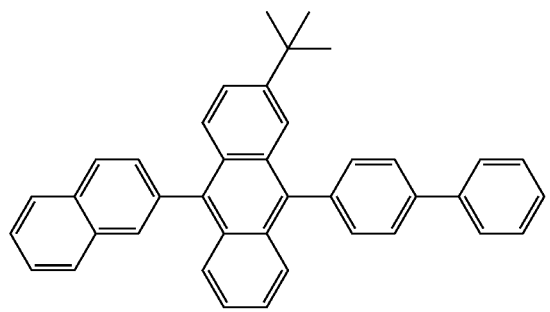
2-66
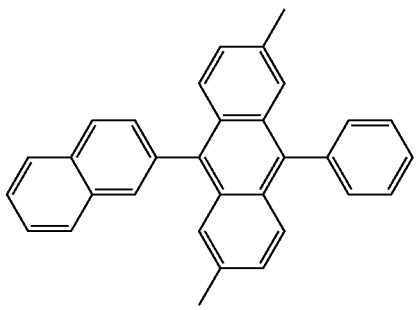
2-70
2-67
2-71
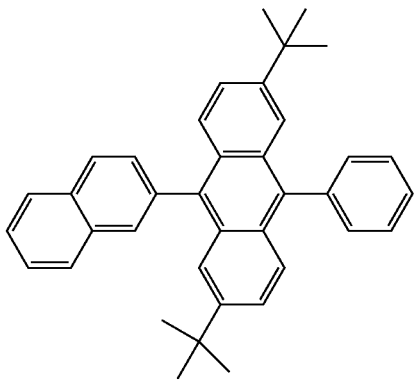
2-68
2-72
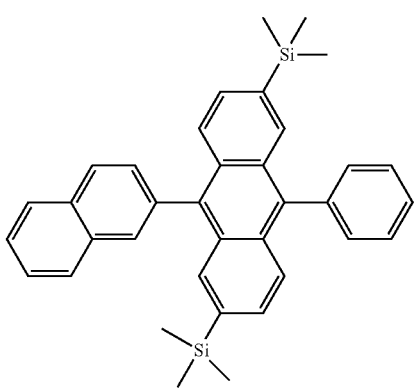
2-69
2-73
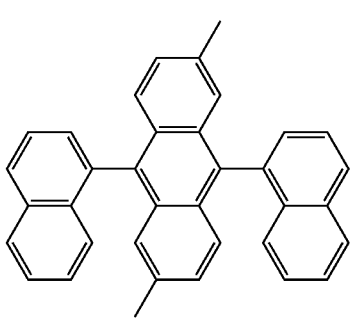

2-74
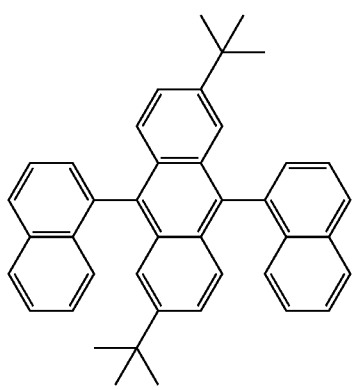
2-78
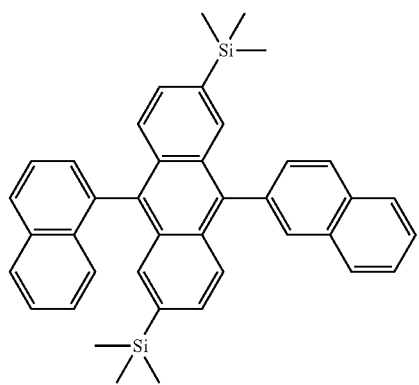
2-75
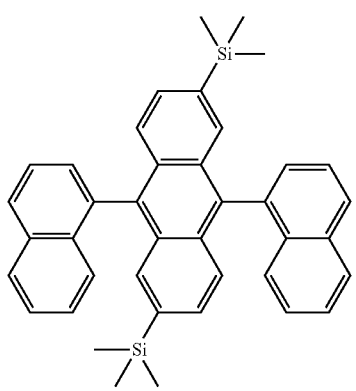
2-79
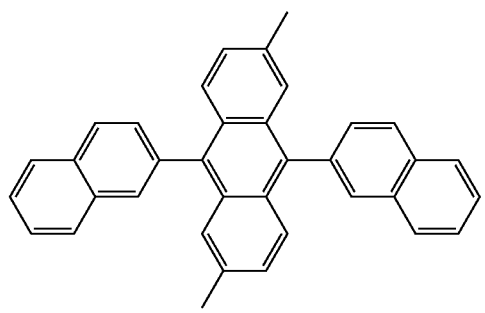
2-76
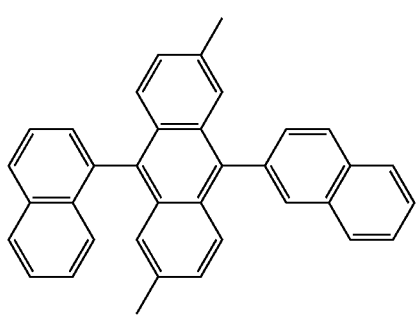
2-80
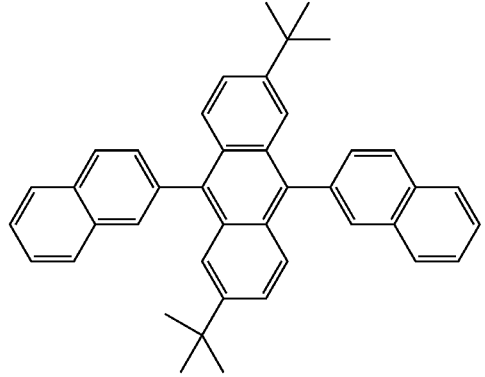
2-77
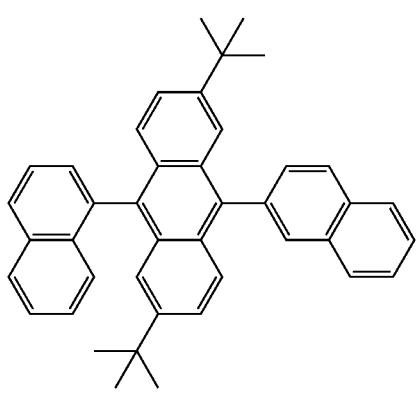
2-81
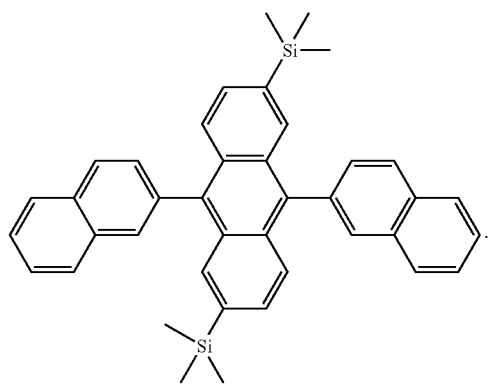
The organic layer of the organic light-emitting device may include the first compound and the second compound to thereby realize a blue organic light-emitting device exhibiting high efficiency and a long lifespan. In particular, the alkoxy group in the first compound may contribute to a blue organic light-emitting device exhibiting high color coordination characteristics.

The organic layer may include i) a hole transport region between the first electrode (anode) and the emission layer, the hole transport region including at least one selected from a hole injection layer, a hole transport layer, a buffer layer, and an electron blocking layer and ii) an electron transport region between the emission layer and the second electrode (cathode), the electron transport region including at least one selected from a hole blocking layer, an electron transport layer, and an electron injection layer.

As used herein, the term "organic layer" may refer to a single layer and/or a plurality of layers between the first electrode and the second electrode in an organic light-emitting device. The material included in the "organic layer" is not limited to being an organic material.

FIG. 1 is a schematic view illustrating the structure of an organic light-emitting device 10 according to an embodiment of the present disclosure. The organic light-emitting device 10 may include a first electrode 110, an organic layer 150, and a second electrode 190.

Hereinafter, the structure of an organic light-emitting device according to an embodiment of the present disclosure and a method of manufacturing an organic light-emitting device according to an embodiment of the present disclosure will be described in connection with FIG. 1.

In FIG. 1, a substrate may be under the first electrode 110 or on the second electrode 190. The substrate may be a glass substrate or a transparent plastic substrate, each having excellent mechanical strength, thermal stability, transparency, surface smoothness, ease of handling, and/or water resistance.

The first electrode 110 may be formed by depositing and/or sputtering a material for forming the first electrode 110 on the substrate. When the first electrode 110 is an anode, the material for the first electrode 110 may be selected from materials with a high work function to facilitate hole injection. The first electrode 110 may be a reflective electrode, a semi-transmissive electrode, or a transmissive electrode. The material for the first electrode 110 may be a transparent and/or highly conductive material. Non-limiting examples of such a material may include indium tin oxide (ITO), indium zinc oxide (IZO), tin oxide ($SnO_2$), and zinc oxide (ZnO). When the first electrode 110 is a semi-transmissive electrode or a reflective electrode, at least one selected from magnesium (Mg), aluminum (Al), aluminum-lithium (Al—Li), calcium (Ca), magnesium-indium (Mg—In), and magnesium-silver (Mg—Ag) may be used as a material for the first electrode 110.

The first electrode 110 may have a single-layer structure or a multi-layer structure including a plurality of layers. For example, the first electrode 110 may have a triple-layer structure of ITO/Ag/ITO, but embodiments of the present disclosure are not limited thereto.

The organic layer 150 may be on the first electrode 110. The organic layer 150 may include an emission layer.

The organic layer 150 may further include a hole transport region between the first electrode and the emission layer and an electron transport region between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL), but embodiments of the present disclosure are not limited thereto.

The hole transport region may have a single-layered structure including a single material, a single-layered structure including a plurality of different materials, or a multi-layered structure having a plurality of layers including a plurality of different materials.

For example, the hole transport region may have a single-layered structure formed of a plurality of different materials, a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked on the first electrode 110 in each stated order, but embodiments of the present disclosure are not limited thereto.

When the hole transport region includes a hole injection layer, the hole injection layer may be formed on the first electrode 110 using one or more suitable methods, e.g., vacuum deposition, spin coating, casting, a Langmuir-Blodgett (LB) method, ink-jet printing, laser printing, and/or laser-induced thermal imaging (LITI).

When the hole injection layer is formed by vacuum deposition, the vacuum deposition may be performed at a temperature of about 100° C. to about 500° C., at a vacuum degree of about $10^{-8}$ Torr to about $10^{-3}$ Torr, and at a vacuum deposition rate of about 0.01 Angstroms per second (Å/sec) to about 100 Å/sec, depending on the compound to be deposited in the hole injection layer, and the structure of the hole injection layer to be formed.

When a hole injection layer is formed by spin coating, the spin coating may be performed at a coating rate of about 2,000 revolutions per minute (rpm) to about 5,000 rpm, and at a temperature of about 80° C. to about 200° C., depending on the compound to be deposited in the hole injection layer, and the structure of a hole injection layer to be formed.

When the hole transport region includes a hole transport layer, the hole transport layer may be formed on the first electrode 110 or on the hole injection layer using one or more suitable methods (such as vacuum deposition, spin coating, casting, an LB method, ink-jet printing, laser printing, and/or LITI). When the hole transport layer is formed by vacuum deposition and/or spin coating, the conditions used for vacuum deposition and coating may be similar to the vacuum deposition and coating conditions used for forming the hole injection layer.

The hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

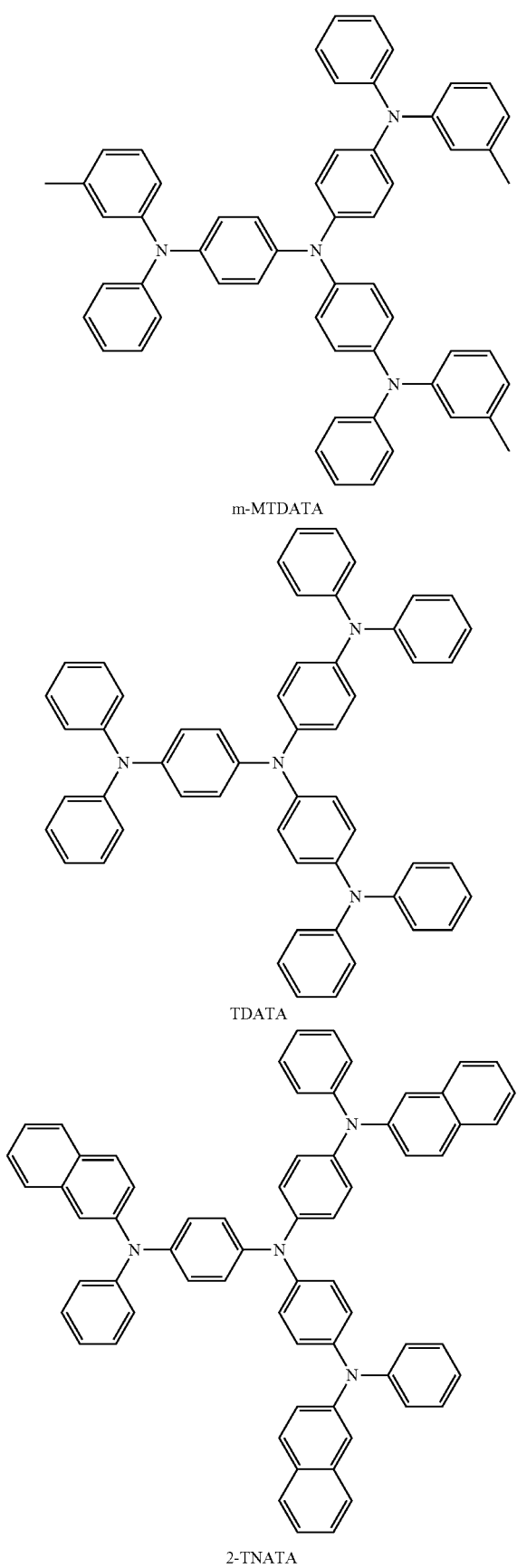
m-MTDATA
TDATA
2-TNATA
-continued
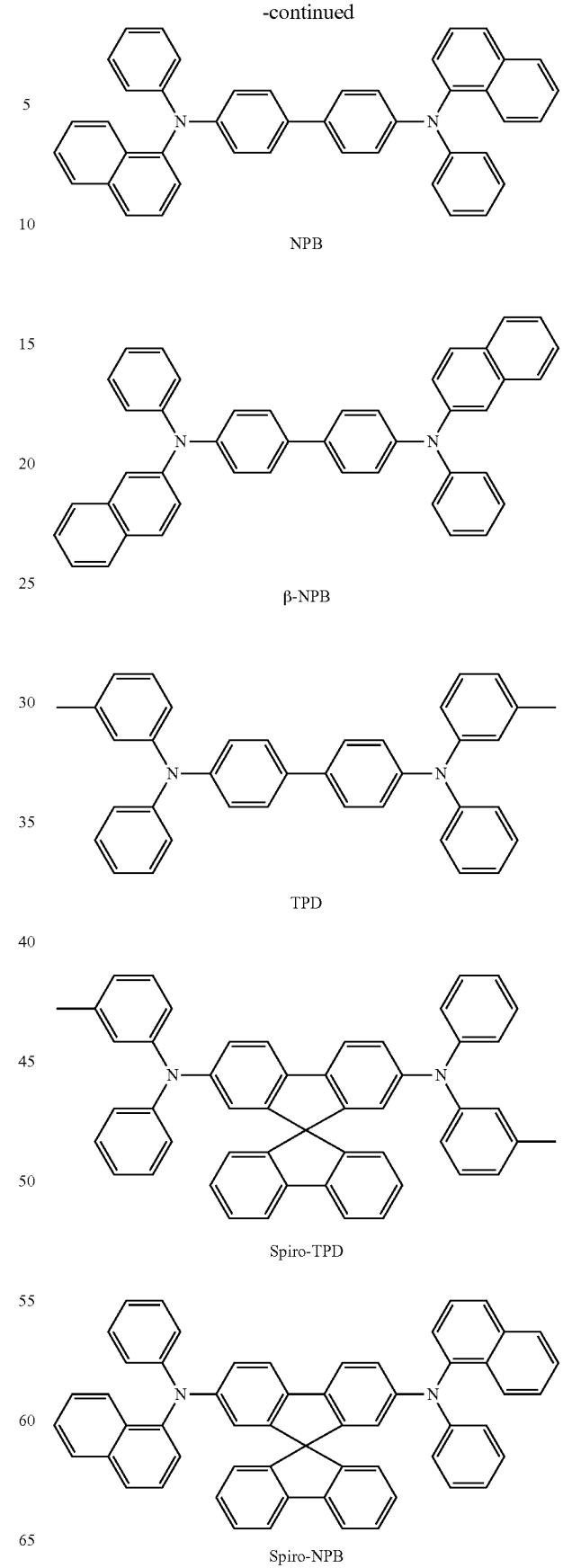
NPB
β-NPB
TPD
Spiro-TPD
Spiro-NPB

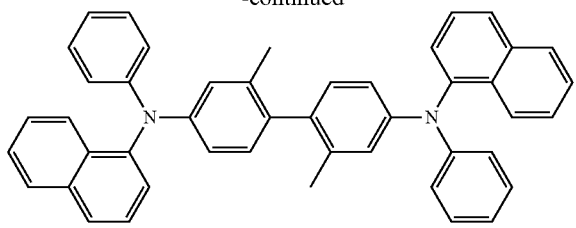

methylated NPB

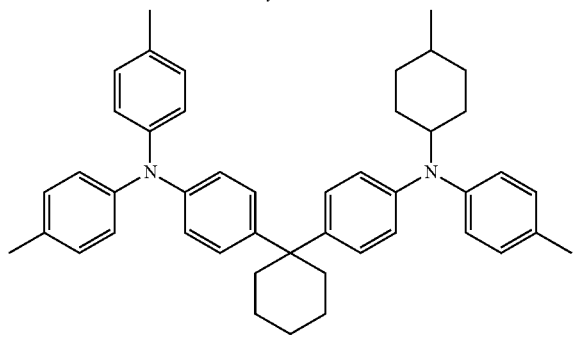

TAPC

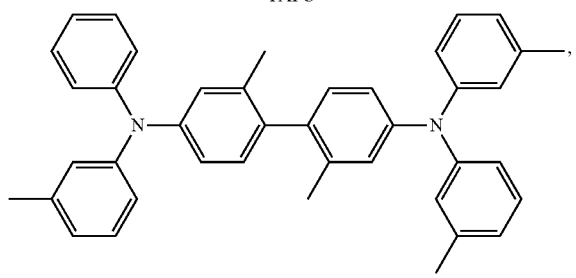

HMTPD

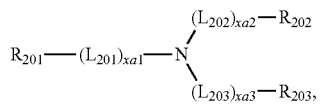

Formula 201

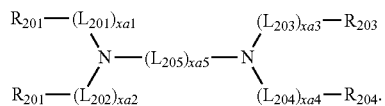

Formula 202

In Formulae 201 and 202, $L_{201}$ to $L_{205}$ may each be the same as described herein in connection with $L_1$, xa1 to xa4 may each independently be selected from 0, 1, 2, and 3, xa5 may be selected from 1, 2, 3, 4, and 5, and $R_{201}$ to $R_{204}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may each independently be selected from the group consisting of:

a phenylene group, a naphthylene group, a fluorenylene group, a spirobifluorenylene group, a benzofluorene group a benzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, a triazinylene group; and a phenylene group, a naphthylene group, a fluorenylene group, a spirobifluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa4 may each independently be selected from 0, 1, and 2, xa5 may be selected from 1, 2, and 3, and $R_{201}$ to $R_{204}$ may each independently be selected from the group consisting of:

a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group; and a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, an azulenyl group, a fluorenyl group, a spirobifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present disclosure are not limited thereto.

The compound represented by Formula 201 may be represented by Formula 201A:

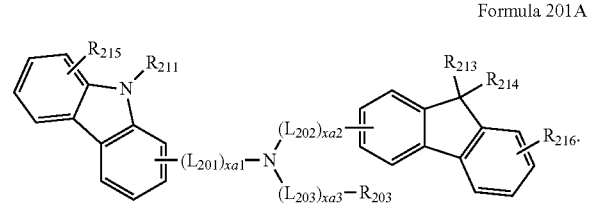

Formula 201A

In some embodiments, the compound represented by Formula 201 may be represented by Formula 201A-1, but embodiments of the present disclosure are not limited thereto:

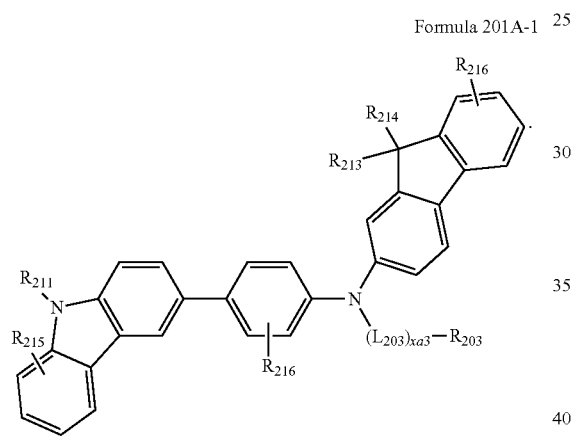

Formula 201A-1

In some embodiments, the compound represented by Formula 202 may be represented by Formula 202A, but embodiments of the present disclosure are not limited thereto:

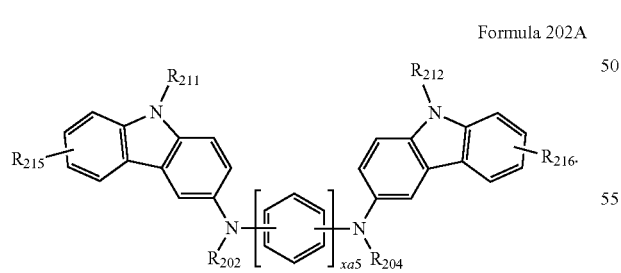

Formula 202A

In Formulae 201A, 201A-1, and 202A, $L_{201}$ to $L_{203}$, xa1 to xa3, xa5, and $R_{202}$ to $R_{204}$ may each be the same as described herein in connection with Formulae 201 and 202. $R_{211}$ and $R_{212}$ may each be the same as described herein in connection with $R_{203}$; and $R_{213}$ to $R_{216}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compound represented by Formula 201 and the compound represented by Formula 202 may be or include at least one selected from Compounds HT1 to HT20, but embodiments of the present disclosure are not limited thereto:

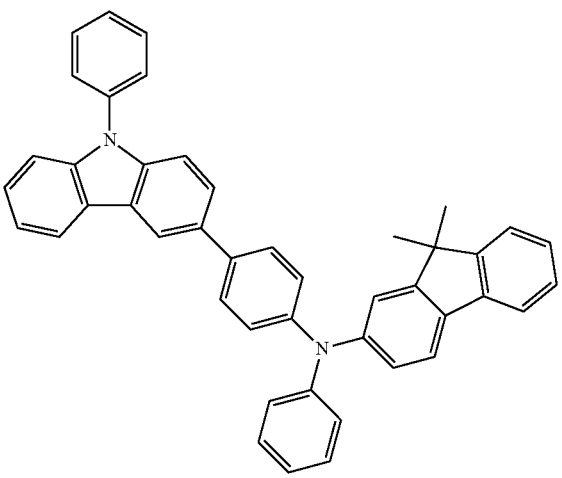

HT1

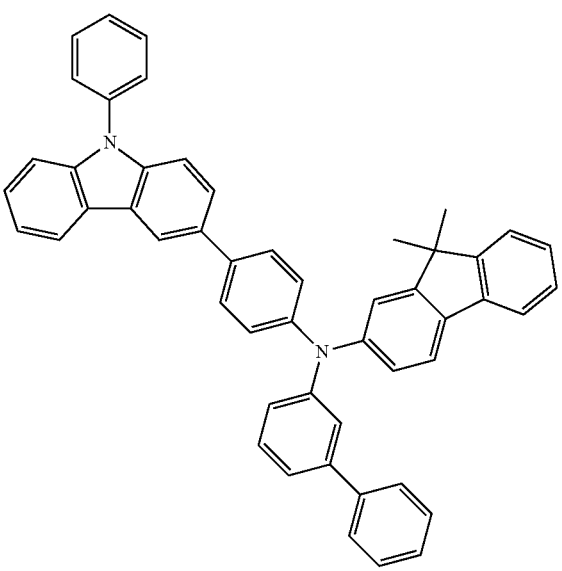

HT2

HT3
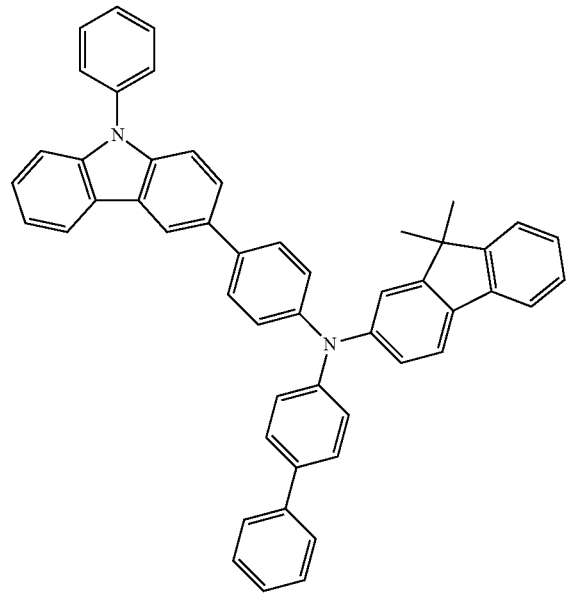
HT5
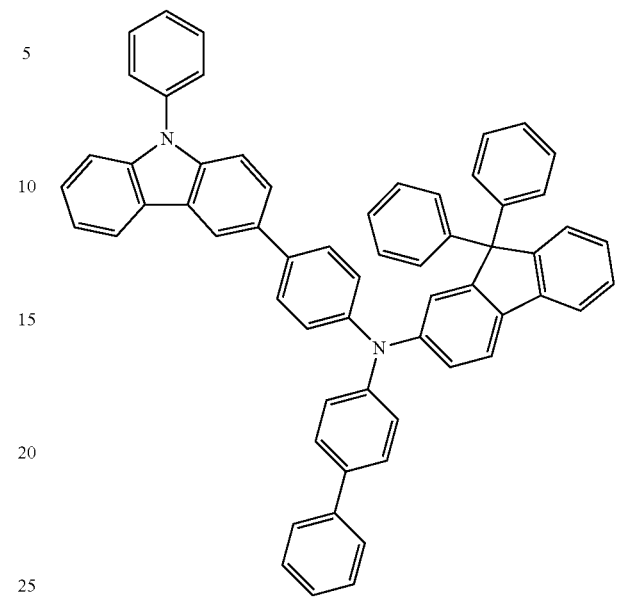
HT4
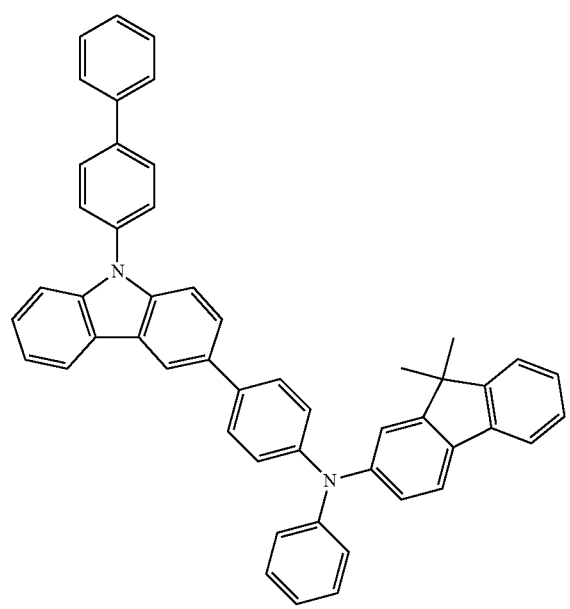
HT6
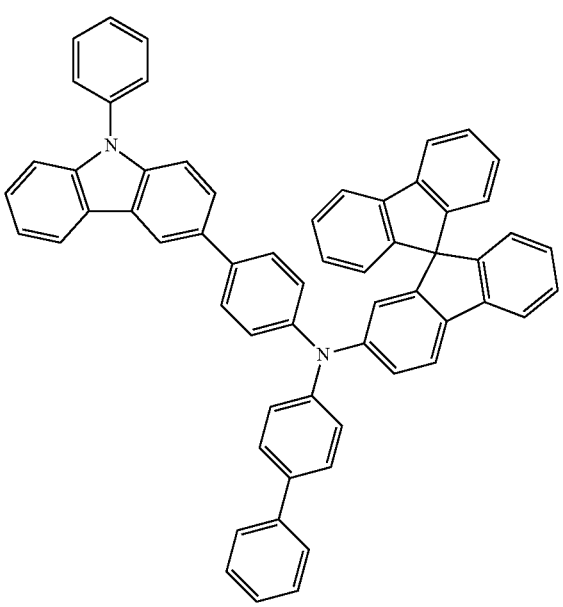

HT7
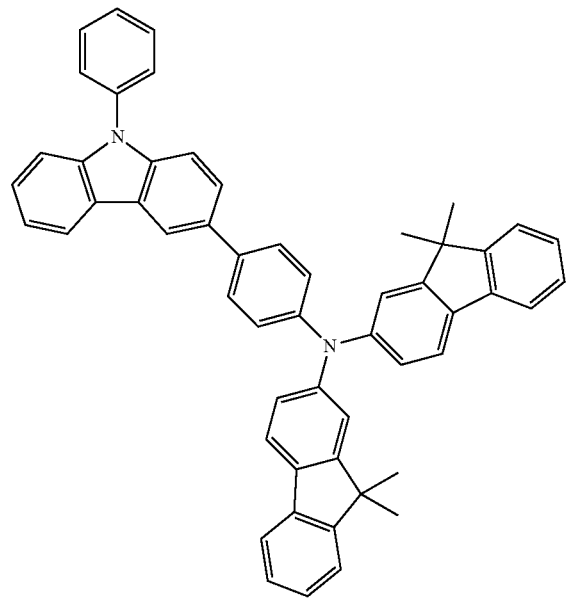
HT9
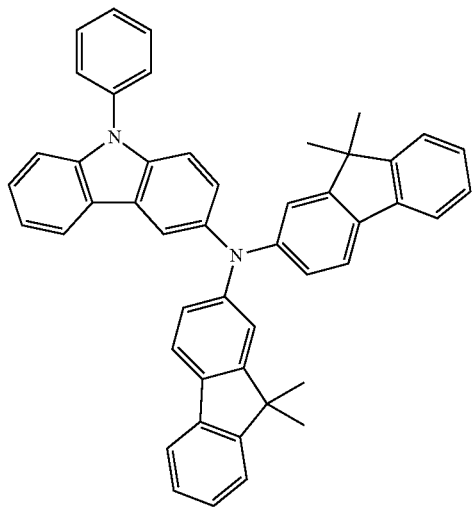
HT8
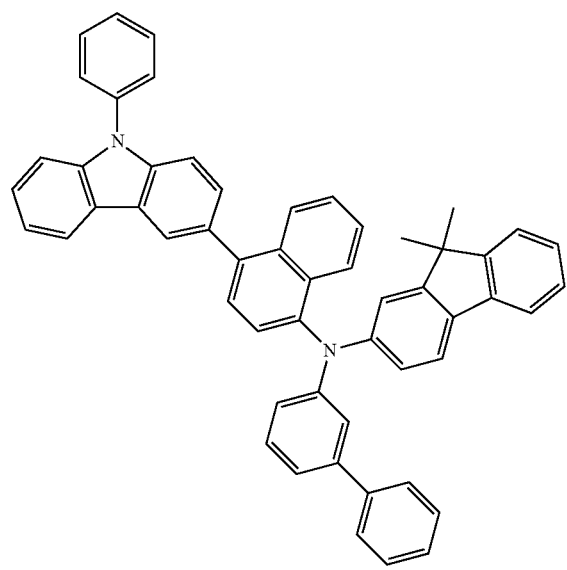
HT10
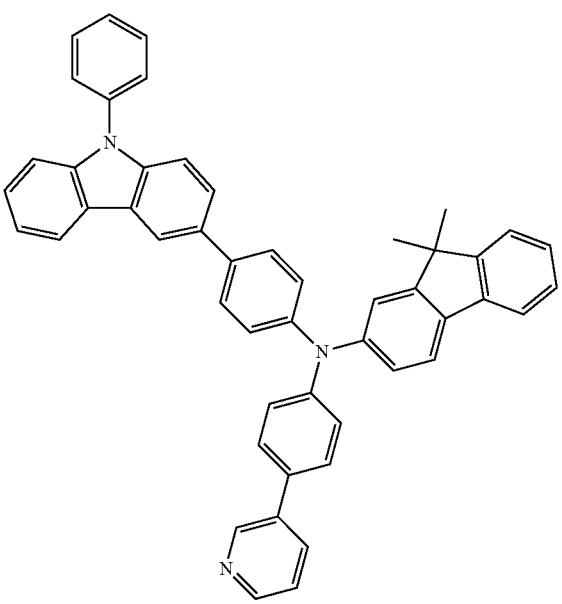

HT11
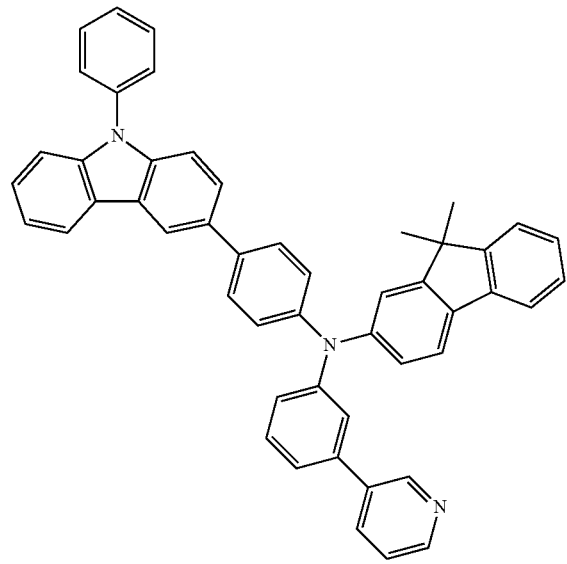
HT14
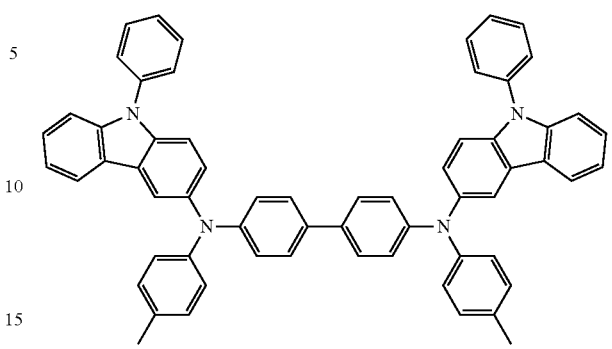
HT15
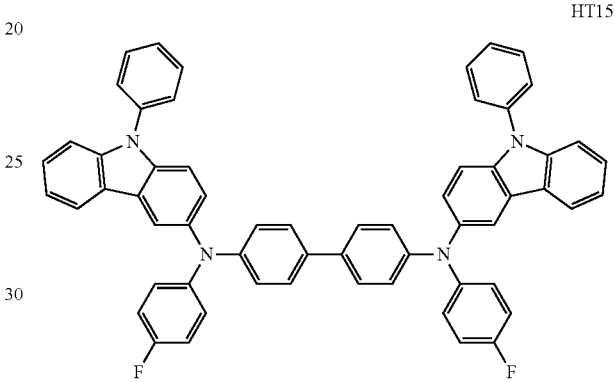
HT12
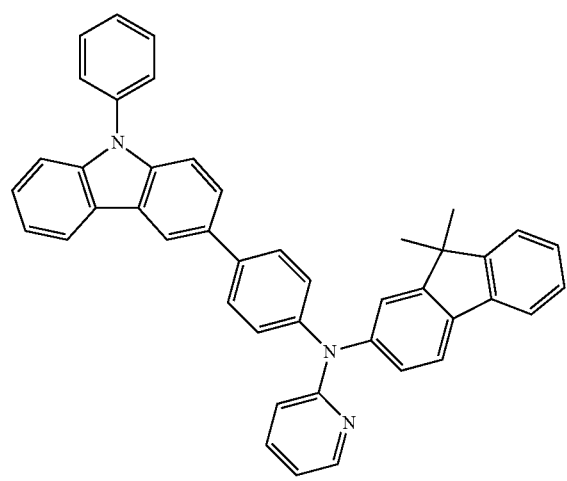
HT16
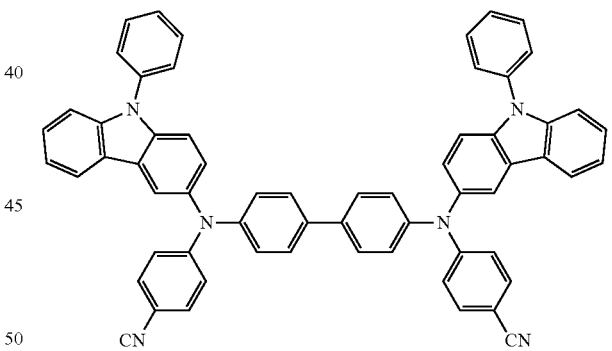
HT13
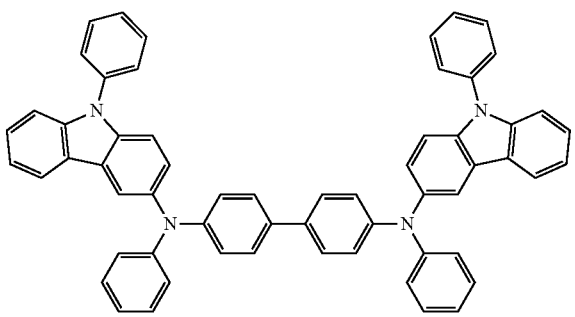
HT17
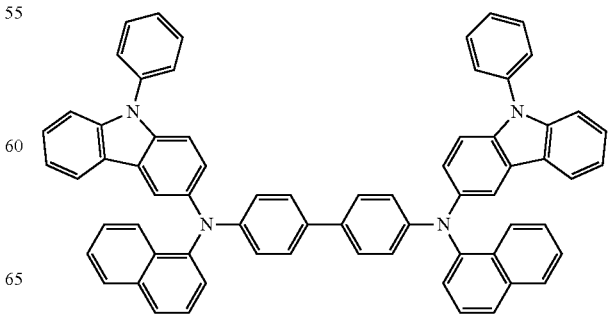

-continued

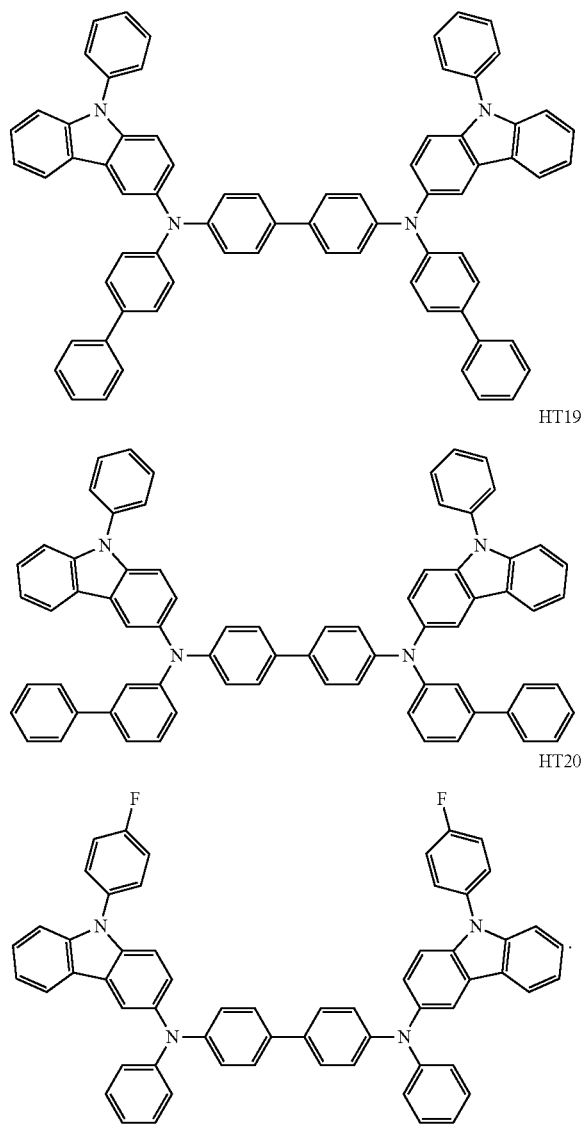

HT18

HT19

HT20

The thickness of the hole transport region may be about 100 Å to about 10,000 Å, and in some embodiments, about 100 Å to about 1,000 Å. When the hole transport region includes a hole injection layer and a hole transport layer, the thickness of the hole injection layer may be about 100 Å to about 10,000 Å, and in some embodiments, about 100 Å to about 1,000 Å. The thickness of the hole transport layer may be about 50 Å to about 2,000 Å, and in some embodiments, about 100 Å to about 1,500 Å. When the thicknesses of the hole transport region, the hole injection layer, and the hole transport layer are each within these ranges, excellent hole transport characteristics may be obtained without a substantial increase in driving voltage.

The hole transport region may include a charge-generating material to improve conductive properties. The charge-generating material may be homogeneously or non-homogeneously dispersed throughout the hole transport region.

The charge-generating material may be, for example, a p-dopant. The p-dopant may be selected from a quinone derivative, a metal oxide, and a cyano group-containing compound, but embodiments of the present disclosure are not limited thereto. Non-limiting examples of the p-dopant may include quinone derivatives (such as tetracyanoquinonedimethane (TCNQ) and/or 2,3,5,6-tetrafluoro-tetracyano-1,4-benzoquinonedimethane (F4-TCNQ)); metal oxides (such as a tungsten oxide and/or a molybdenum oxide); and Compound HT-D1, but embodiments of the present disclosure are not limited thereto:

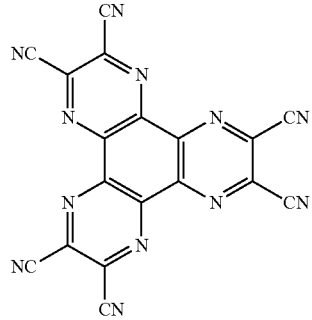

Compound HT-D1

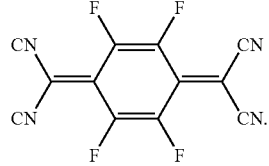

F4-TCNQ

The hole transport region may further include, in addition to the hole injection layer and the hole transport layer, at least one selected from a buffer layer and an electron blocking layer. Since the buffer layer may compensate for an optical resonance distance according to a wavelength of light emitted from the emission layer (e.g., be used to adjust the optical resonance distance to match the wavelength of light emitted from the emission layer), the light-emission efficiency of the resulting organic light-emitting device may be improved. Materials included in the hole transport region may also be included in the buffer layer. In some embodiments, the electron blocking layer may prevent or reduce injection of electrons from the electron transport region.

An emission layer may be formed on the first electrode 110 or on the hole transport region using one or more suitable methods (such as vacuum deposition, spin coating, casting, an LB method, ink-jet printing, laser printing, and/or LITI). When the emission layer is formed by vacuum deposition and/or spin coating, the deposition and coating conditions used for the emission layer may be similar to the deposition and coating conditions used for the hole injection layer.

When the organic light-emitting device 10 is a full color organic light-emitting device, the emission layer may be patterned into a red emission layer, a green emission layer, or a blue emission layer, according to a sub-pixel. In some embodiments, the emission layer may have a stacked structure of a red emission layer, a green emission layer, and a blue emission layer, or may include a red-light emission material, a green-light emission material, and a blue-light emission material, which may be mixed with each other in a single layer to thereby emit white light.

The emission layer may include a host and a dopant.

The host may include the second compound, and the dopant may include the first compound.

The amount of the dopant in the emission layer may be, in general, about 0.01 part by weight to about 15 parts by weight based on 100 parts by weight of the host, but embodiments of the present disclosure are not limited thereto.

The thickness of the emission layer may be about 1 nm to about 400 nm, and in some embodiments, about 10 nm to about 100 nm. When the thickness of the emission layer is within these ranges, excellent light-emission characteristics may be achieved without a substantial increase in driving voltage.

An electron transport region may be on the emission layer.

The electron transport region may include at least one selected from a hole blocking layer, an electron transport layer (ETL), and an electron injection layer, but embodiments of the present disclosure are not limited thereto.

In some embodiments, the electron transport region may have a structure of electron transport layer/electron injection layer or a structure of hole blocking layer/electron transport layer/electron injection layer, wherein layers of each structure are sequentially stacked on the emission layer in each stated order, but embodiments of the present disclosure are not limited thereto.

In some embodiments, the organic layer 150 of the organic light-emitting device 10 may include an electron transport region between the emission layer and the second electrode 190.

When the electron transport region includes a hole blocking layer, the hole blocking layer may be formed on the emission layer using one or more suitable methods (such as vacuum deposition, spin coating, casting, an LB method, ink-jet printing, laser printing, and/or LITI). When the hole blocking layer is formed by vacuum deposition and/or spin coating, the deposition and coating conditions used for the hole blocking layer may be similar to the deposition and coating conditions used for the hole injection layer.

The hole blocking layer may include, for example, at least one selected from BCP and Bphen, but embodiments of the present disclosure are not limited thereto:

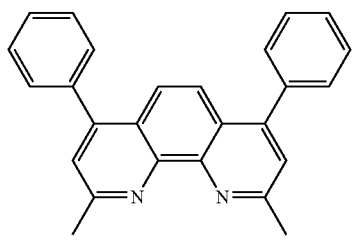

BCP

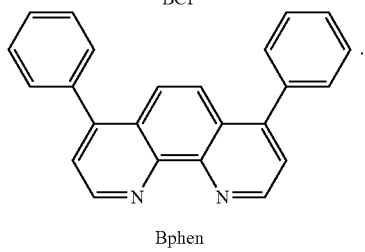

Bphen

The thickness of the hole blocking layer may be about 20 Å to about 1,000 Å, and in some embodiments, about 30 Å to about 300 Å. When the thickness of the hole blocking layer is within these ranges, excellent hole blocking characteristics may be achieved without a substantial increase in driving voltage.

The electron transport region may include an electron transport layer. The electron transport layer may be formed on the emission layer or on the hole blocking layer using one or more suitable methods (such as vacuum deposition, spin coating, casting, an LB method, ink-jet printing, laser printing, and/or LITI). When the electron transport layer is formed using vacuum deposition and/or spin coating, the vacuum deposition and coating conditions used for the electron transport layer may be similar to the vacuum deposition and coating conditions used for the hole injection layer.

In some embodiments, the electron transport layer may include at least one selected from a compound represented by Formula 601 and a compound represented by Formula 602:

$$Ar_{601}\text{-}[(L_{601})_{xe1}\text{-}E_{601}]_{xe2}.$$  Formula 601

In Formula 601, $Ar_{601}$ may be selected from the group consisting of:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group; and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$), wherein $Q_{301}$ to $Q_{303}$ may each independently be selected from hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group, $L_{601}$ may be the same as described herein in connection with $L_{201}$, $E_{601}$ may be selected from the group consisting of:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, xe1 may be selected from 0, 1, 2, and 3, and
xe2 may be selected from 1, 2, 3, and 4.

Formula 602

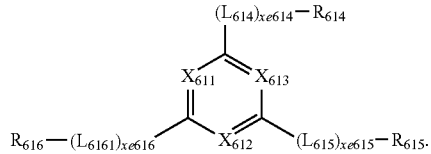

In Formula 602, $X_{611}$ may be selected from N and C-$(L_{611})_{xe611}$-$R_{611}$; $X_{612}$ may be selected from N and C-$(L_{612})_{xe612}$-$R_{612}$; $X_{613}$ may be selected from N and C-$(L_{613})_{xe613}$-$R_{613}$, and at least one selected from $X_{611}$ to $X_{613}$ may be N, $L_{611}$ to $L_{616}$ may each be the same as described herein in connection with $L_1$, $R_{611}$ to $R_{616}$ may each independently be selected from the group consisting of:

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, carbazolyl, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xe611 to xe616 may each independently be selected from 0, 1, 2, and 3.

The compound represented by Formula 601 and the compound represented by Formula 602 may each independently be selected from Compounds ET1 to ET15:

ET1

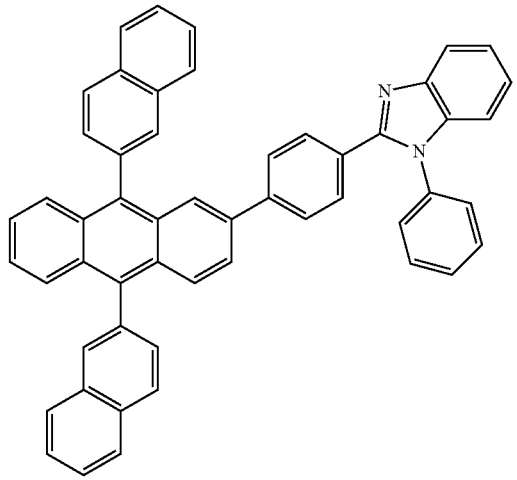

93
-continued
ET2
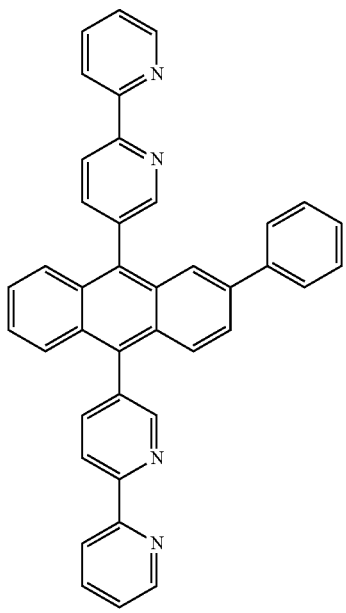
ET3
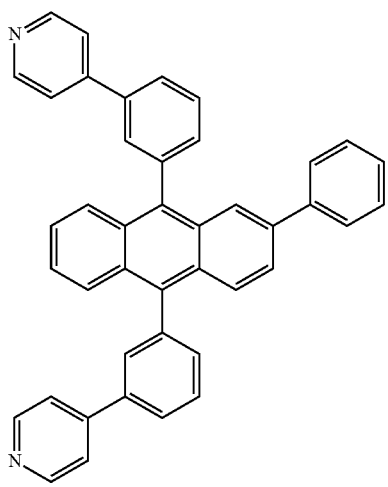
ET4
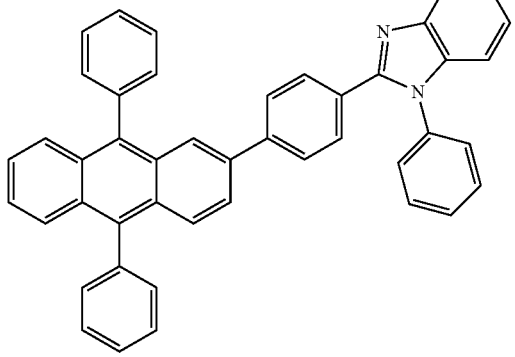
94
-continued
ET5
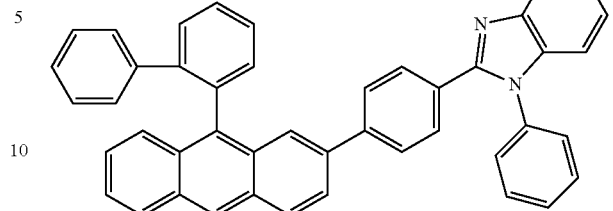
ET6
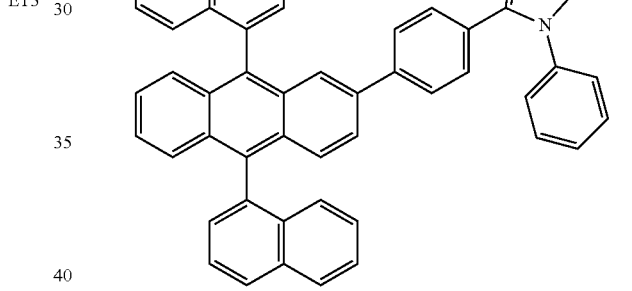
ET7
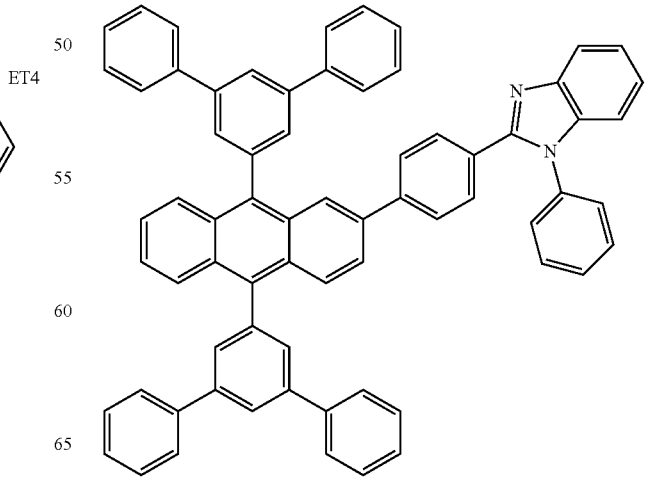

ET8
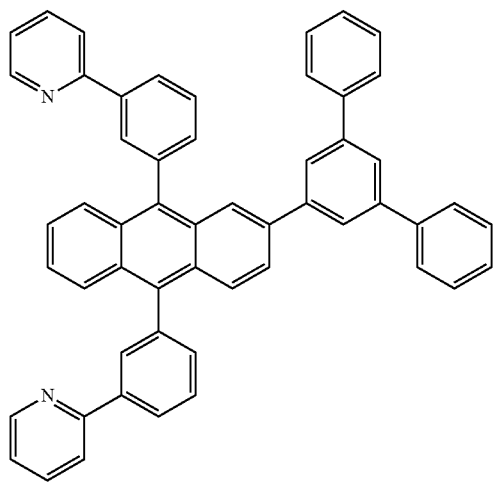
ET10
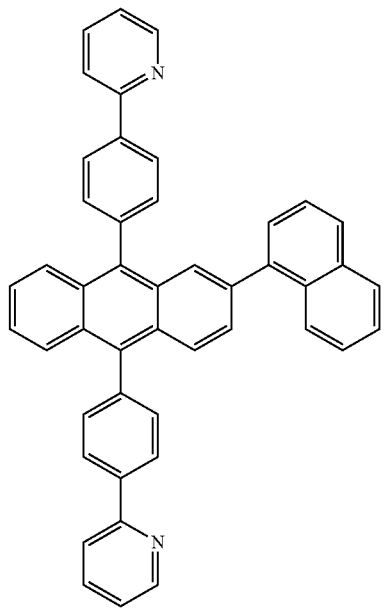
ET11
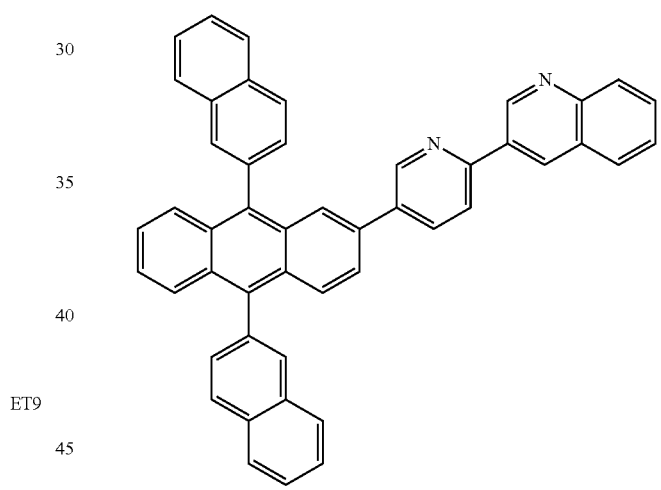
ET9
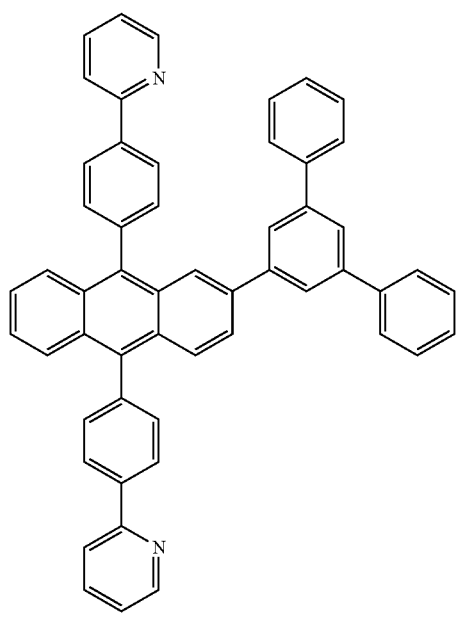
ET12
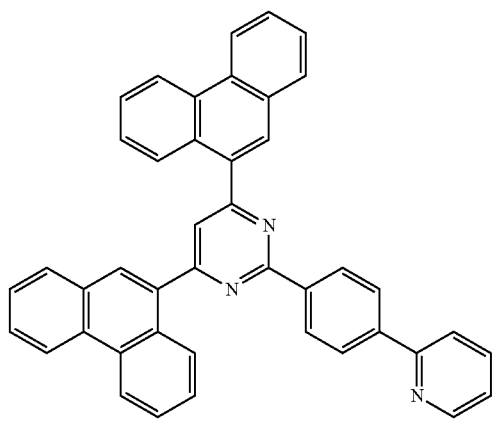

ET13
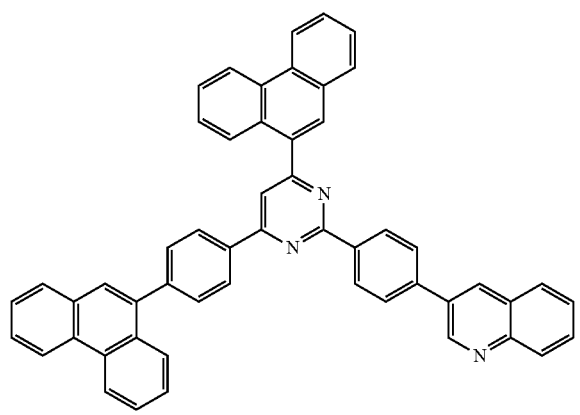
ET14
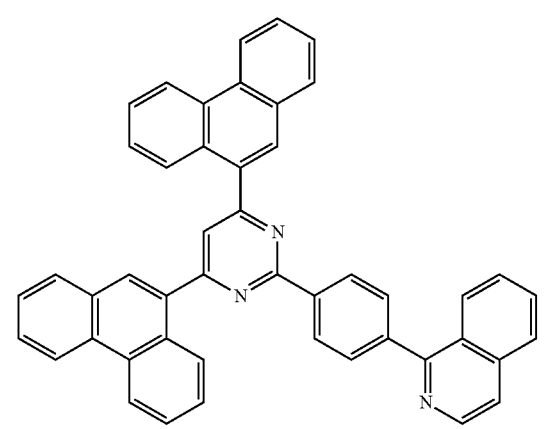
ET15
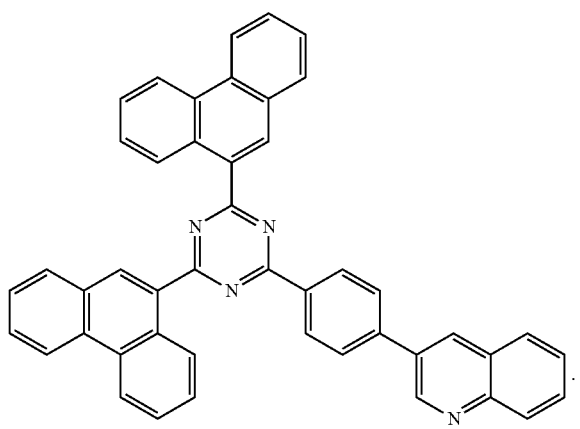
-continued
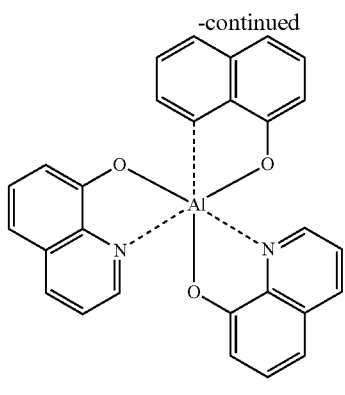
Alq3
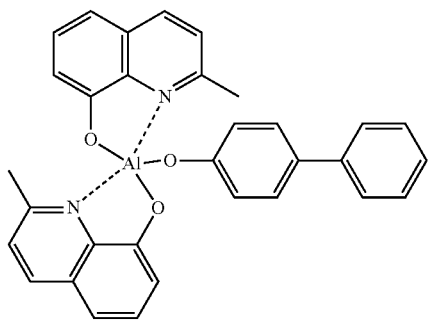
Balq
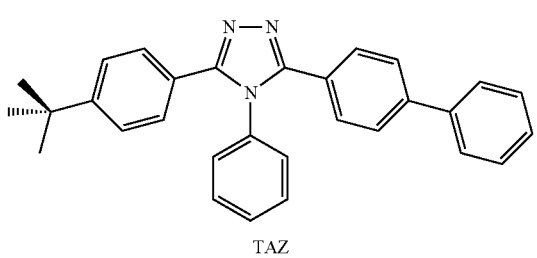
TAZ
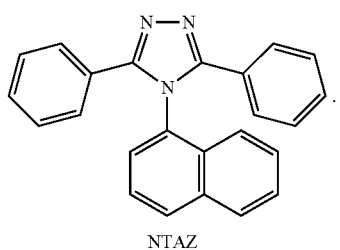
NTAZ
In some embodiments, the electron transport layer may include at least one selected from BCP, Bphen, Alq₃, BAlq, TAZ, and NTAZ:

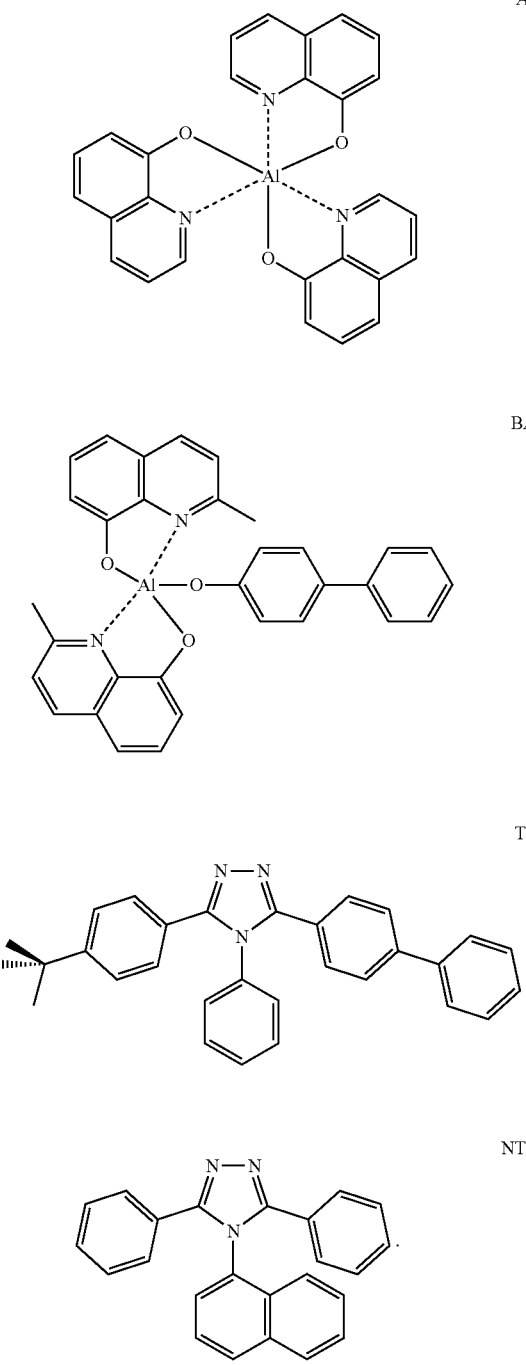

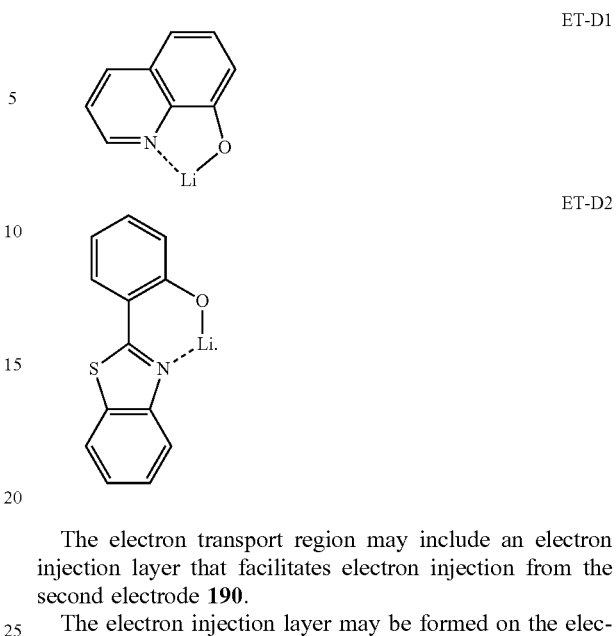

The thickness of the electron transport layer may be about 100 Å to about 1,000 Å, and in some embodiments, about 150 Å to about 500 Å. When the thickness of the electron transport layer is within these ranges, excellent electron transport characteristics may be achieved without a substantial increase in driving voltage.

The electron transport layer may further include a metal-containing material, in addition to the materials described above.

The metal-containing material may include a Li complex. Non-limiting examples of the Li complex may include Compound ET-D1 (lithium quinolate, LiQ) and ET-D2:

The electron transport region may include an electron injection layer that facilitates electron injection from the second electrode 190.

The electron injection layer may be formed on the electron transport layer using one or more suitable methods (such as vacuum deposition, spin coating, casting, an LB method, ink-jet printing, laser printing, and/or LITI). When the electron injection layer is formed by vacuum deposition and/or spin coating, the vacuum deposition and coating conditions used for the electron injection layer may be similar to the vacuum deposition and coating conditions used for the hole injection layer.

The electron injection layer may include at least one selected from LiF, NaCl, CsF, $Li_2O$, BaO, and LiQ.

The thickness of the electron injection layer may be about 1 Å to about 100 Å, and in some embodiments, about 3 Å to about 90 Å. When the thickness of the electron injection layer is within these ranges, excellent electron injection characteristics may be achieved without a substantial increase in driving voltage.

The second electrode 190 may be on the organic layer 150. The second electrode 190 may be a cathode that is an electron injection electrode. In this regard, the material for forming the second electrode 190 may be a material having a low work function, for example, a metal, an alloy, an electrically conductive compound, and/or a mixture thereof. Non-limiting examples of the material for forming the second electrode 190 may include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be ITO or IZO.

The second electrode 190 may be a semi-transmissive electrode or a transmissive electrode.

Hereinbefore the organic light-emitting device 10 has been described with reference to FIG. 1, but embodiments of the present disclosure are not limited thereto.

The term "$C_1$-$C_{60}$ alkyl group" as used herein refers to a linear or branched aliphatic hydrocarbon monovalent group having 1 to 60 carbon atoms, and non-limiting examples thereof may include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having substantially the same structure as the $C_1$-$C_{60}$ alkyl group.

The term "$C_1$-$C_{60}$ alkoxy group" as used herein refers to a monovalent group represented by —O-$A_{101}$ (where $A_{101}$ is a $C_1$-$C_{60}$ alkyl group). Non-limiting examples thereof may include a methoxy group, an ethoxy group, and an isopropyloxy group.

The term "$C_2$-$C_{60}$ alkenyl group" as used herein refers to a hydrocarbon group having at least one carbon-carbon double bond in the body (e.g., middle) or at the terminus of the $C_2$-$C_{60}$ alkyl group. Non-limiting examples thereof may include an ethenyl group, a propenyl group, and a butenyl group. The term "$C_2$-$C_{60}$ alkenylene group" as used herein refers to a divalent group having as the same structure as the $C_2$-$C_{60}$ alkenyl group.

The term "$C_2$-$C_{60}$ alkynyl group" as used herein refers to a hydrocarbon group having at least one carbon-carbon triple bond in the body (e.g., middle) or at the terminus of the $C_2$-$C_{60}$ alkyl group. Non-limiting examples thereof may include an ethynyl group and a propynyl group. The term "$C_2$-$C_{60}$ alkynylene group" as used herein refers to a divalent group having substantially the same structure as the $C_2$-$C_{60}$ alkynyl group.

The term "$C_3$-$C_{10}$ cycloalkyl group" as used herein refers to a monovalent monocyclic saturated hydrocarbon group including 3 to 10 carbon atoms, and non-limiting examples thereof may include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having substantially the same structure as the $C_3$-$C_{10}$ cycloalkyl group.

The term "$C_1$-$C_{10}$ heterocycloalkyl group" as used herein refers to a monovalent monocyclic group including at least one heteroatom selected from nitrogen (N), oxygen (O), silicon (Si), phosphorus (P), and sulfur (S) as a ring-forming atom in addition to 1 to 10 carbon atoms. Non-limiting examples thereof may include a tetrahydrofuranyl group and a tetrahydrothiophenyl group. The term "$C_1$-$C_{10}$ heterocycloalkylene group" as used herein refers to a divalent group having substantially the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in its ring, and is not aromatic. Non-limiting examples thereof may include a cyclopentenyl group, a cyclohexenyl group, and a cycloheptenyl group. The term "$C_3$-$C_{10}$ cycloalkenylene group" as used herein refers to a divalent group having substantially the same structure as the $C_3$-$C_{10}$ cycloalkenyl group.

The term "$C_1$-$C_{10}$ heterocycloalkenyl group" as used herein refers to a monovalent monocyclic group including at least one heteroatom selected from N, O, Si, P, and S as a ring-forming atom, 1 to 10 carbon atoms, and at least one double bond in its ring. Non-limiting examples of the $C_1$-$C_{10}$ heterocycloalkenyl group may include a 2,3-hydrofuranyl group and a 2,3-hydrothiophenyl group. The term "$C_1$-$C_{10}$ heterocycloalkenylene group" as used herein refers to a divalent group having substantially the same structure as the $C_1$-$C_{10}$ heterocycloalkenyl group.

The term "$C_{60}$-$C_{60}$ aryl group" as used herein refers to a monovalent group having a carbocyclic aromatic system having 6 to 60 carbon atoms. The term "$C_{60}$-$C_{60}$ arylene group" as used herein refers to a divalent group having a carbocyclic aromatic system having 6 to 60 carbon atoms. Non-limiting examples of the $C_6$-$C_{60}$ aryl group may include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the rings may be fused (e.g., condensed) to each other.

The term "$C_1$-$C_{60}$ heteroaryl group" as used herein refers to a monovalent group having a carbocyclic aromatic system including at least one heteroatom selected from N, O, Si, P, and S as a ring-forming atom in addition to 1 to 60 carbon atoms. The term "$C_1$-$C_{60}$ heteroarylene group" as used herein refers to a divalent group having a carbocyclic aromatic system including at least one heteroatom selected from N, O, P, and S as a ring-forming atom in addition to 1 to 60 carbon atoms. Non-limiting examples of the $C_1$-$C_{60}$ heteroaryl group may include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the rings may be fused (e.g., condensed) to each other.

The term "$C_6$-$C_{60}$ aryloxy group" as used herein refers to a group represented by —O-$A_{102}$ (where $A_{102}$ is a $C_6$-$C_{60}$ aryl group). The term "$C_6$-$C_{60}$ arylthio group" as used herein refers to a group represented by —S-$A_{103}$ (where $A_{103}$ is a $C_6$-$C_{60}$ aryl group).

The term "monovalent non-aromatic condensed polycyclic group" as used herein refers to a monovalent group that has two or more rings condensed (e.g., coupled) to each other, has only carbon atoms as ring-forming atoms (for example, 8 to 60 carbon atoms), and is non-aromatic in the entire molecular structure. A non-limiting example of the monovalent non-aromatic condensed polycyclic group may include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more rings condensed (e.g., coupled) to each other, has a heteroatom selected from N, O, Si, P, and S in addition to carbon atoms (for example, 2 to 60 carbon atoms), as ring-forming atoms, and is non-aromatic in the entire molecular structure. A non-limiting example of the monovalent non-aromatic condensed heteropolycyclic group may include a carbazolyl group. The term "divalent non-aromatic condensed hetero-polycyclic group" as used herein refers to a divalent group having substantially the same structure as the monovalent non-aromatic condensed hetero-polycyclic group.

In the present specification, at least one substituent of the substituted electron transport group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ hetero-cycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

Hereinafter, an organic light-emitting device according to an embodiment of the present disclosure will be described in more detail with reference to Examples, however, embodiments of the present disclosure are not limited thereto.

EXAMPLE

Synthesis Example 1

Synthesis of Compound 1-2

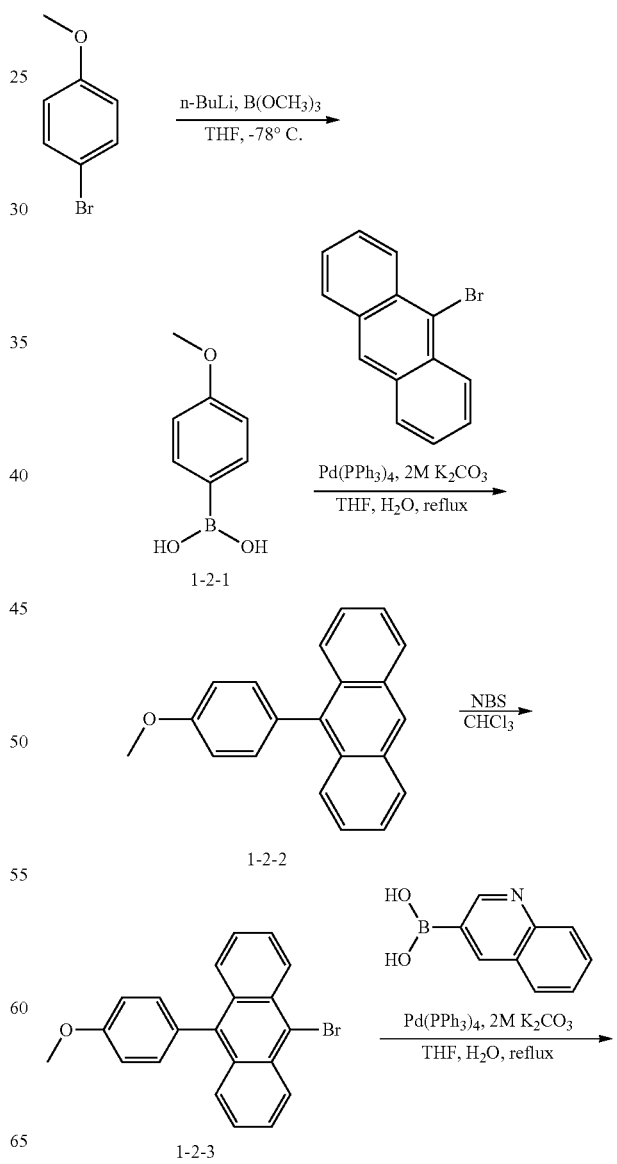

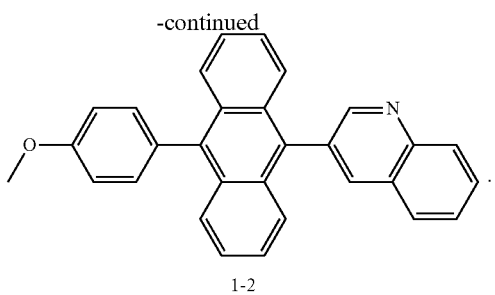

1-2

Synthesis of Intermediate 1-2-1

5 g of 4-bromo anisole (23.24 mmol) was added to a 2-neck round bottom flask, sealed, and dried under reduced pressure. 250 mL of purified tetrahydrofuran (THF) was added thereto, and the temperature was maintained at about −78° C. using dry ice and acetone. 22 mL of n-butyl lithium solution (1.6 mol/L in hexane, 34.87 mmol) was slowly injected thereto, and the reaction was stirred for about 1 hour while maintaining the temperature. 5.21 mL of trimethyl borate (46.49 mmol) was added thereto, and the solution was stirred while its temperature was slowly raised to ambient temperature. After 5 hours, a large amount (20 mL) of 1N HCl was added thereto, and the solution was stirred for 2 hours. 2M NaOH was added thereto to neutralize the reaction to a pH of 7. Once the reaction was complete, an organic layer was separated by adding an excess of dichloromethane and H$_2$O. The organic layer was dried over sodium sulfate and then filtered to remove the drying agent. The solvent was removed from the product, and column chromatography using dichloromethane and methanol at a ratio of 4:1 was carried out to obtain 3.0 g of (4-methoxyphenyl)boronic acid (1) as a white solid (yield: 48.7%).

$^1$H NMR (500 MHz, MeOH-d$_4$): δ (ppm) 7.7. (d, J=8 Hz, 2H), 7.55 (s, 2H), 6.85 (d, J=8 Hz, 2H), 3.74 (s, 3H)

$^{13}$C NMR (125 MHz, MeOH-d$_4$): δ (ppm) 163.9, 136.7, 114.1, 55.5

Synthesis of Intermediate 1-2-2

2.64 g of 9-bromoanthracene (11.89 mmol), 4.45 g of (4-methoxyphenyl)boronic acid (23.78 mmol), 2 mol/L potassium carbonate (in H$_2$O, 60 mL), and 0.69 g of tetrakis(triphenylphosphine)palladium(0) (0.594 mmol) were mixed with 200 mL of THF and 40 mL of methanol as solvent under a nitrogen atmosphere, and the solution was heated and stirred. After 24 hours, completion of the reaction was confirmed by thin layer chromatography (TLC), and the solvent was filtered using Celite®. An organic layer was separated using an excess of dichloromethane and H$_2$O. The organic layer was washed with a saturated sodium chloride solution, dried over sodium sulfate, and filtered to remove the drying agent. The solvent was removed from the product, and column chromatography using hexane was carried out to obtain 2.70 g of 9-(4-methoxyphenyl)anthracene (yield: 80.0%).

$^1$H NMR (400 MHz, CDCl$_3$): δ (ppm) 8.48 (s, 1H), 8.04 (d, J=8.24 Hz, 2H), 7.72 (d, J=8.68 Hz, 2H), 7.48-7.44 (dd, J=2.4, 2.4 Hz, 2H), 7.37-7.35 (m, 4H), 7.12 (d, J=8.68 Hz, 2H), 3.95 (s, 3H)

Synthesis of Intermediate 1-2-3

5.00 g of 9-(4-methoxyphenyl)anthracene (17.58 mmol) and 3.75 g of N-bromosuccinimide (NBS) (21.10 mmol) were added to a 2-neck round bottom flask, sealed, and dried under reduced pressure. 200 mL of chloroform was added thereto, and then the solution was heated and stirred for about 2 hours. Completion of the reaction was confirmed by TLC, and the solvent was removed therefrom. Subsequently, recrystallization was carried out using a mixture of acetone and methanol. The recrystallized solvent was filtrated to obtain 4.66 g of 9-bromo-10-(4-methoxyphenyl)anthracene (yield: 73.0%).

$^1$H NMR (400 MHz, CDCl$_3$): δ (ppm) 8.61 (d, J=9.16 Hz, 2H), 7.71 (d, J=8.68 Hz, 2H), 7.61~7.57 (dd, J=7.76, 7.86 Hz, 2H), 7.40~7.36 (dd, J=9.16, 8.68 Hz, 2H), 7.32 (d, J=8.68, 2H), 7.12 (d, J=8.72 Hz, 2H), 3.95 (s, 3H)

$^{13}$C-NMR (300 MHz, CDCl$_3$): δ (ppm) 160.0, 137.5, 132.1, 131.2, 130.2, 130.1, 127.7, 127.4, 126.8, 125.3, 122.4, 113.8, 55.4

Synthesis of Compound 1-2

2.00 g of 9-bromo-10-(4-methoxyphenyl)anthracene (5.51 mmol), 3.81 g of quinolin-3-ylboronic acid (22.02 mmol), 2 mol/L potassium carbonate (in H$_2$O, 5.5 mL), and 0.64 g of tetrakis(triphenylphosphine)palladium(0) (0.55 mmol) were mixed with 100 mL of THF under a nitrogen atmosphere, and the solution was heated and stirred. After 24 hours, completion of the reaction was confirmed by TLC, and the solvent was filtered using Celite®. An organic layer was separated using an excess of dichloromethane and H$_2$O. The organic layer was washed with a saturated sodium chloride solution, dried over sodium sulfate, and filtered to remove the drying agent. The solvent was removed from the product, and column chromatography using ethyl acetate and hexane at a ratio of 1:9 was carried out to obtain 1.70 g of 3-(10-(4-methoxyphenyl)anthracen-9-yl)quinolone as a bright yellow solid (yield: 75%).

$^1$H NMR (400 MHz, CDCl$_3$): δ (ppm) 9.02 (s, 1H), 8.31 (m, 2H), 7.93 (d, J=8 Hz, 1H), 7.85 (t, J=7.2 Hz, 1H), 7.80~7.77 (m, 2H), 7.69~7.62 (m, 3H), 7.42~7.22 (m, 6H), 7.15 (d, J=8.4 Hz, 2H), 3.96 (s, 3H)

$^{13}$C-NMR (100 MHz, CDCl$_3$): δ (ppm) 160.9, 152.8, 138.3, 138.2, 132.3, 132.2, 130.7, 130.4, 130.2, 129.9, 129.3, 128.9, 128.0, 127.9, 127.4, 127.3, 126.2, 125.7, 125.1, 121.8, 114.0, 113.9, 55.4

Synthesis Example 2

Synthesis of Compound 1-3

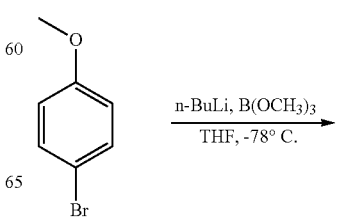

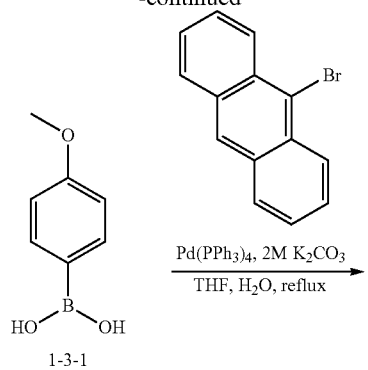

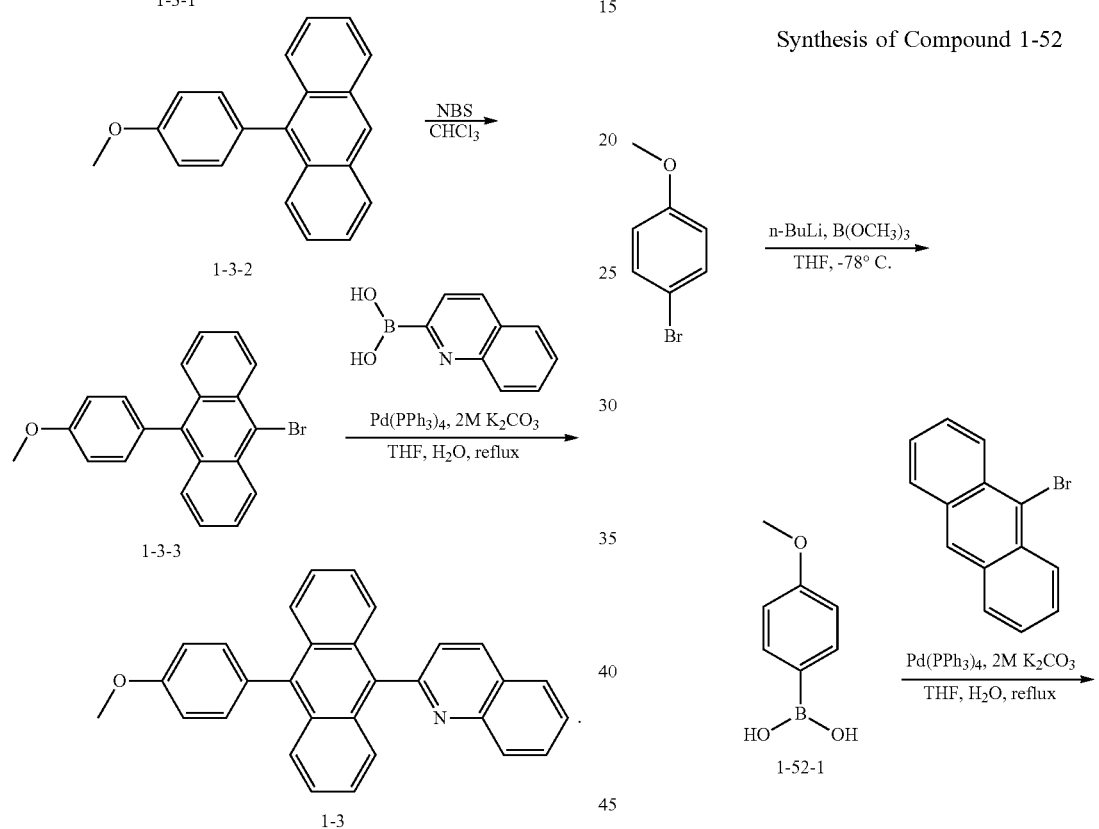

Synthesis of Compound 1-3

Intermediate 1-3-3 was synthesized in substantially the same manner as in Synthesis of Compound 1-2.

2.00 g of 9-bromo-10-(4-methoxyphenyl)anthracene (5.51 mmol), 3.81 g of quinolin-2-ylboronic acid (22.02 mmol), 2 mol/L potassium carbonate (in H$_2$O, 5.5 mL), and 0.64 g of tetrakis(triphenylphosphine)palladium(0) (0.55 mmol) were mixed with 100 mL of THF under a nitrogen atmosphere, and the solution was heated and stirred. After 24 hours, completion of the reaction was confirmed by TLC, and the solvent was filtered using Celite®. An organic layer was separated using an excess of dichloromethane and H$_2$O. The organic layer was washed with a saturated sodium chloride solution, dried over sodium sulfate, and filtered to remove the drying agent. The solvent was removed from the product, and column chromatography using ethyl acetate and hexane at a ratio of 1:9 was carried out to obtain 1.70 g of 2-(10-(4-methoxyphenyl)anthracen-9-yl)quinolone as a bright yellow solid (yield: 75%).

$^1$H NMR (400 MHz, CDCl$_3$): δ (ppm) 8.44 (d, J=8.3 Hz, 1H), 8.29 (d, J=8.2 Hz, 1H), 8.05 (d, J=7.9 Hz, 1H), 7.84 (d, J=8.2 Hz, 1H), 7.79 (d, J=7.5 Hz, 2H), 7.73 (d, J=8.4 Hz, 2H), 7.61 (m, 2H), 7.47 (m, 1H), 7.35 (m, 5H) 7.18 (d, J=8.3 Hz, 2H), 4.00 (s, 3H)

$^{13}$C-NMR (100 MHz, CDCl$_3$): δ (ppm) 159.1, 136.4, 132.5, 132.1, 131.0, 130.4, 130.0, 129.7, 127.7, 127.3, 127.1, 126.9, 126.1, 125.6, 125.0, 124.7, 113.9, 113.8, 55.4

Synthesis Example 3

Synthesis of Compound 1-52

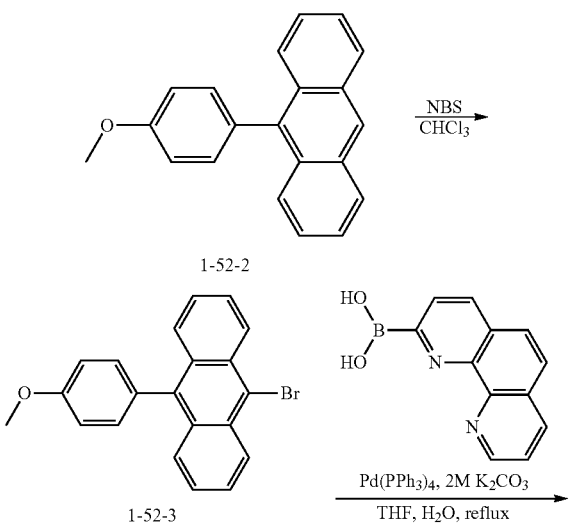

-continued

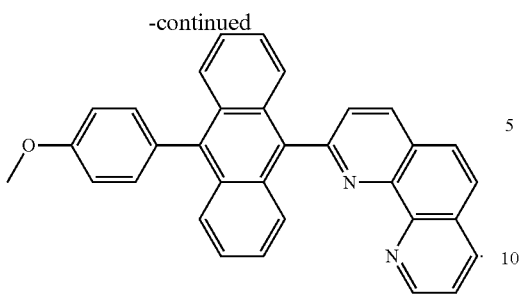

1-52

Synthesis of Compound 1-52

Intermediate 1-52-3 was synthesized in substantially the same manner as in Synthesis of Compound 1-2.

2.00 g of 9-bromo-10-(4-methoxyphenyl)anthracene (5.51 mmol), 4.95 g of (1,10-phenanthrolin-2-yl)boronic acid (22.02 mmol), 2 mol/L potassium carbonate (in $H_2O$, 5.5 mL), and 0.64 g of tetrakis(triphenylphosphine)palladium(0) (0.55 mmol) were mixed with 100 mL of THF under a nitrogen atmosphere, and the solution was heated and stirred. After 24 hours, completion of the reaction was confirmed by TLC, and the solvent was filtered using Celite®. An organic layer was separated using an excess of dichloromethane and $H_2O$. The organic layer was washed with a saturated sodium chloride solution, dried over sodium sulfate, and filtered to remove the drying agent. The solvent was removed from the product, and column chromatography using ethyl acetate and hexane at a ratio of 1:9 was carried out to obtain 1.91 g of 2-(10-(4-methoxyphenyl)anthracen-9-yl)-1,10-phenanthroline) as a bright yellow solid (yield: 75%).

$^1$H NMR (400 MHz, $CDCl_3$): δ (ppm) 9.09 (d, J=3.6 Hz, 1H), 8.42 (d, J=8 Hz, 1H), 8.26 (d, J=8 Hz, 1H), 7.26 (t, J=8 Hz, 2H), 7.73 (d, J=8.6 Hz, 2H), 7.50 (m, 1H), 7.46 (m, 2H), 7.40 (d, J=8.4 Hz, 2H), 7.29~7.19 (m, 6H), 7.14 (dd, J=8.4 Hz, 2.8 Hz, 1H), 3.97 (s, 3H)

$^{13}$C-NMR (100 MHz, $CDCl_3$): δ (ppm) 159.06, 139.26, 138.0, 136.1, 132.5, 132.2, 131.0, 130.2, 130.0, 128.9, 128.0, 127.5, 127.1, 126.6, 126.5, 126.5, 126.2, 125.3, 124.9, 123.9, 123.0, 122.5, 113.9

Evaluation Example 1

Thermal Characteristics Evaluation Via Thermogravimetric Analysis (TGA) and Differential Scanning Calorimetry (DSC)

Thermal analysis under an $N_2$ atmosphere was carried out via thermogravimetric analysis (TGA) (from ambient temperature to about 800° C. at a rate of 10° C./min) and differential scanning calorimetry (DSC) (from ambient temperature to about 400° C.) on Compounds 1-2, 1-3, and 1-52 (TGA pan type: Pt Pan in disposable Al Pan; DSC pan type: disposable Al pan). The evaluation results are shown in FIGS. 2 to 7 and Table 1. Referring to Table 1, it was found that Compounds 1-2, 1-3, and 1-52 had excellent thermal stability.

TABLE 1

|  | TGA (5% weight loss) | DSC |
| --- | --- | --- |
| Compound 1-2 | $T_d$: 346° C. | $T_m$: 235° C. |
| Compound 1-3 | $T_d$: 339° C. | $T_g$: 96° C. |
| Compound 1-52 | $T_d$: 375° C. | $T_g$: 97° C. |

Example 1

A 15 Ohms per square centimeter (Ω/$cm^2$) (1,200 Å) ITO glass substrate (available from Corning Co., Ltd) coated with ITO as an anode was cut to a size of 50 millimeters (mm)×50 mm×0.7 mm, sonicated in isopropyl alcohol and pure water for 5 minutes in each solvent, cleaned with ultraviolet rays for 30 minutes, exposed to ozone, and mounted on a vacuum deposition apparatus.

2-TNATA was vacuum-deposited on the ITO anode to form a hole injection layer having a thickness of about 600 Å. NPB was then deposited on the hole injection layer to form a hole transport layer having a thickness of about 300 Å, thereby forming a hole transport region.

Compound 2-7 (as a host) and Compound 1-2 (as a dopant) were co-deposited on the hole transport region at a weight ratio of about 95:5 to form an emission layer having a thickness of about 400 Å.

Thereafter, Compound 201 was deposited on the emission layer to form an electron transport layer having a thickness of about 300 Å, LiF was deposited on the electron transport layer to form an electron injection layer having a thickness of about 10 Å, and aluminum (Al) was vacuum-deposited on the electron injection layer to form a cathode having a thickness of about 1,000 Å, thereby completing the manufacture of an organic light-emitting device. Deposition equipment (Sunicel plus 200) manufactured by Sunic System Ltd. was used in the deposition.

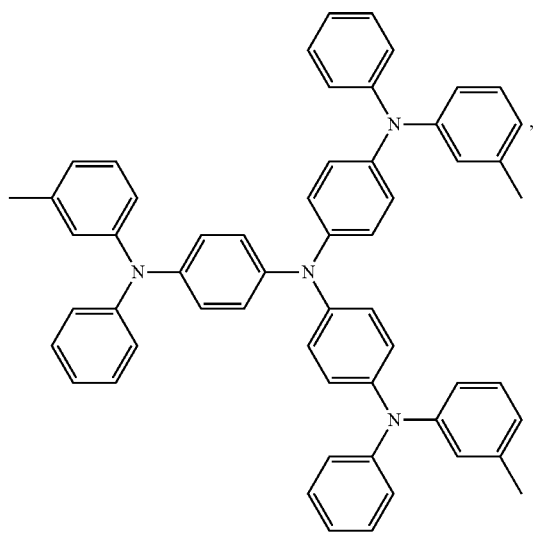

2-TNATA

-continued

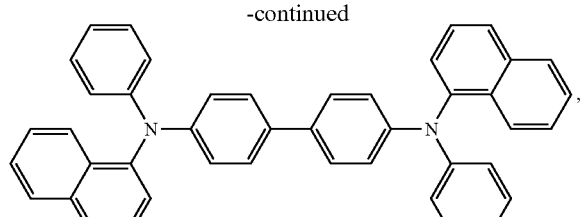

NPB

Compound 201

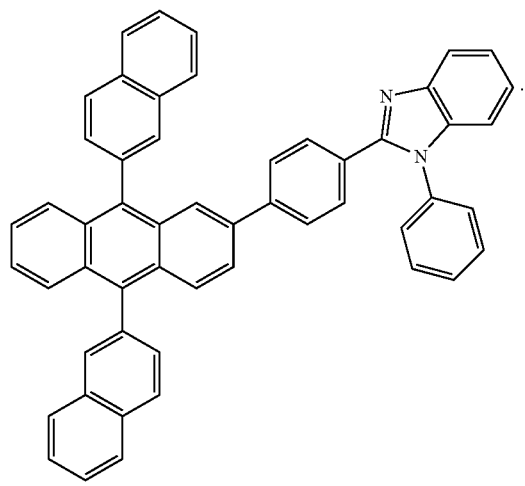

Examples 2 and 3 and Comparative Examples 1 to 3

Additional organic light-emitting devices were manufactured in the same manner as in Example 1, except that Compounds 1-3, 1-52, dopant A, and dopant B were each used instead of Compound 1-2 as the dopant in the formation of an emission layer in Examples 2 and 3 and Comparative Examples 1 and 2, respectively. In addition, Compound A was used as a host and Compound B was used as a dopant in Comparative Example 3.

Evaluation Example 2

The driving voltage, current density, efficiency, color-coordination, and T95 lifespan of each of the organic light-emitting devices manufactured in Examples 1 and 3 and Comparative Examples 1 to 3 were measured using a Keithley 236 source-measure unit (SMU) and a PR650 luminance meter. The results thereof are shown in Table 2. The T95 lifespan indicates the time elapsed (in hours) for the luminance of the organic light-emitting device to decline to 95% of its initial luminance (at a current density of 10 mA/cm$^2$).

TABLE 2

|  | Host | Dopant | Driving Voltage [V] | Efficiency [cd/A] | Color-coordinate CIE x | Color-coordinate CIE y | T95 lifespan [hr @ 100 mA/cm$^2$] |
| --- | --- | --- | --- | --- | --- | --- | --- |
| Example 1 | Compound 2-7 | Compound 1-2 | 3.4 | 5.2 | 0.151 | 0.115 | 160 |
| Example 2 | Compound 2-7 | Compound 1-3 | 3.4 | 5.1 | 0.150 | 0.118 | 150 |
| Example 3 | Compound 2-7 | Compound 1-52 | 3.4 | 5.3 | 0.151 | 0.124 | 150 |
| Comparative Example 1 | Compound 2-7 | Dopant A | 4.4 | 4.5 | 0.151 | 0.162 | 70 |
| Comparative Example 2 | Compound 2-7 | Dopant B | 4.2 | 5.2 | 0.150 | 0.152 | 110 |
| Comparative Example 3 | Compound A | Compound B | 4.2 | 6.2 | 0.175 | 0.238 | 80 |

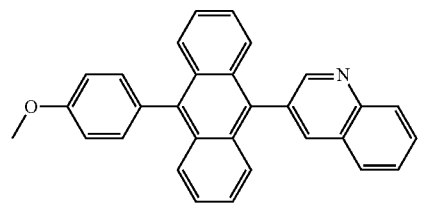

1-2

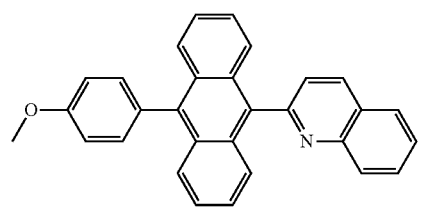

1-3

TABLE 2-continued
| | | Driving Voltage | Efficiency | Color-coordinate | | T95 lifespan |
|---|---|---|---|---|---|---|
| Host | Dopant | [V] | [cd/A] | CIE x | CIE y | [hr @ 100 mA/cm²] |
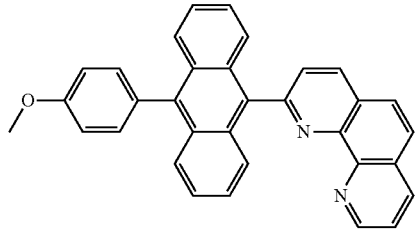
1-52
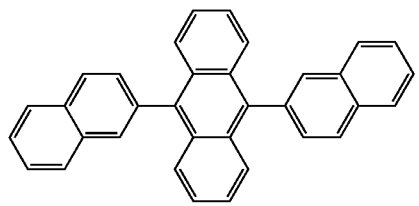
2-7
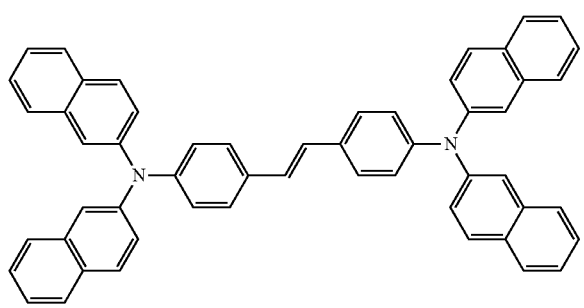
Dopant A
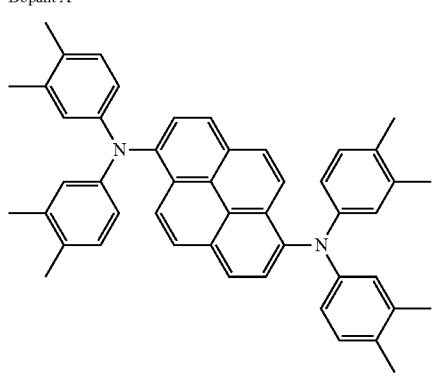
Dopant B
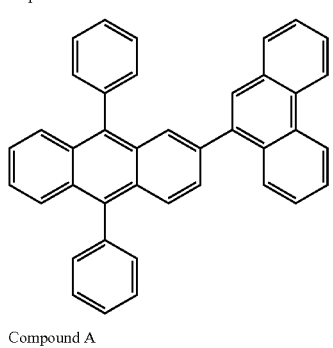
Compound A TABLE 2-continued

| | | Driving Voltage | Efficiency | Color-coordinate | | T95 lifespan |
|---|---|---|---|---|---|---|
| Host | Dopant | [V] | [cd/A] | CIE x | CIE y | [hr @ 100 mA/cm$^2$] |

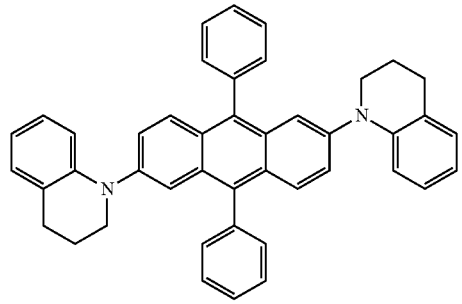

Compound B.

Referring to Table 2, it was found that the organic light-emitting devices manufactured in Examples 1 to 3 exhibited improved or lowered driving voltages, improved or increased luminance, improved or increased efficiencies, and improved or increased half-lifespans as compared to the organic light-emitting devices manufactured in Comparative Examples 1 to 3.

As described above, an organic light-emitting device according to an embodiment of the present disclosure may have high efficiency and long lifespan.

It should be understood that the embodiments described herein should be considered in a descriptive sense only and not for purposes of limitation. Descriptions of features or aspects within each embodiment should typically be considered as being available for other similar features or aspects in other embodiments.

As used herein, expressions such as "at least one of", "one of", "selected from", "at least one selected from", and "one selected from", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more embodiments have been described with reference to the drawings, it will be understood by those of ordinary skill in the art that various changes in form and details may be made therein without departing from the spirit and scope of the present disclosure as defined by the following claims and equivalents thereof.

What is claimed is:
1. An organic light-emitting device comprising:
a first electrode;
a second electrode facing the first electrode; and
an organic layer between the first electrode and the second electrode and comprising an emission layer, wherein:
the organic layer comprises a first compound represented by Formula 1 and a second compound represented by Formula 2:

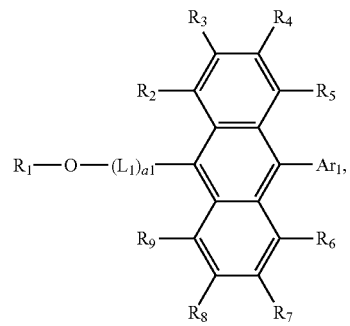

Formula 1

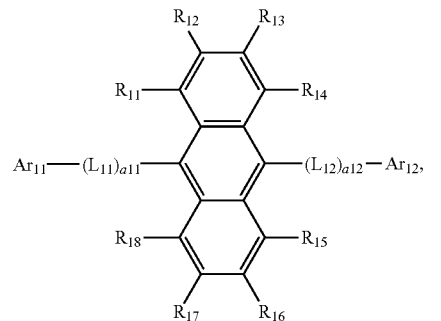

Formula 2 wherein, in Formulae 1 and 2,
$L_1$, $L_{11}$, and $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1, a11, and a12 may each independently an integer selected from 0 to 5, and when a1 is 2 or more, a plurality of $L_1$ groups are identical to or different from each other, when a11 is 2 or more, a plurality of $L_{11}$ groups are identical to or different from each other, and when a12 is 2 or more, a plurality of $L_{12}$ groups are identical to or different from each other, $Ar_1$ is selected from the group consisting of:

an imidazolyl group, a pyrazolyl group, a thiazolyl group, an isothiazolyl group, an oxazolyl group, an isoxazolyl group, a pyrazinyl group, a pyrimidinyl group, a pyridazinyl group, an indazolyl group, a quinolinyl group, an isoquinolinyl group, a benzoquinolinyl group, a benzoisoquinolinyl group, a phthalazinyl group, a naphthyridinyl group, a benzonaphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, a pyrimidobenzothiophenyl group; and an imidazolyl group, a pyrazolyl group, a thiazolyl group, an isothiazolyl group, an oxazolyl group, an isoxazolyl group, a pyrazinyl group, a pyrimidinyl group, a pyridazinyl group, an indazolyl group, a quinolinyl group, an isoquinolinyl group, a benzoquinolinyl group, a benzoisoquinolinyl group, a phthalazinyl group, a naphthyridinyl group, a benzonaphthyridinyl group, a quinoxalinyl group, a quinazolinyl group, a cinnolinyl group, a phenanthridinyl group, an acridinyl group, a phenanthrolinyl group, a benzophenanthrolinyl group, a phenazinyl group, a benzimidazolyl group, a naphthoimidazolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, an imidazopyridinyl group, an imidazopyrimidinyl group, an imidazoquinolinyl group, an imidazoisoquinolinyl group, a pyridobenzofuranyl group, a pyrimidobenzofuranyl group, a pyridobenzothiophenyl group, and a pyrimidobenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a pyridinyl group, a pyrimidinyl group, a triazinyl group, and —Si($Q_{31}$)($Q_{32}$)($Q_{33}$)

wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group, $Ar_{11}$ and $Ar_{12}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_1$ is selected from the group consisting of:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{60}$ alkyl group; and a $C_1$-$C_{60}$ alkyl group substituted with at least one selected from deuterium, —F, —Cl, —Br, —I, a hydroxyl group, a cyano group, a nitro group, a carboxylic acid group or a salt thereof, a sulfonic acid group or a salt thereof and a phosphoric acid group or a salt thereof, $R_2$ to $R_9$ and $R_{11}$ to $R_{18}$ are each independently selected from:

hydrogen, deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), and at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group; and wherein the emission layer comprises a dopant and a host, the dopant comprises the first compound, and the host comprises the second compound.

2. The organic light-emitting device of claim 1, wherein $L_1$, $L_{11}$, and $L_{12}$ are each independently selected from the group consisting of:

a phenylene group, a pentalenylene group, an indenylene group, a naphthylene group, an azulenylene group, a heptalenylene group, an indacenylene group, an acenaphthylene group, a fluorenylene group, a spirobifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group an indazolylene group, a purinylene group, a quinolinylene group, an isoquinolinylene group, a benzoquinolinylene group, a benzoisoquinolinylene group, a phthalazinylene group, a naphthyridinylene group, a benzonaphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spirobifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group an indazolylene group, a purinylene group, a quinolinylene group, an isoquinolinylene group, a benzoquinolinylene group, a benzoisoquinolinylene group, a phthalazinylene group, a naphthyridinylene group, a benzonaphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a benzoisoquinolinyl group, a phthalazinyl group, a naphthyridinyl group, a benzonaphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolylene group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

3. The organic light-emitting device of claim 1, wherein $L_1$, $L_{11}$, and $L_{12}$ are each independently selected from groups represented by Formulae 3-1 to 3-43:

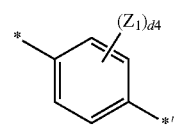

Formula 3-1

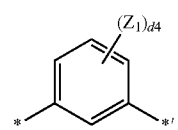

Formula 3-2

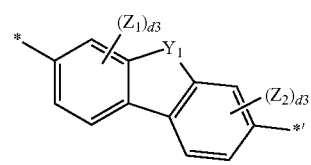

Formula 3-3

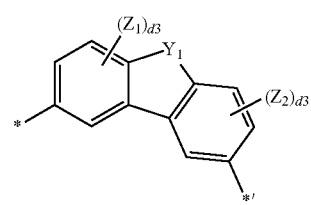

Formula 3-4

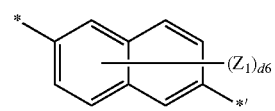

Formula 3-5

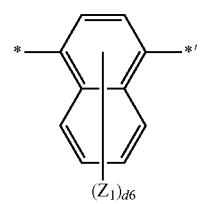

Formula 3-6

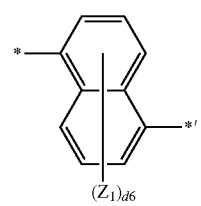

Formula 3-7

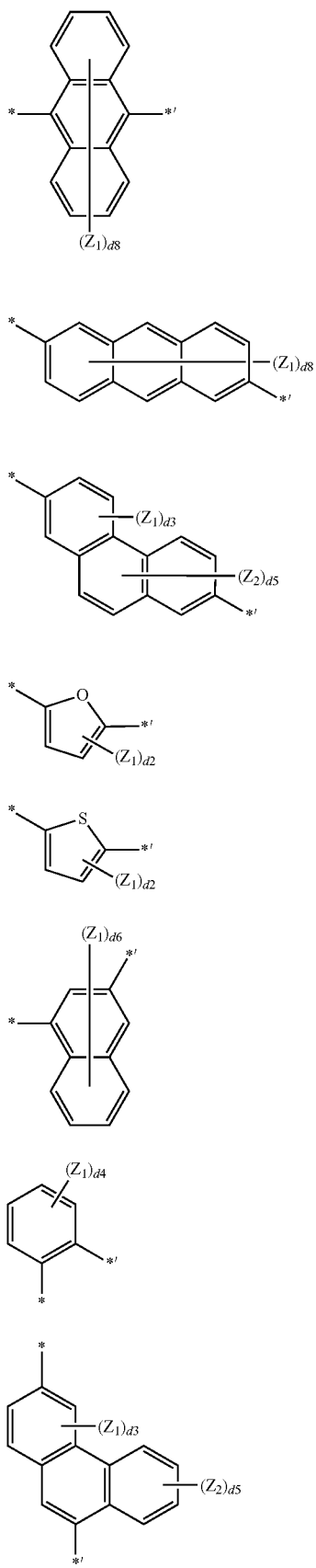
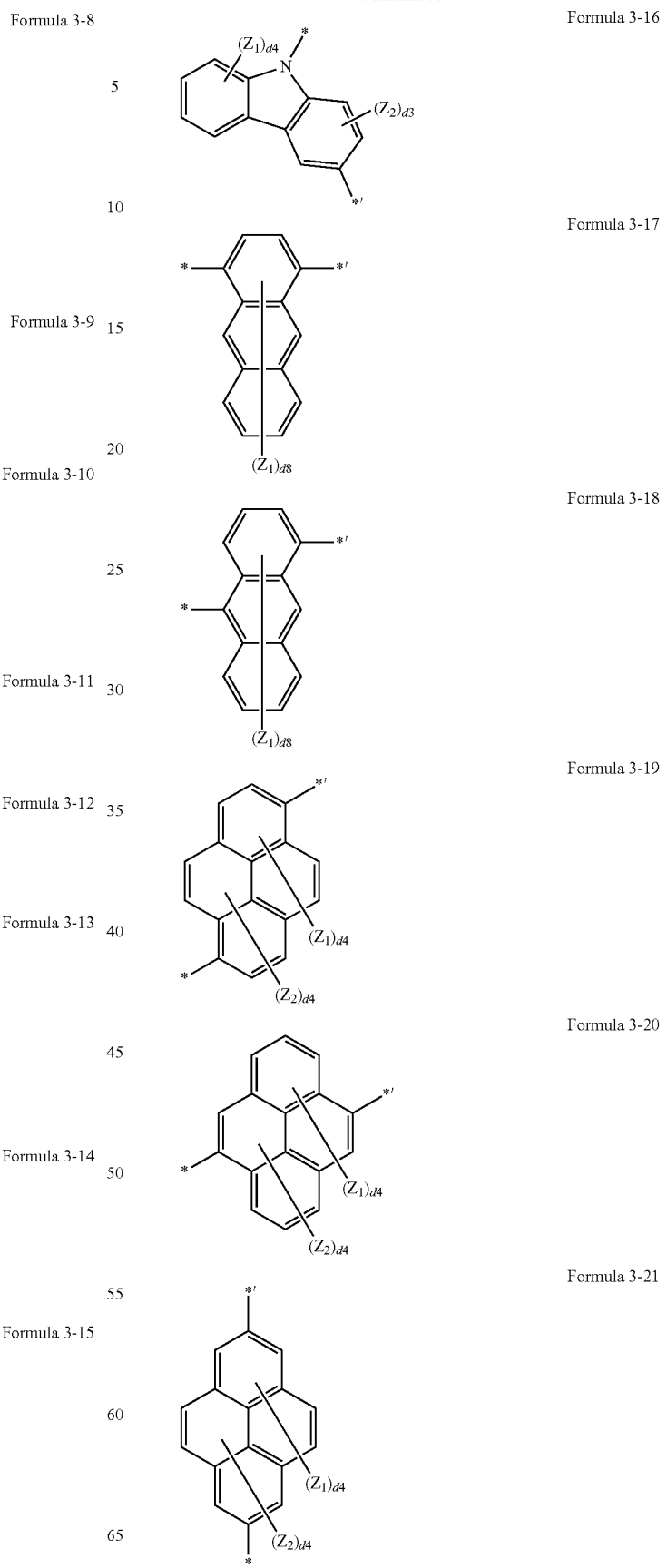

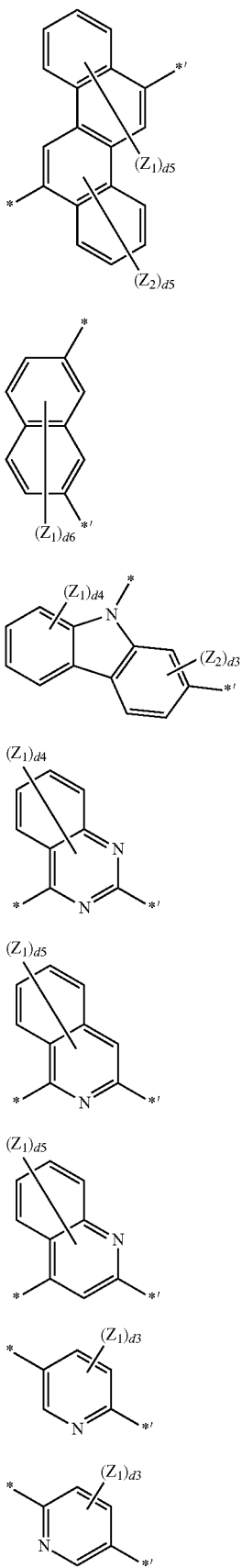
Formula 3-22
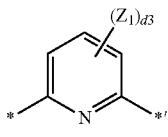
Formula 3-30
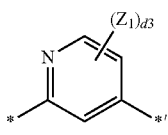
Formula 3-31
Formula 3-23
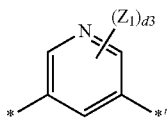
Formula 3-32
Formula 3-33
Formula 3-24
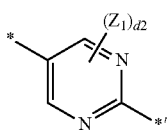
Formula 3-34
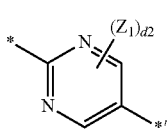
Formula 3-35
Formula 3-25
Formula 3-36
Formula 3-26
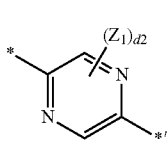
Formula 3-37
Formula 3-38
Formula 3-27
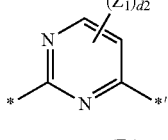
Formula 3-39
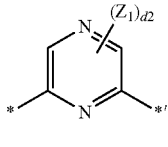
Formula 3-28
Formula 3-40
Formula 3-29
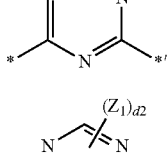
Formula 3-41
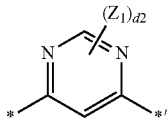

-continued

Formula 3-42

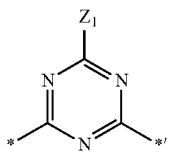

Formula 3-43

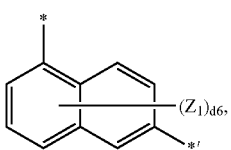

wherein, in Formulae 3-1 to 3-43,
$Y_1$ is selected from O, S, $C(Z_3)(Z_4)$, $N(Z_5)$, and $Si(Z_6)(Z_7)$, and
$Z_1$ to $Z_7$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_{31})(Q_{32})(Q_{33})$,
wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group,
d2 is an integer selected from 1 and 2,
d3 is an integer selected from 1 to 3,
d4 is an integer selected from 1 to 4,
d5 is an integer selected from 1 to 5,
d6 is an integer selected from 1 to 6, and
d8 is an integer selected from 1 to 8.

4. The organic light-emitting device of claim 1, wherein $L_1$, $L_{11}$, and $L_{12}$ are each independently selected from the group consisting of:
a phenylene group, a naphthylene group, a fluorenylene group, a benzofluorenylene group, a phenanthrenylene group, an anthracenylene group, a pyrenylene group, a chrysenylene group; and
a phenylene group, a naphthylene group, a fluorenylene group, a benzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and —$Si(Q_{31})(Q_{32})(Q_{33})$,
wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

5. The organic light-emitting device of claim 1, wherein a1 is selected from 1 and 2, and when a1 is 2, a plurality of $L_1$ groups are identical to or different from each other, and a11 and a12 are each independently selected from 0 and 1.

6. The organic light-emitting device of claim 1, wherein $Ar_1$ is selected from groups represented by Formulae 7-4 to 7-101:

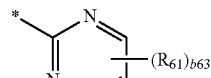
7-4

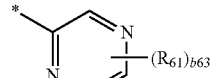
7-5

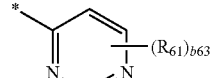
7-6

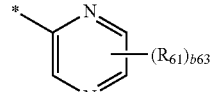
7-7

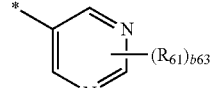
7-8

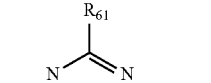
7-9

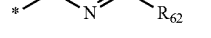

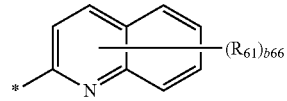
7-10

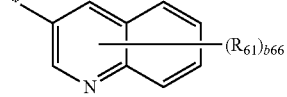
7-11

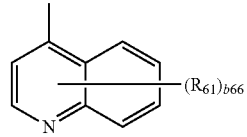
7-12

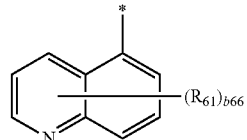
7-13

7-14

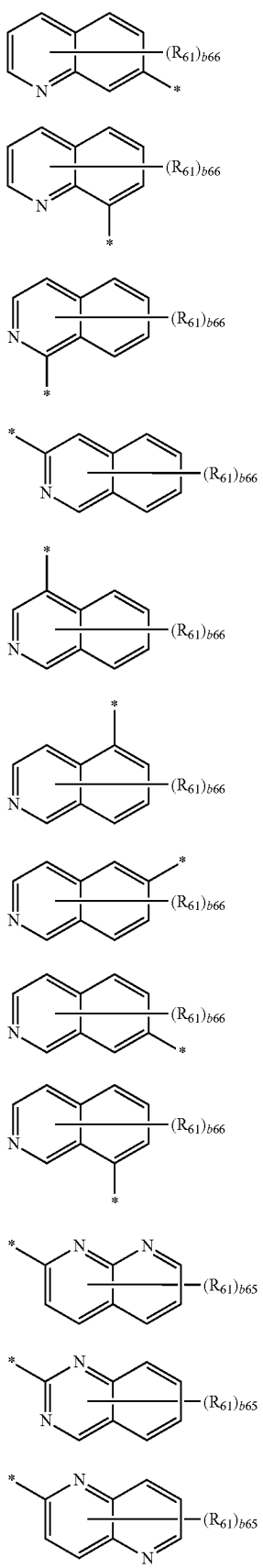
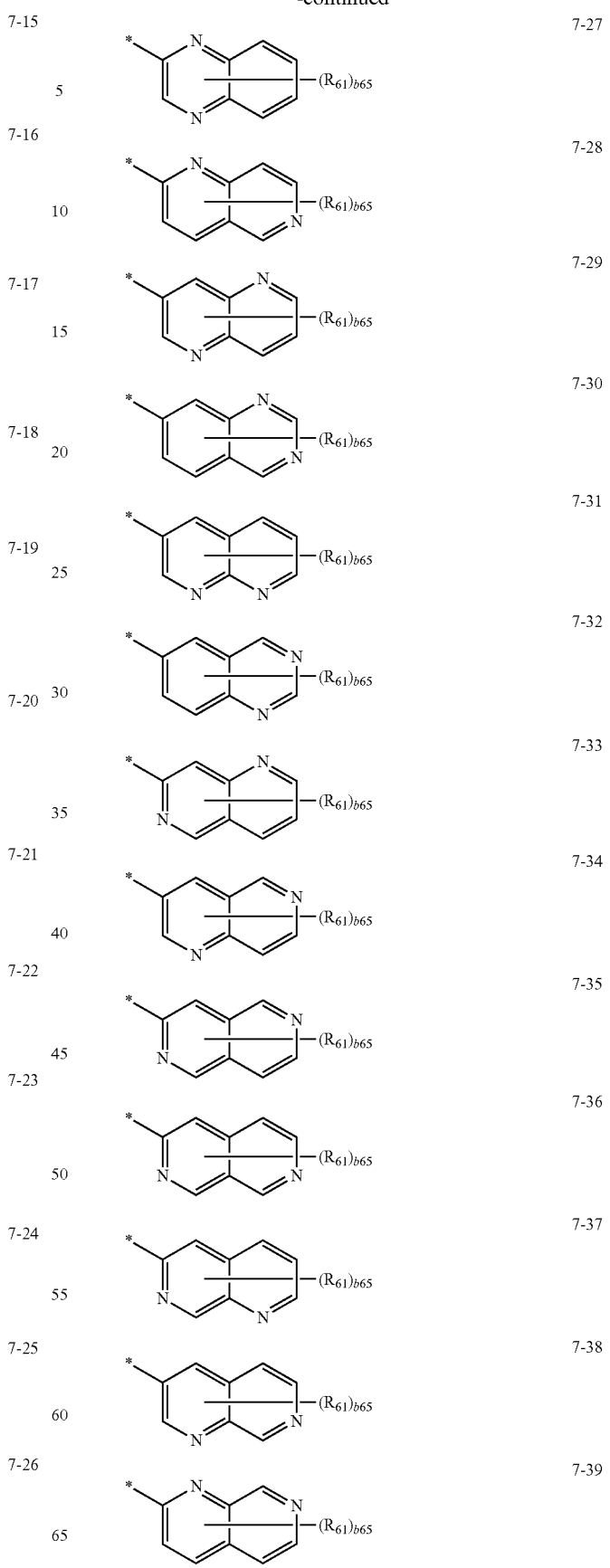

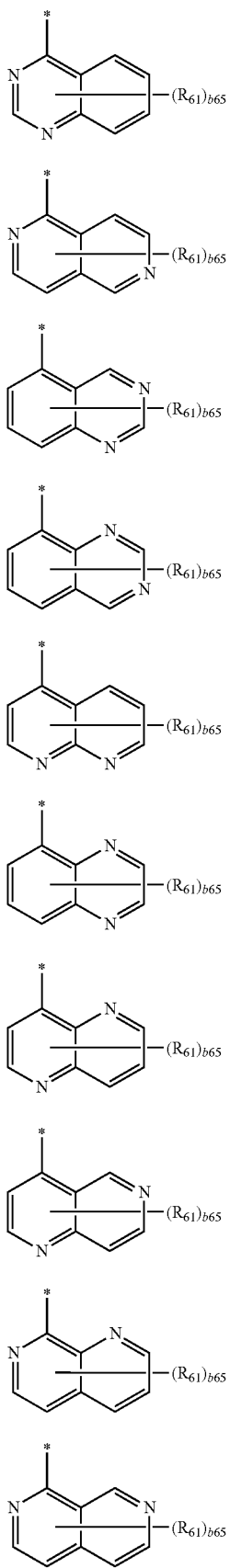
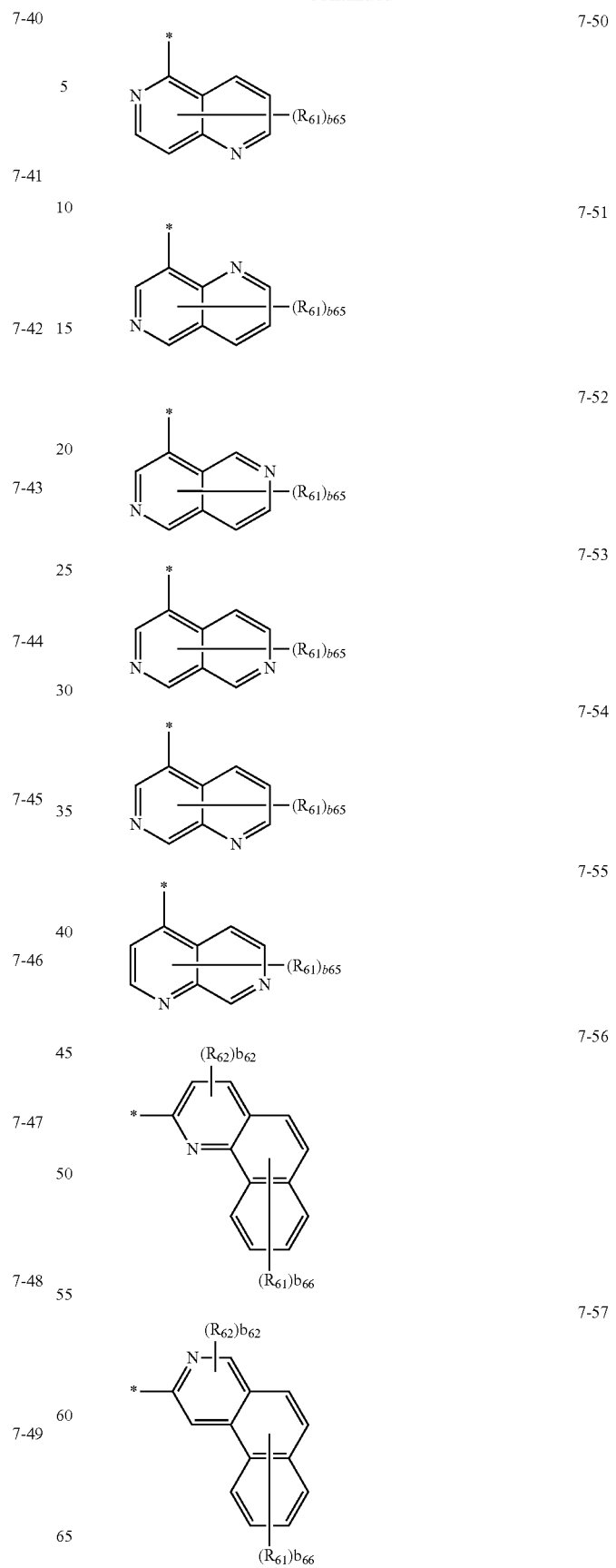

133
-continued
7-58
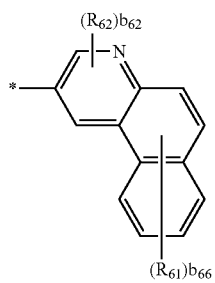
7-59
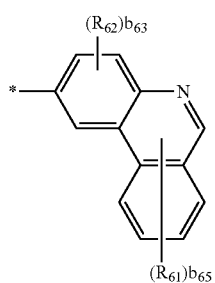
7-60
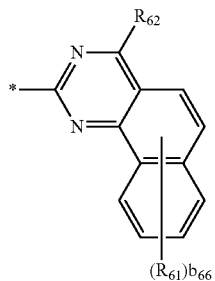
7-61
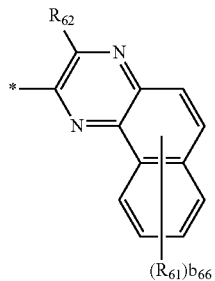
7-62
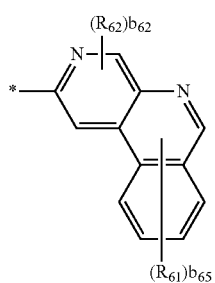
134
-continued
7-63
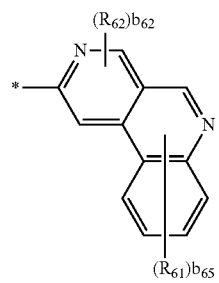
7-64
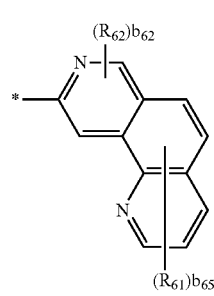
7-65
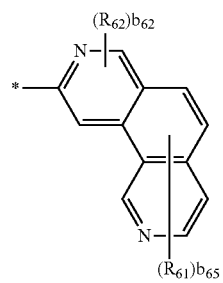
7-66
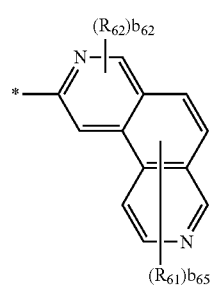
7-67
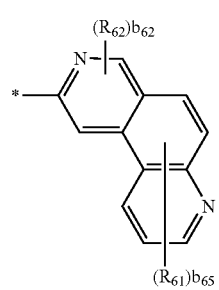

7-68
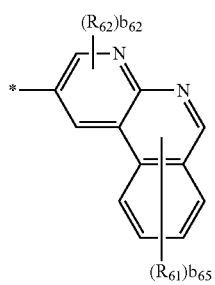
7-69
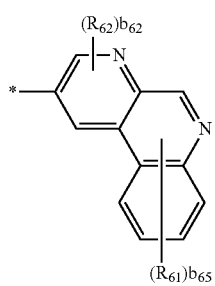
7-70
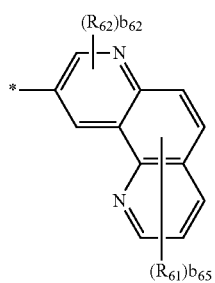
7-71
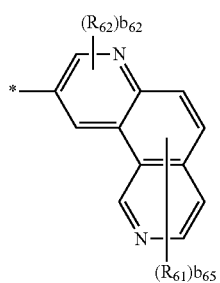
7-72
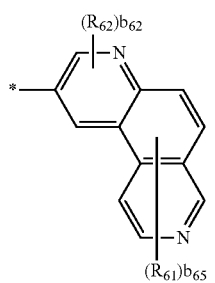
7-73
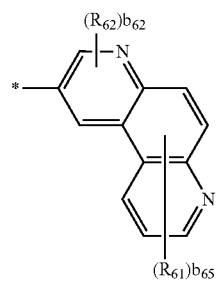
7-74
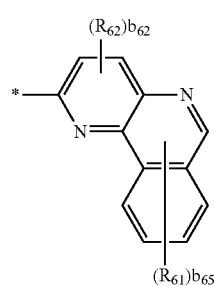
7-75
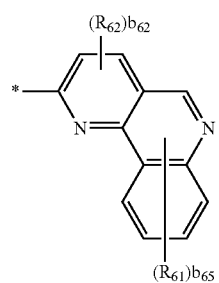
7-76
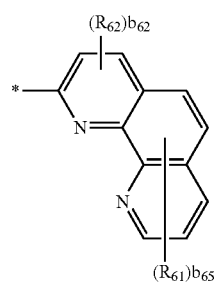
7-77
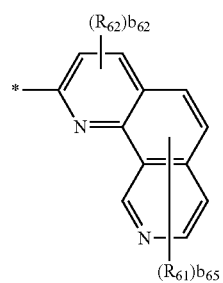

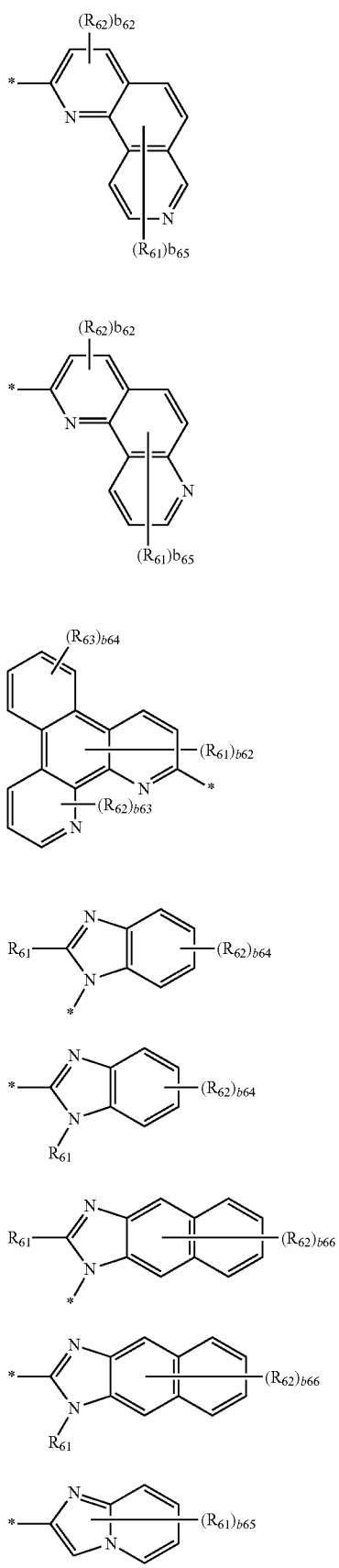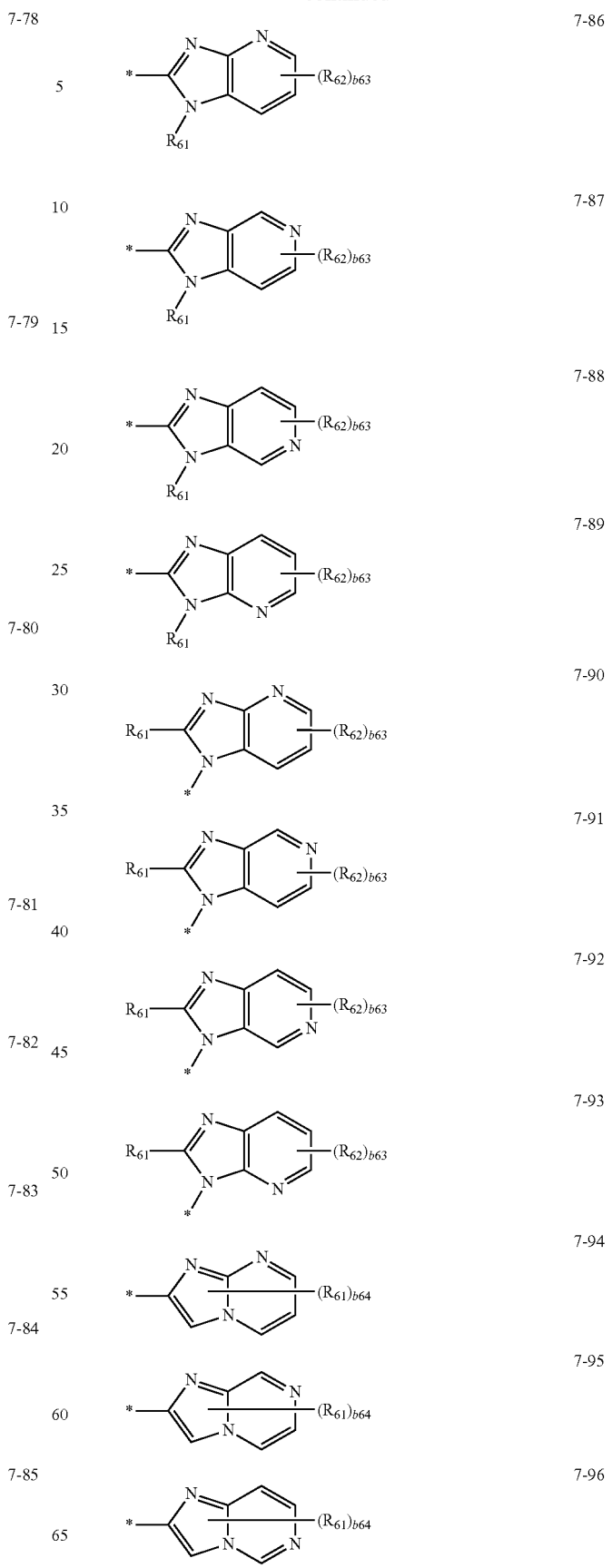

-continued

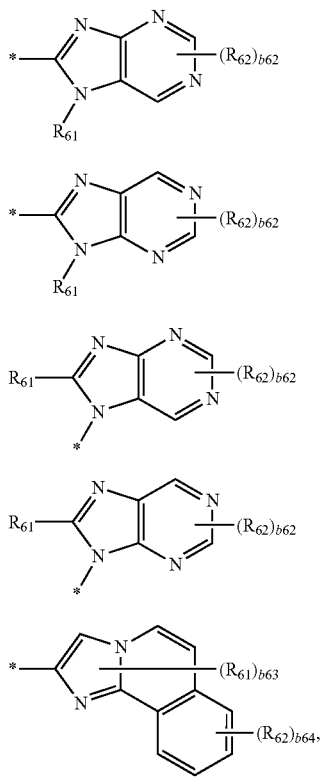

7-97

7-98

7-99

7-100

7-101 wherein, in Formulae 7-4 to 7-101,
$R_{61}$ to $R_{63}$ are each independently selected from hydrogen, deuterium, a $C_1$-$C_{20}$ alkyl group, a phenyl group, a biphenyl group, a terphenyl group, a naphthyl group, a fluorenyl group, a carbazolyl group, a pyridinyl group, and —Si($Q_{31}$)($Q_{32}$)($Q_{33}$),
wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group,
b62 is an integer selected from 1 and 2,
b63 is an integer selected from 1 to 3,
b64 is an integer selected from 1 to 4,
b65 is an integer selected from 1 to 5,
b66 is an integer selected from 1 to 6, and
* indicates a binding site to an adjacent atom.

7. The organic light-emitting device of claim 1, wherein $Ar_1$ is selected from the group consisting of:
a pyrazinyl group, a pyrimidinyl group, a quinolinyl group, an isoquinolinyl group, a benzoquinolinyl group, a benzoisoquinolinyl group, a naphthyridinyl group, a benzonaphthyridinyl group, a quinoxalinyl group, a quinazolinyl group, a phenanthridinyl group, a phenanthrolinyl group, a benzophenanthrolinyl group; and
a pyrazinyl group, a pyrimidinyl group, a quinolinyl group, an isoquinolinyl group, a benzoquinolinyl group, a benzoisoquinolinyl group, a naphthyridinyl group, a benzonaphthyridinyl group, a quinoxalinyl group, a quinazolinyl group, a phenanthridinyl group, a phenanthrolinyl group, and a benzophenanthrolinyl group, each substituted with at least one selected from deuterium, a $C_1$-$C_{20}$ alkyl group, a phenyl group, a biphenyl group, a terphenyl group, a naphthyl group, a fluorenyl group, a carbazolyl group, a pyridinyl group, and —Si($Q_{31}$)($Q_{32}$)($Q_{33}$),
wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

8. The organic light-emitting device of claim 1, wherein $Ar_{11}$ and $Ar_{12}$ are each independently selected from the group consisting of:
a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a dibenzofuranyl group, a benzothiophenyl group, a dibenzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, an imidazopyrimidinyl group, a naphthoxanthenyl group, a dibenzosilolyl group, a benzonaphthofuranyl group, a benzopyrenyl group; and
a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a dibenzofuranyl group, a benzothiophenyl group, a dibenzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, an imidazopyrimidinyl group, a naphthoxanthenyl group, a dibenzosilolyl group, a benzonaphthofuranyl group, and a benzopyrenyl group, each substituted win at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spirobifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

9. The organic light-emitting device of claim 1, wherein $Ar_{11}$ and $Ar_{12}$ are each independently selected from groups represented by Formulae 5-1 to 5-23:

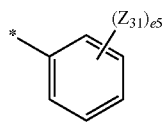
Formula 5-1

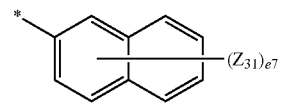
Formula 5-2

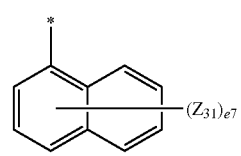
Formula 5-3

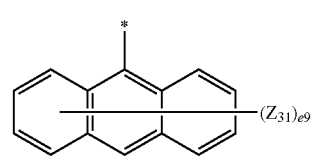
Formula 5-4

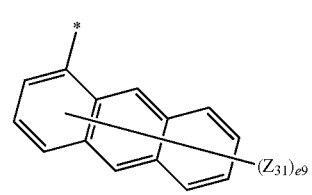
Formula 5-5

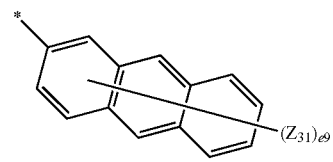
Formula 5-6

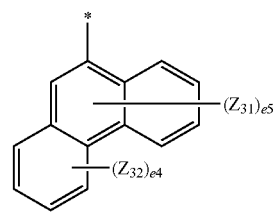
Formula 5-7

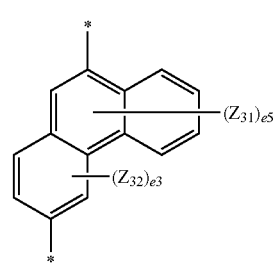
Formula 5-8

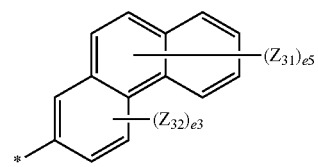
Formula 5-9

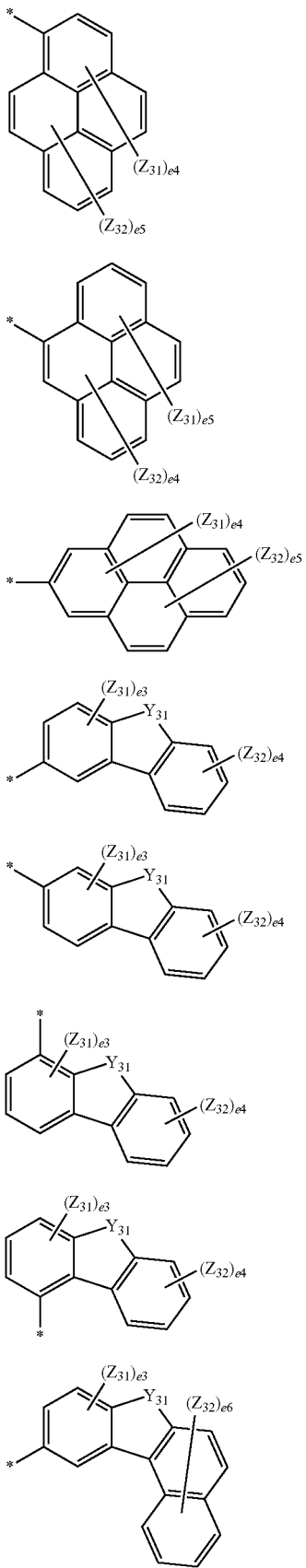
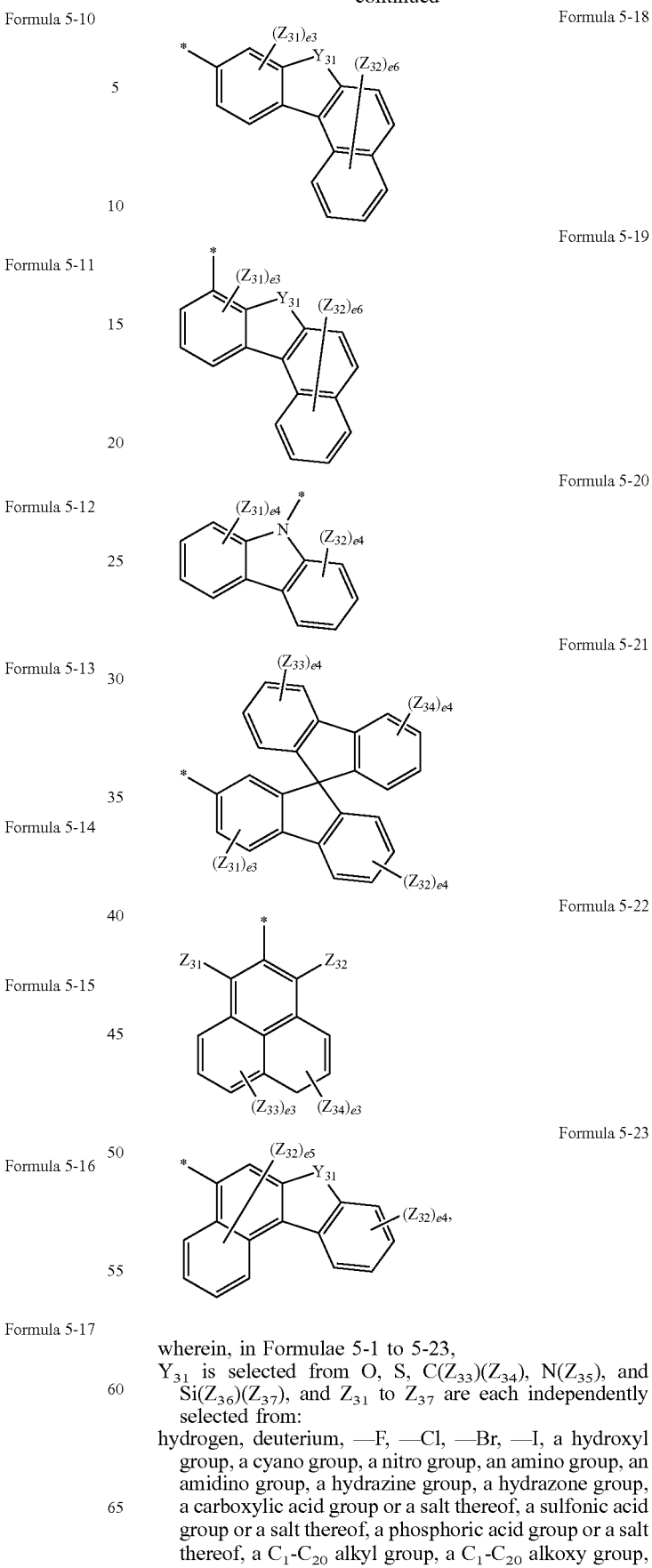

wherein, in Formulae 5-1 to 5-23,
Y$_{31}$ is selected from O, S, C(Z$_{33}$)(Z$_{34}$), N(Z$_{35}$), and Si(Z$_{36}$)(Z$_{37}$), and Z$_{31}$ to Z$_{37}$ are each independently selected from:
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a triazinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group, e3 is an integer selected from 1 to 3,
e4 is an integer selected from 1 to 4,
e5 is an integer selected from 1 to 5,
e6 is an integer selected from 1 to 6,
e7 is an integer selected from 1 to 7,
e8 is an integer selected from 1 to 8,
e9 is an integer selected from 1 to 9, and
* indicates a binding site to an adjacent atom.

10. The organic light-emitting device of claim 1, wherein $Ar_{11}$ and $Ar_{12}$ are each independently selected from groups represented by Formulae 6-1 to 6-54:

Formula 6-1

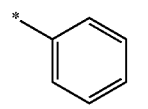

Formula 6-2

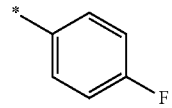

Formula 6-3

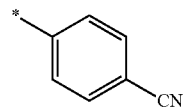

Formula 6-4

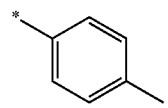

Formula 6-5

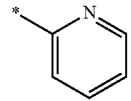

Formula 6-6

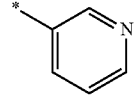

Formula 6-7

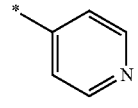

Formula 6-8

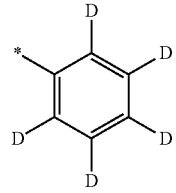

-continued

Formula 6-9

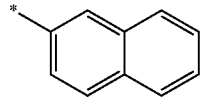

Formula 6-10

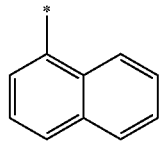

Formula 6-11

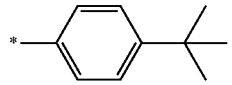

Formula 6-12

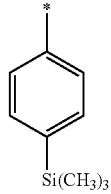

Formula 6-13

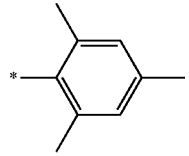

Formula 6-14

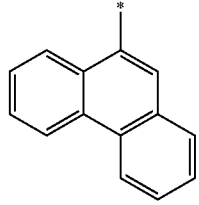

Formula 6-15

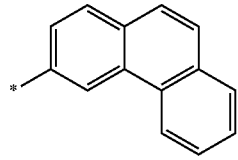

Formula 6-16

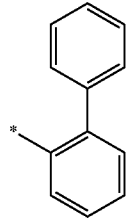

-continued
Formula 6-17
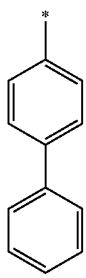
Formula 6-18
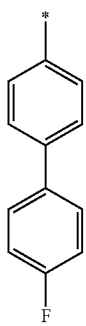
Formula 6-19
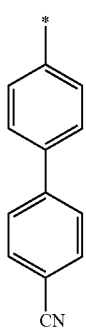
Formula 6-20
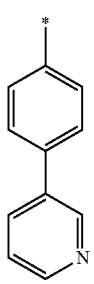
Formula 6-21
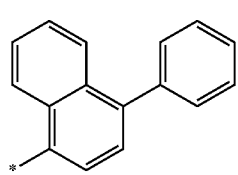
Formula 6-22
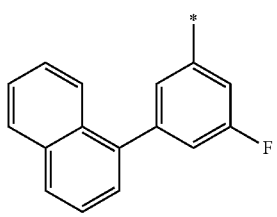
-continued
Formula 6-23
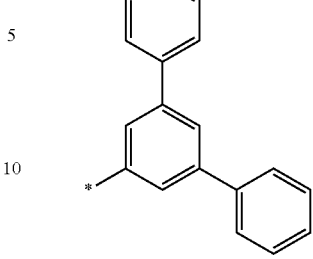
Formula 6-24
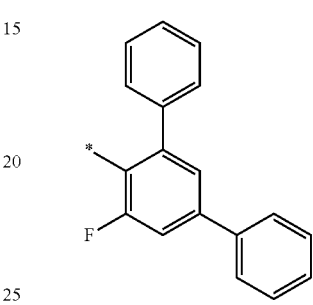
Formula 6-25
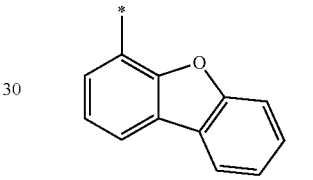
Formula 6-26
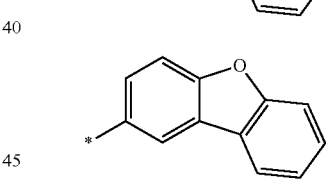
Formula 6-27
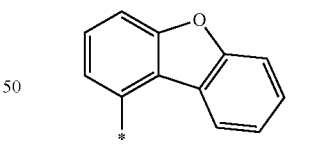
Formula 6-28
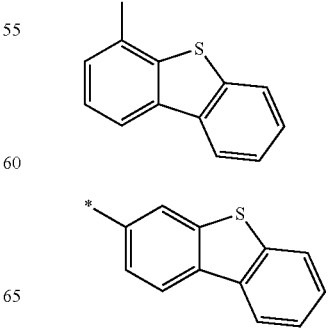
Formula 6-29
Formula 6-30

149
-continued
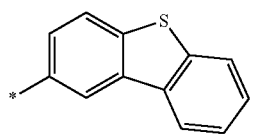
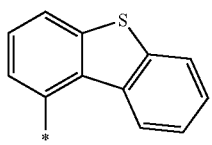
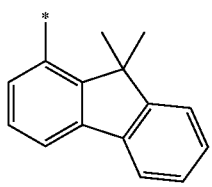
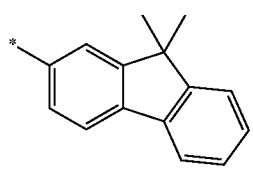
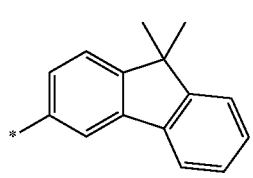
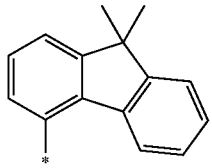
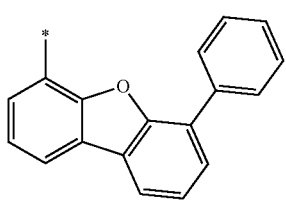
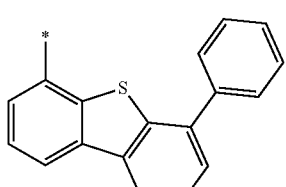
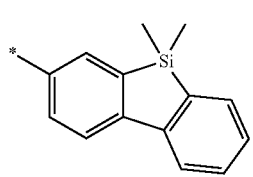
150
-continued
Formula 6-31
Formula 6-32
Formula 6-33
Formula 6-34
Formula 6-35
Formula 6-36
Formula 6-37
Formula 6-38
Formula 6-39
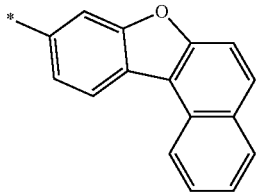
Formula 6-40
Formula 6-41
Formula 6-42
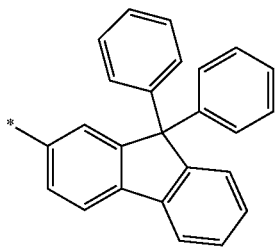
Formula 6-43
Formula 6-44
Formula 6-45

-continued

Formula 6-46
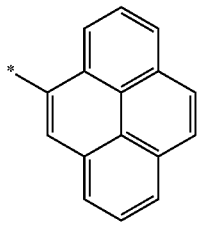

Formula 6-47
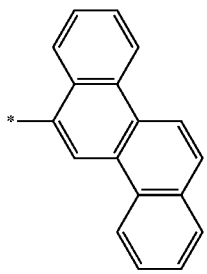

Formula 6-48
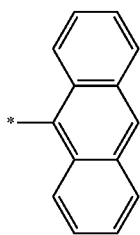

Formula 6-49
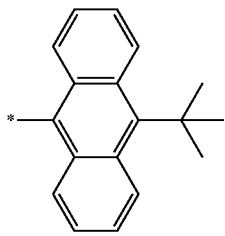

Formula 6-50
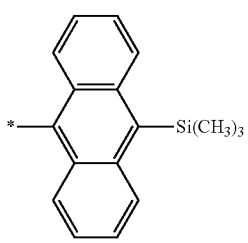

Formula 6-51
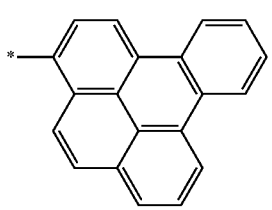

-continued

Formula 6-52
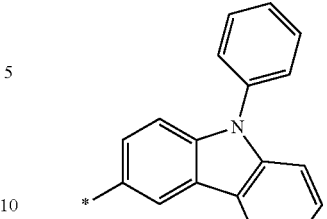

Formula 6-53
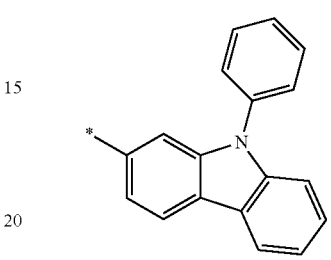

Formula 6-54
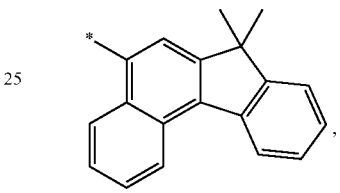

wherein, in Formulae 6-1 to 6-54, * indicates a binding site to an adjacent atom.

11. The organic light-emitting device of claim 1, wherein $R_1$ is selected from:
   hydrogen, deuterium, a $C_1$-$C_{20}$ alkyl group; and
   a $C_1$-$C_{20}$ alkyl group substituted with at least one selected from deuterium, —F, —Cl, —Br, —I, a hydroxyl group, a cyano group, a nitro group, a carboxylic acid group or a salt thereof, a sulfonic acid group or a salt thereof, and a phosphoric acid group or a salt thereof.

12. The organic light-emitting device of claim 1, wherein $R_2$ to $R_9$ and $R_{11}$ to $R_{18}$ are each independently selected from the group consisting of:
   hydrogen, deuterium, —F, —Cl, —Br, —I a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group;
   a $C_1$-$C_{10}$ alkyl group and a $C_1$-$C_{10}$ alkoxy group, each substituted with at least one selected from deuterium, —F, —Cl, —Br —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and —Si($Q_{31}$)($Q_{32}$)($Q_{33}$); and
   —Si($Q_1$)($Q_2$)($Q_3$),
   wherein $Q_1$ to $Q_3$ and $Q_{31}$ to $Q_{33}$ are each independently selected from a $C_1$-$C_{10}$ alkyl group, a phenyl group, a biphenyl group, a terphenyl group, and a naphthyl group.

13. The organic light-emitting device of claim 1, wherein the first compound is represented by Formula 1A, and the second compound is represented by one selected from Formulae 2A to 2C:

Formula 1A

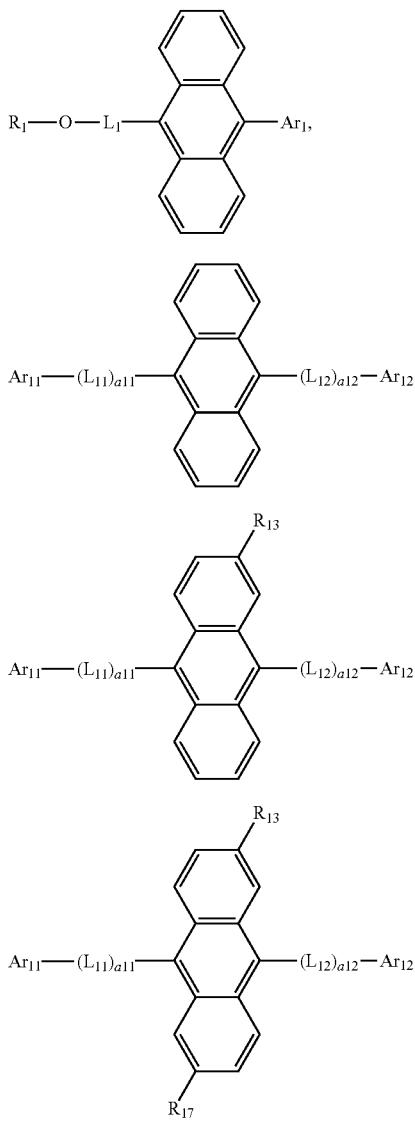

Formula 2A

Formula 2B

Formula 2C wherein, in Formulae 1A, 2A, 2B, and 2C, $L_1$, $L_{11}$, $L_{12}$, a11, a12, $Ar_1$, $Ar_{11}$, $Ar_{12}$, $R_1$, $R_{13}$, and $R_{17}$ are each the same as described herein in connection with Formulae 1 and 2, provided that $R_{13}$ and $R_{17}$ are both not hydrogen.

14. The organic light-emitting device of claim 1, wherein the first compound is represented by Formula 1A-1, and the second compound is represented by one selected from Formulae 2A to 2C:

Formula 1A-1

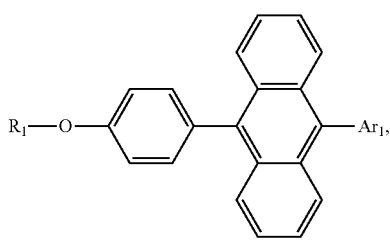

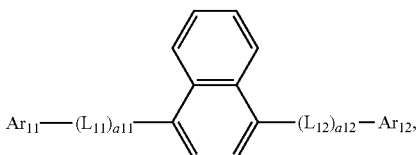

Formula 2A

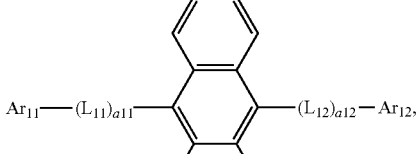

Formula 2B

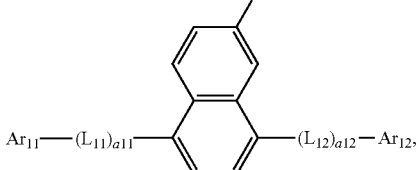

Formula 2C wherein, in Formulae 1A-1, 2A, 2B, and 2C, $L_{11}$, $L_{12}$, a11, a12, $Ar_1$, $Ar_{11}$, $Ar_{12}$, $R_1$, $R_{13}$, and $R_{17}$ are each the same as described herein in connection with Formulae 1 and 2, provided that $R_{13}$ and $R_{17}$ are both not hydrogen.

15. The organic light-emitting device of claim 13, wherein $L_1$, $L_{11}$, and $L_{12}$ are each independently selected from the group consisting of:

a phenylene group, a naphthylene group, a fluorenylene group, a benzofluorenylene group, a phenanthrenylene group, an anthracenylene group, a pyrenylene group, a chrysenylene group; and a phenylene group, a naphthylene group, a fluorenylene group, a benzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$), a11 and a12 are each independently selected from 0 and 1, $Ar_1$ is selected from the group consisting of:

a pyrazinyl group, a pyrimidinyl group, a quinolinyl group, an isoquinolinyl group, a benzoquinolinyl group, a benzoisoquinolinyl group, a naphthyridinyl group, a benzonaphthyridinyl group, a quinoxalinyl group, a quinazolinyl group, a phenanthridinyl group, a phenanthrolinyl group, a benzophenanthrolinyl group; and a pyrazinyl group, a pyrimidinyl group, a quinolinyl group, an isoquinolinyl group, a benzoquinolinyl group, a benzoisoquinolinyl group, a naphthyridinyl group, a benzonaphthyridinyl group, a quinoxalinyl group, a quinazolinyl group, a phenanthridinyl group, a phenanthrolinyl group, and a benzophenanthrolinyl group, each substituted with at least one selected from deuterium, a $C_1$-$C_{20}$ alkyl group, a phenyl group, a biphenyl group, a terphenyl group, a naphthyl group, a fluorenyl group, a carbazolyl group, a pyridinyl group, and —Si($Q_{31}$)($Q_{32}$)($Q_{33}$), $Ar_{11}$ and $Ar_{12}$ are each independently selected from the group consisting of:

a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a naphthacenyl group, a carbazolyl group, a benzofuranyl group, a dibenzofuranyl group, a benzothiophenyl group, a dibenzothiophenyl group; and a phenyl group, a biphenyl group, a terphenyl group, a naphthyl group, a fluorenyl group, a spirobifluorenyl group, a benzofluorenyl group, a dibenzofluorenyl group, a phenanthrenyl group, an anthracenyl group, a pyrenyl group, a chrysenyl group, a naphthacenyl group, a carbazolyl group, a benzofuranyl group, a dibenzofuranyl group, a benzothiophenyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$), $R_1$ is selected from the group consisting of:

hydrogen, deuterium, a $C_1$-$C_{20}$ alkyl group; and a $C_1$-$C_{20}$ alkyl group substituted with at least one selected from deuterium, —F, —Cl, —Br, —I, a hydroxyl group, a cyano group, a nitro group, a carboxylic acid group or a salt thereof, a sulfonic acid group or a salt thereof, and a phosphoric acid group or a salt thereof, and $R_{13}$ to $R_{17}$ are each independently selected from the group consisting of:

deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group;

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and —Si($Q_{31}$)($Q_{32}$)($Q_{33}$);, and —Si($Q_1$)($Q_2$)($Q_3$), wherein $Q_1$ to $Q_3$ and $Q_{31}$ to $Q_{33}$ are each independently selected from a methyl group, an ethyl group, an n-propyl group, an iso-propyl group, an n-butyl group, an iso-butyl group, a sec-butyl group, a tert-butyl group, a phenyl group, a biphenyl group, a terphenyl group, a naphthyl group, and a fluorenyl group.

16. The organic light-emitting device of claim 1, wherein the first compound is represented by one selected from Compounds 1-1 to 1-59, and the second compound is represented by one selected from Compounds 2-1 to 2-81:

1-1
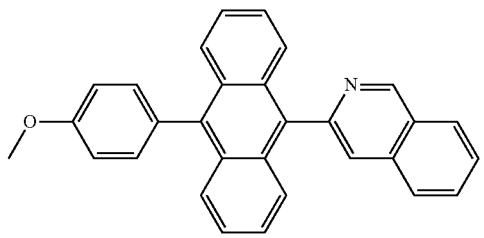

1-2
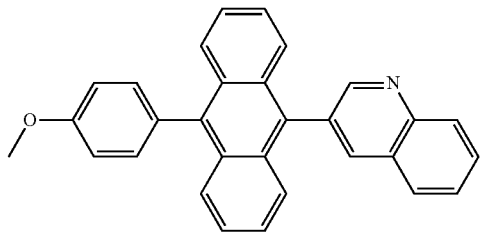 [SMILES: COc1ccc(-c2c3ccccc3c(-c3cnc4ccccc4c3)c3ccccc23)cc1]

1-3
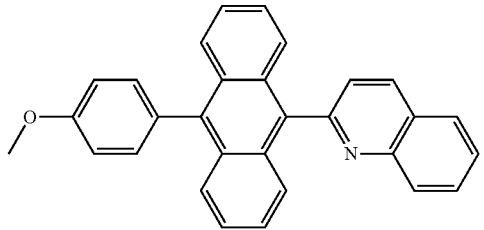

1-4
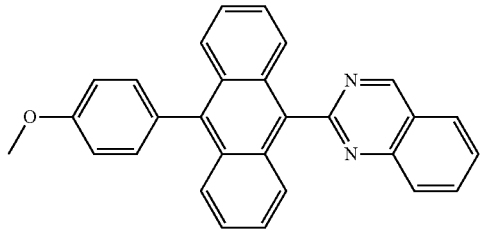

1-5
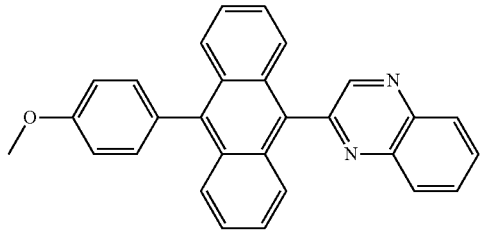

1-6
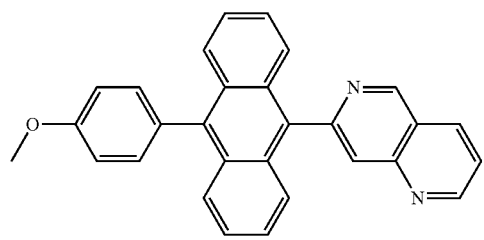 [SMILES: COc1ccc(-c2c3ccccc3c(-c3ccc4ccccc4n3)c3ccccc23)cc1]
1-7
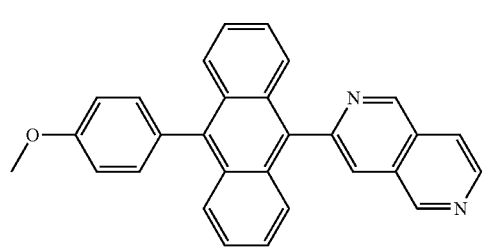
1-8
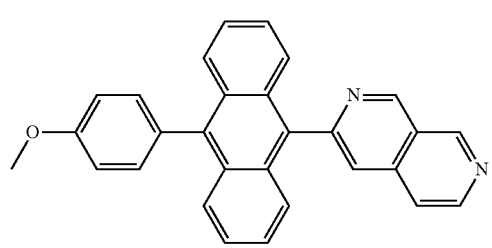
1-9
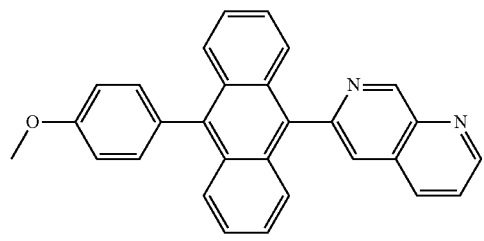
1-10
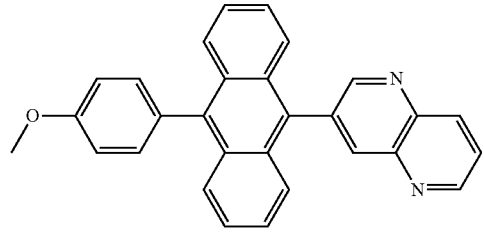
1-11
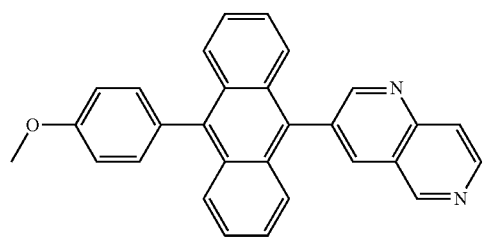
1-12
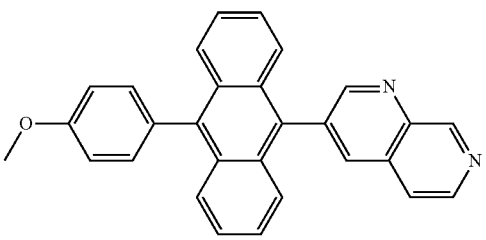
1-13
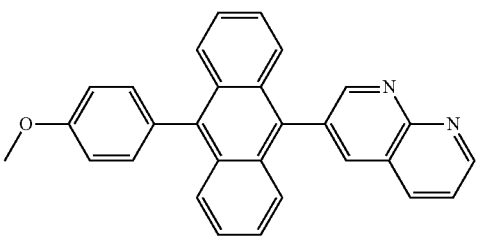
1-14
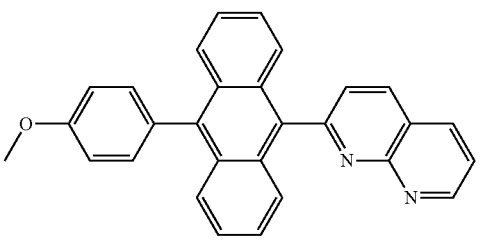
1-15
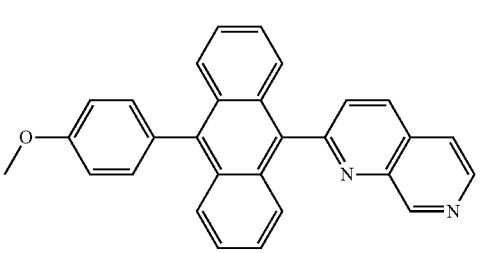
1-16
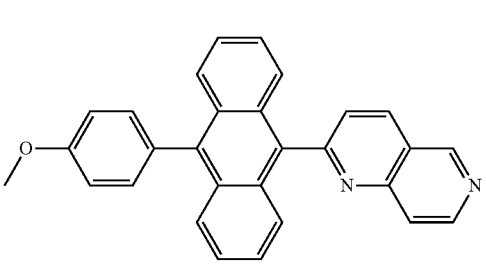
1-17
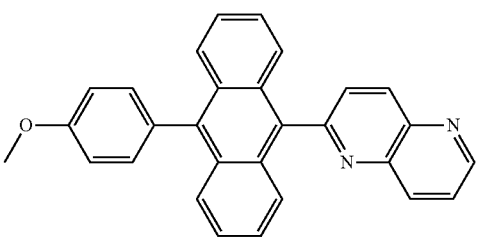

-continued
1-18
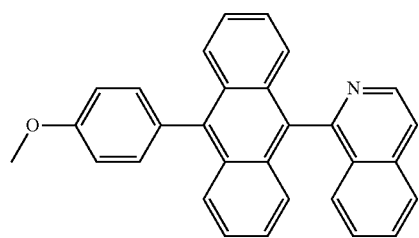
1-19
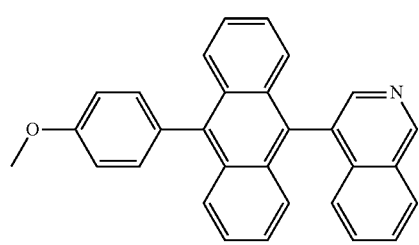
1-20
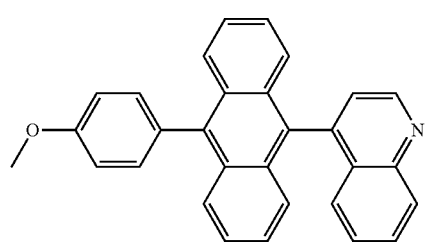
1-21
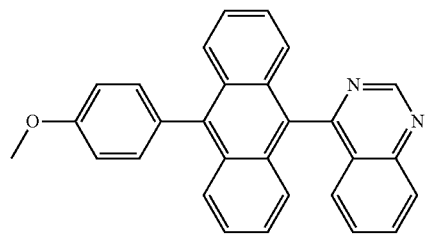
1-22
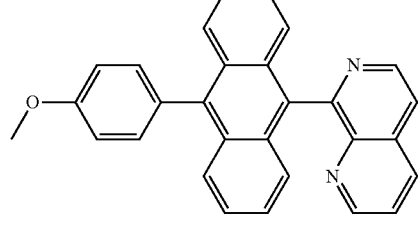
1-23
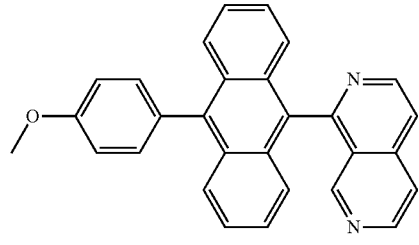
-continued
1-24
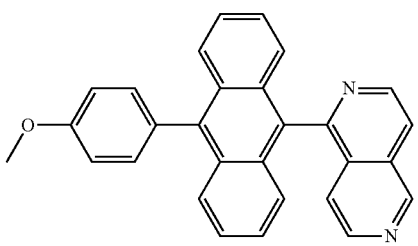
1-25
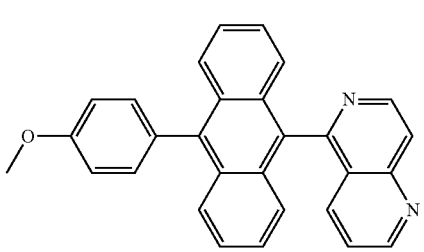
1-26
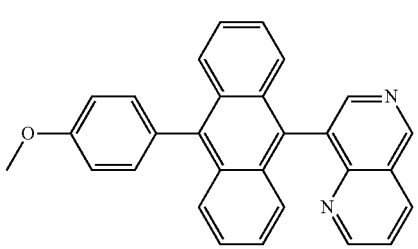
1-27
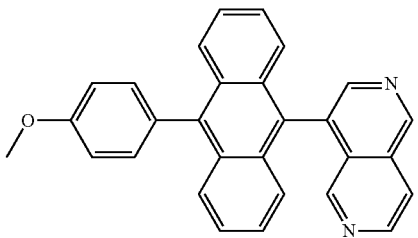
1-28
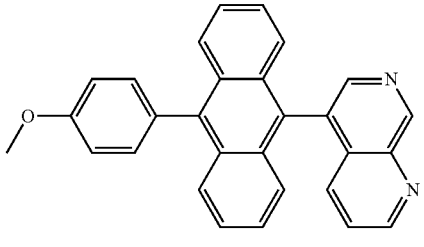
1-29
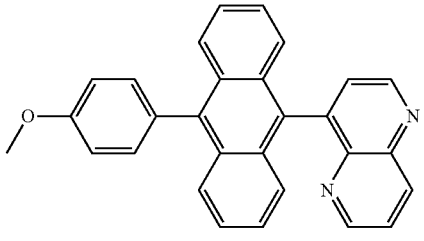

1-30
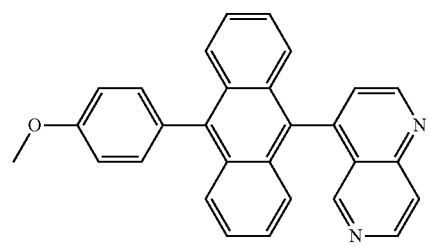
1-31
1-32
1-33
1-34
1-35
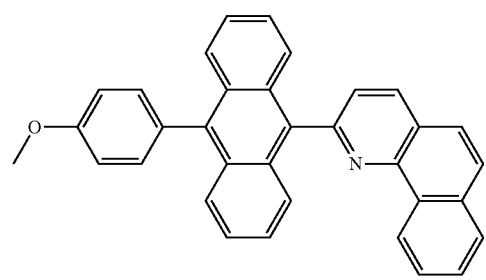
1-36
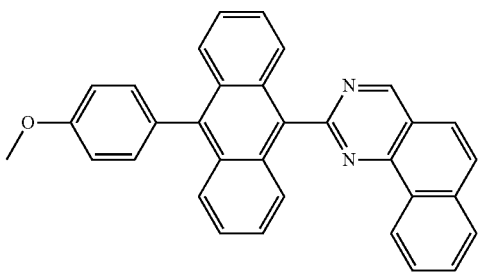
1-37
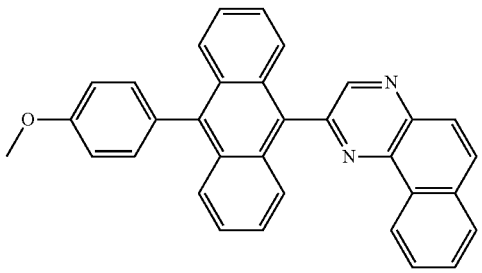
1-38
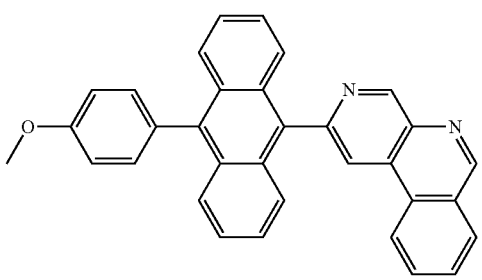
1-39
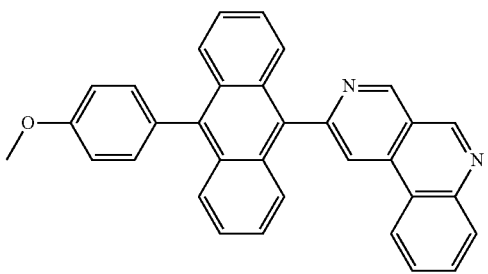
1-40
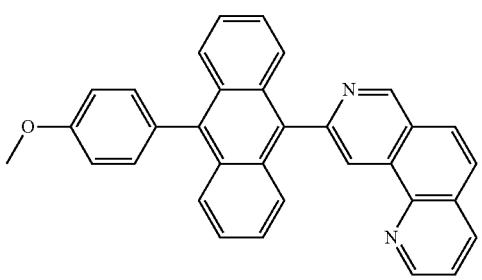

1-41
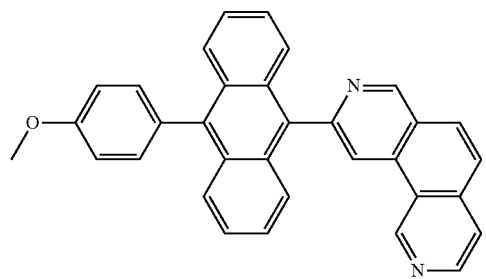
1-42
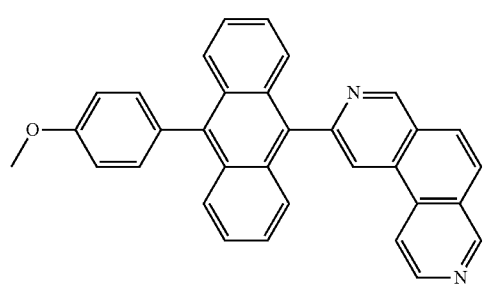
1-43
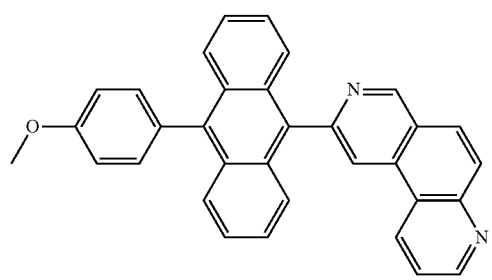
1-44
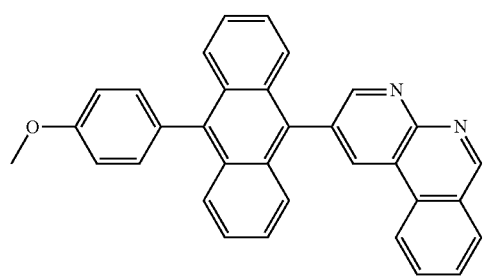
1-45
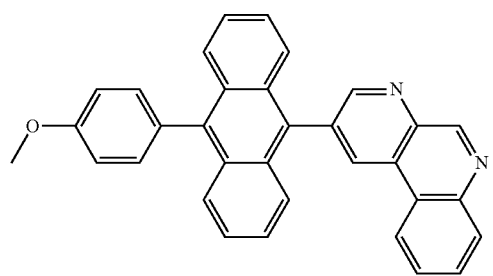
1-46
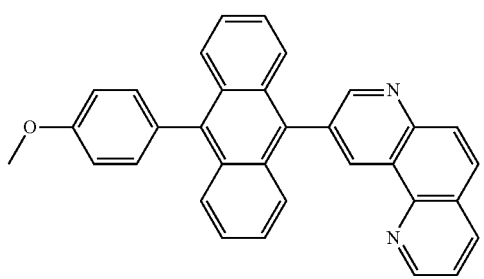
1-47
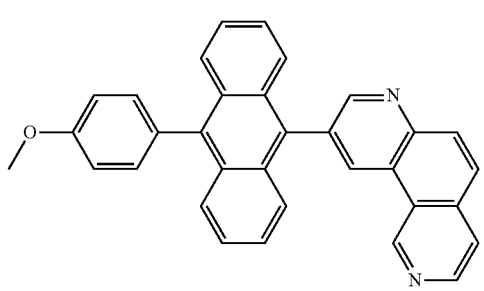
1-48
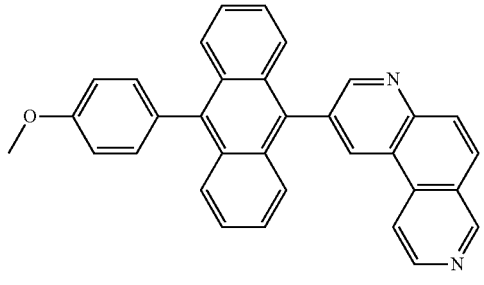
1-49
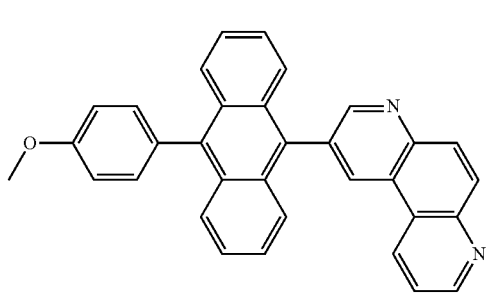
1-50
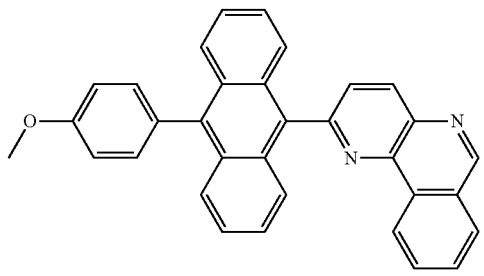

1-51
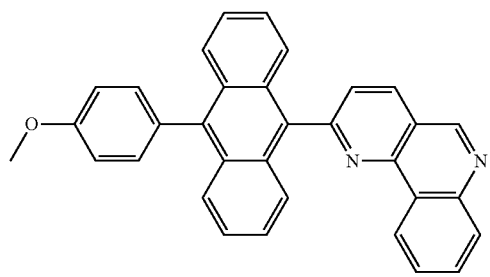
1-52
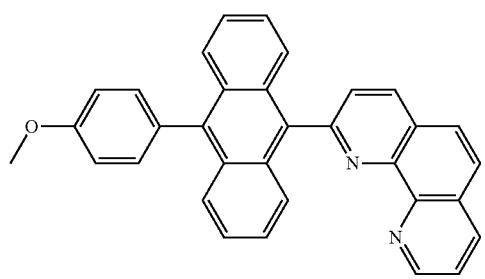 [SMILES: COc1ccc(-c2c3ccccc3c(-c3ccc4ccc5cccnc5c4n3)c3ccccc23)cc1]
1-53
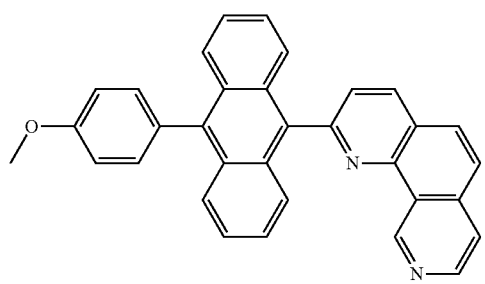
1-54
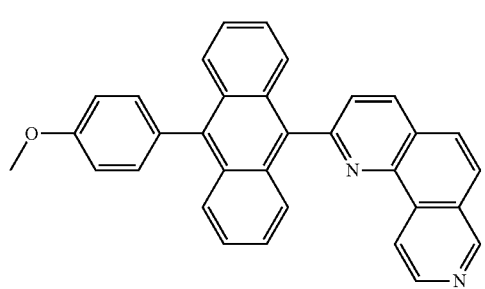
1-55
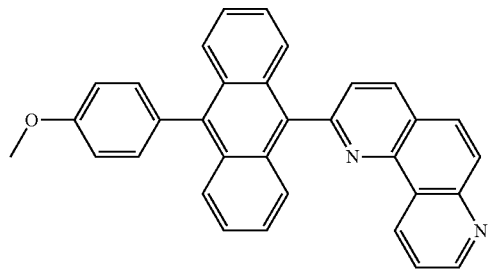
1-56
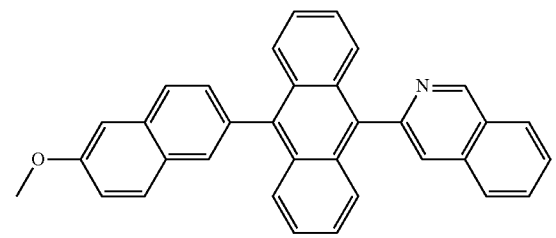
1-57
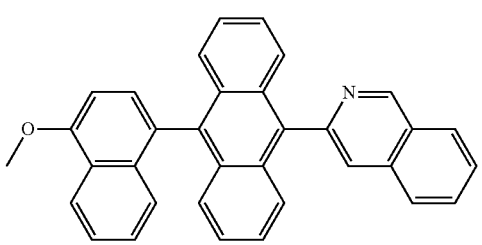
1-58
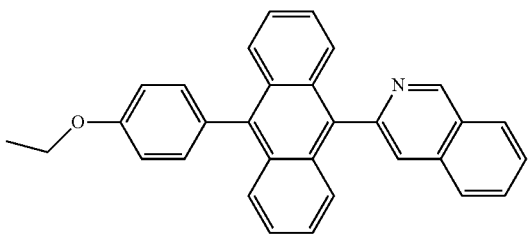
1-59
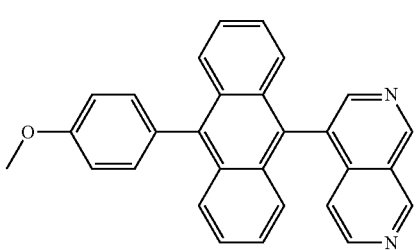
2-1
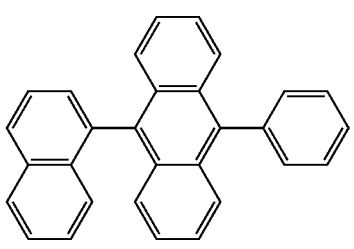
2-2
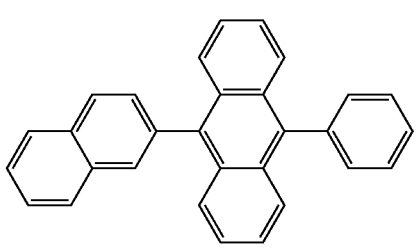

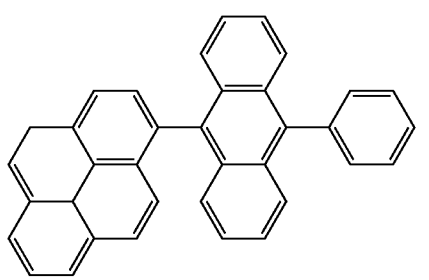
2-3
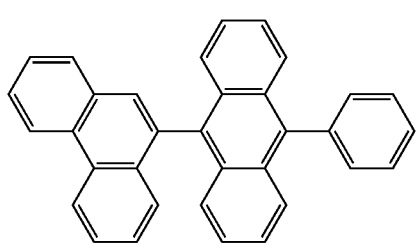
2-4
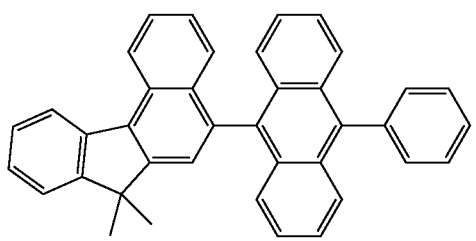
2-5
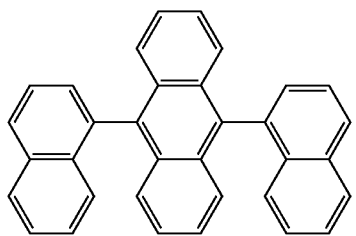
2-6
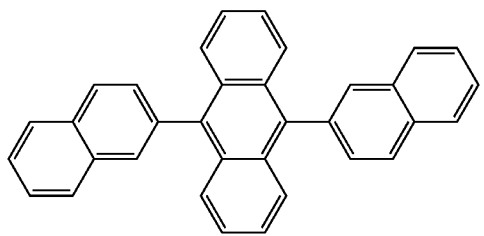 [SMILES: c1ccc2cc(-c3c4ccccc4c(-c4ccc5ccccc5c4)c4ccccc34)ccc2c1]
2-7
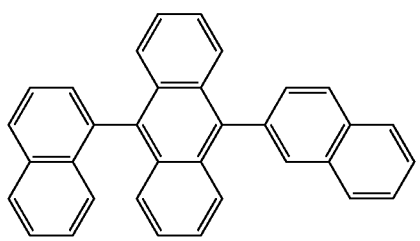
2-8
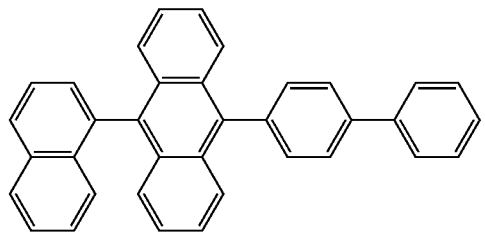
2-9
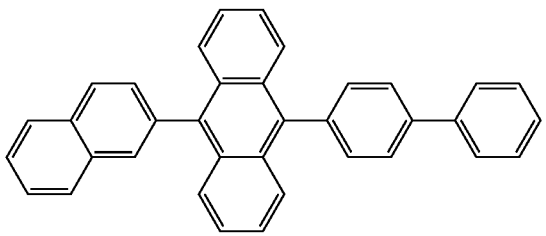
2-10
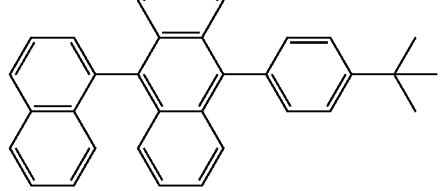
2-11
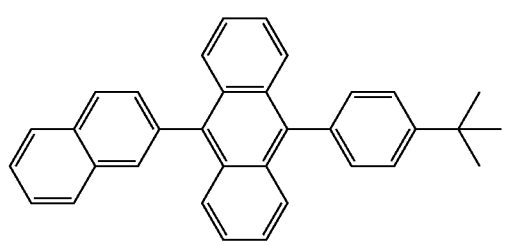
2-12
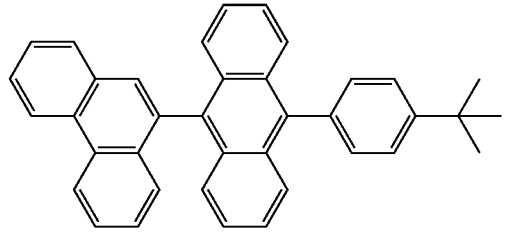
2-13
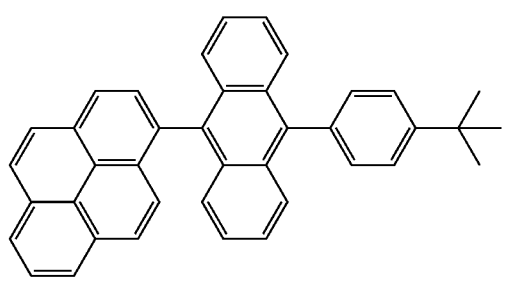
2-14

2-15 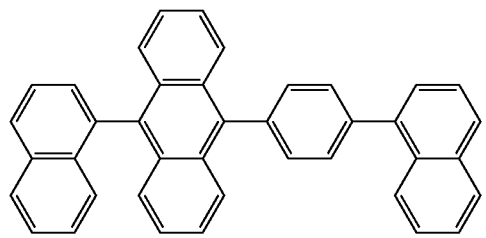
2-16 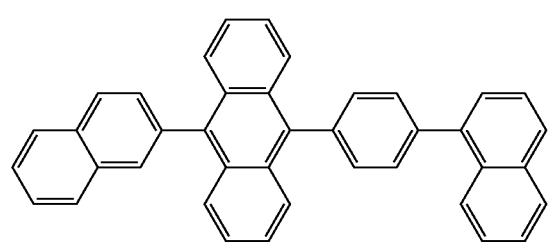
2-17 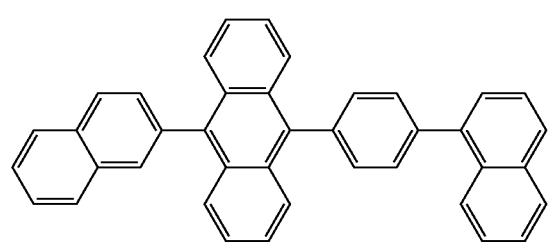
2-18 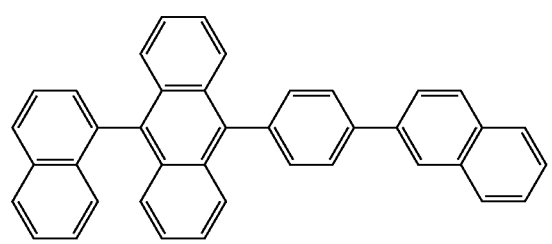
2-19 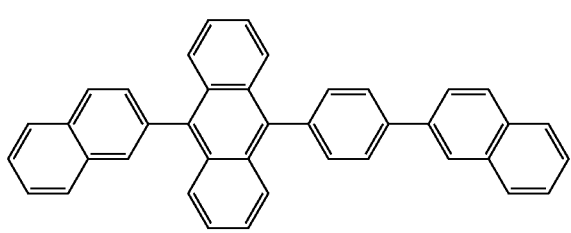
2-20 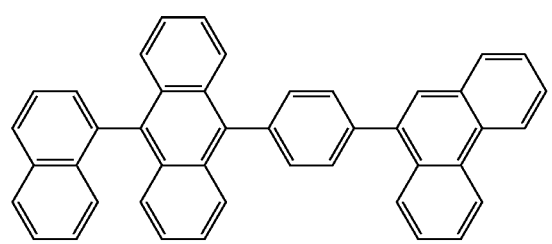
2-21 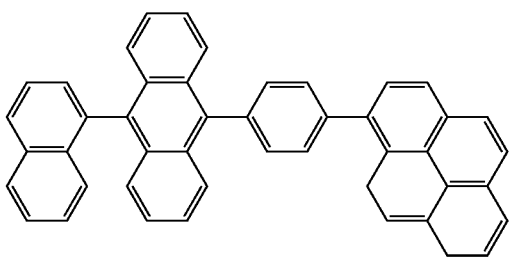
2-22 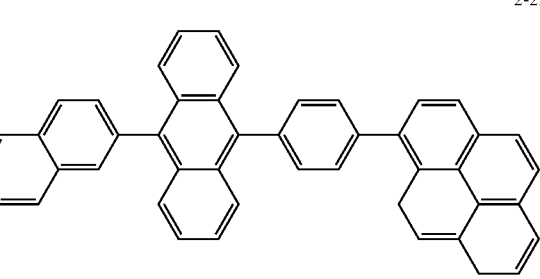
2-23 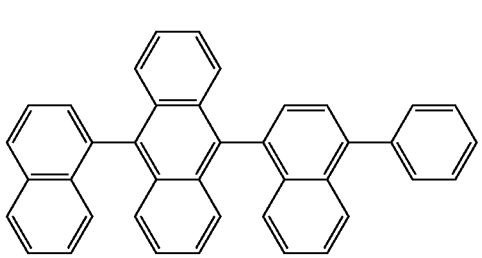
2-24 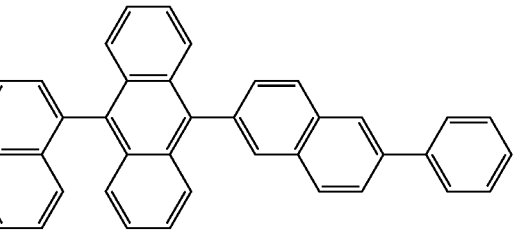
2-25 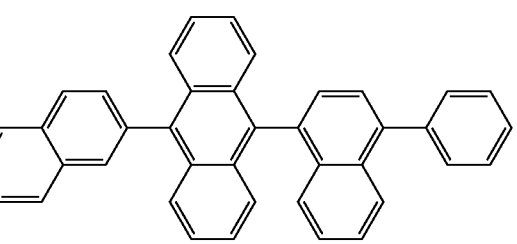
2-26 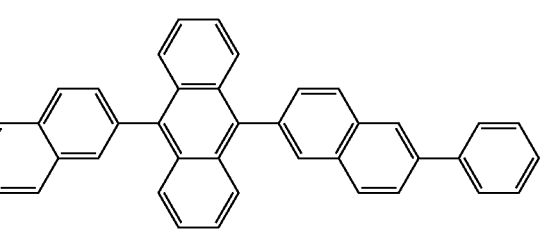

2-27
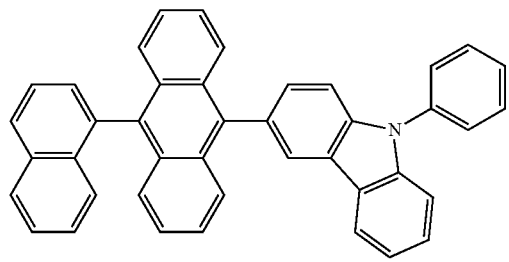
2-33
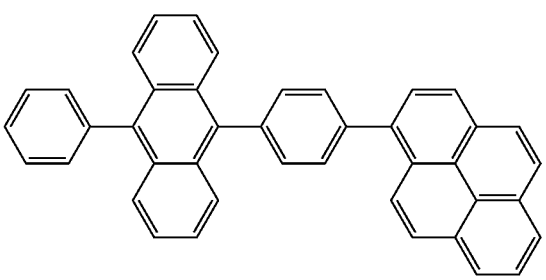
2-28
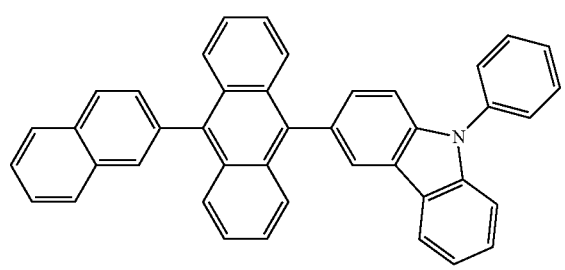
2-34
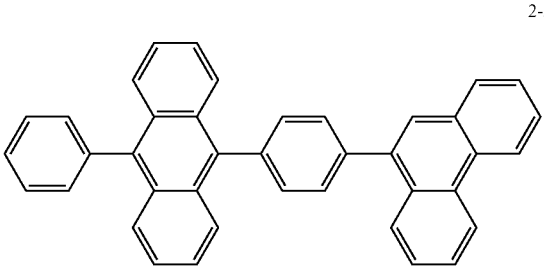
2-29
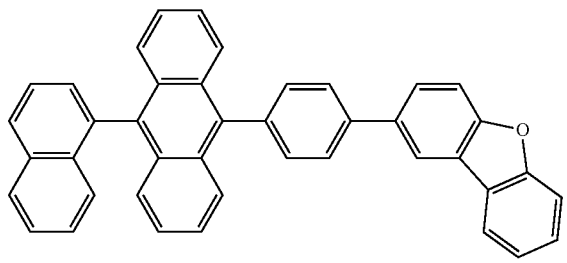
2-35
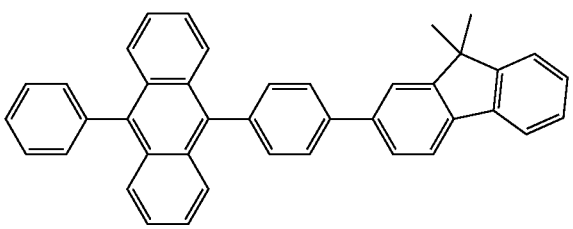
2-30
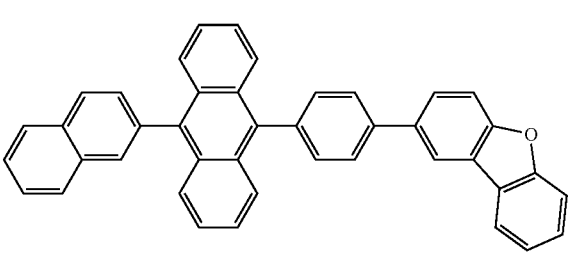
2-36
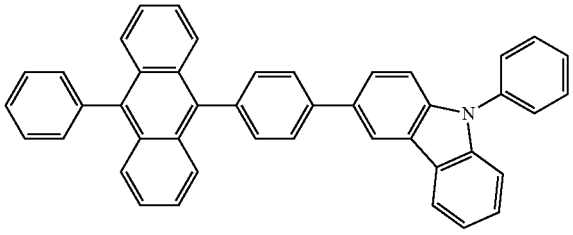
2-31
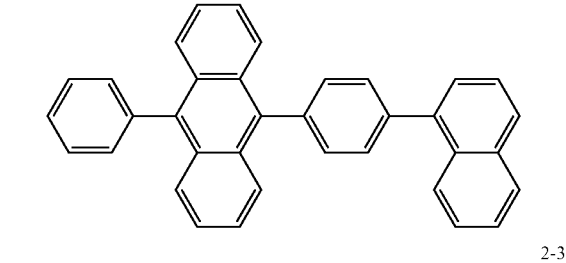
2-37
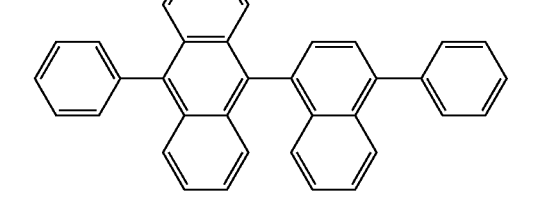
2-32
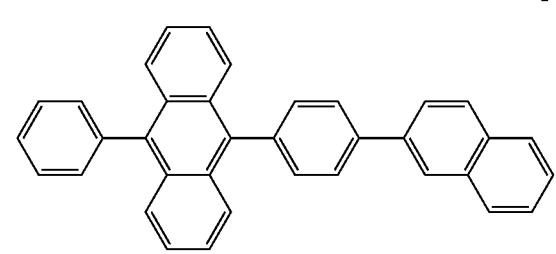
2-38
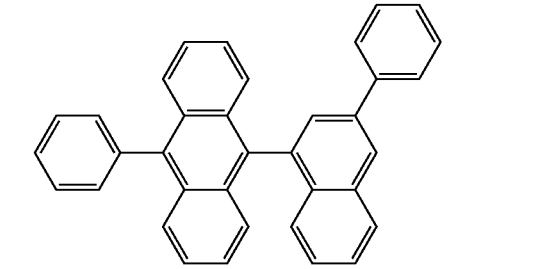

2-39
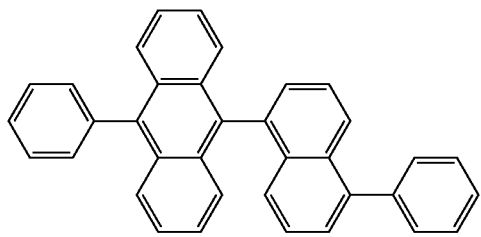
2-40
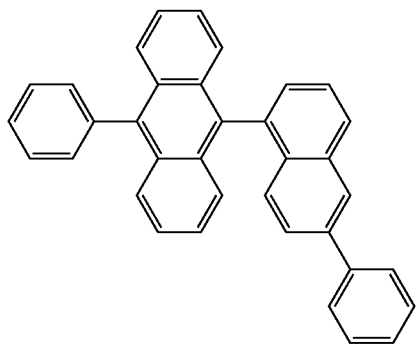
2-41
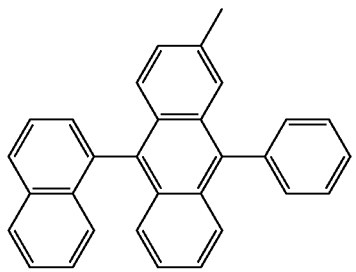
2-42
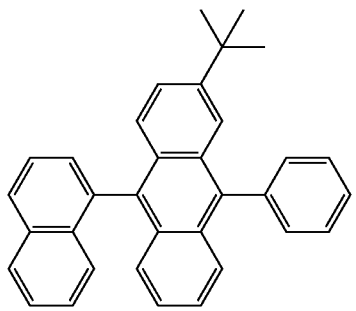
2-43
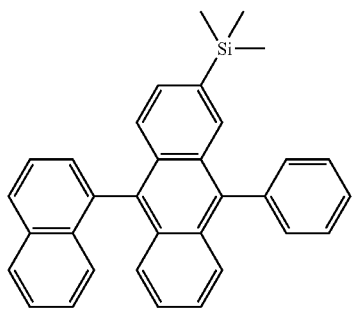
2-44
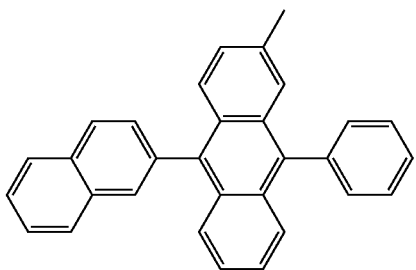
2-45
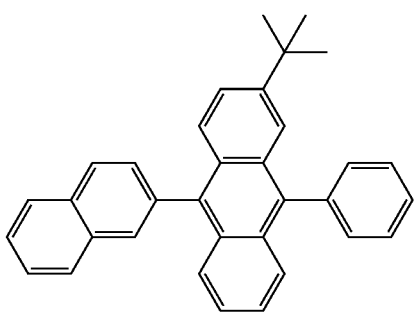
2-46
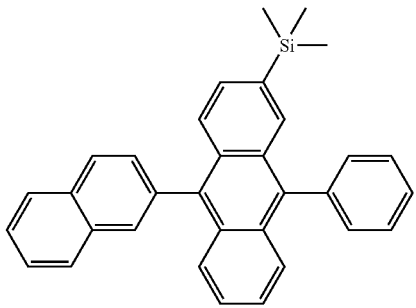
2-47
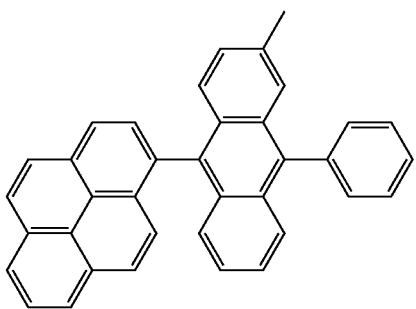
2-48
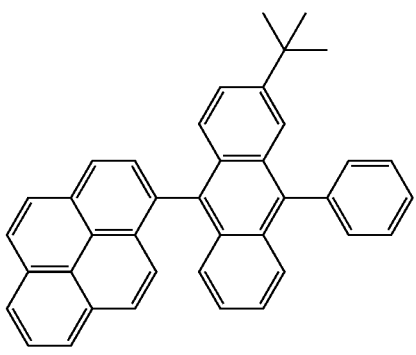

2-49 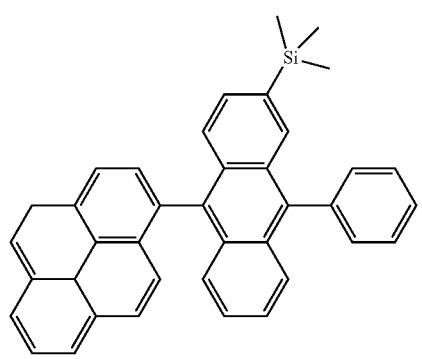
2-50 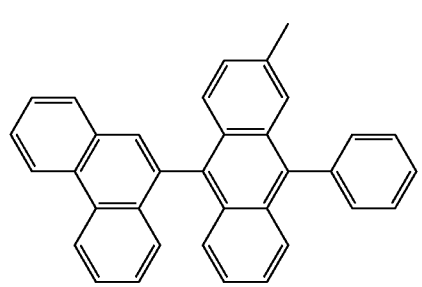
2-51 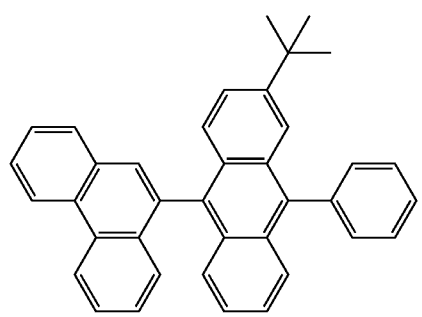
2-52 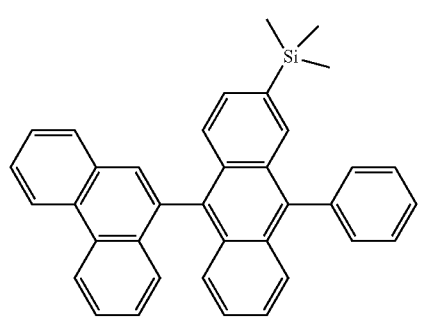
2-53 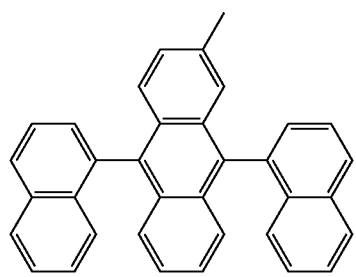
2-54 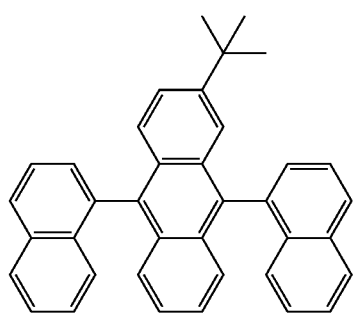
2-55 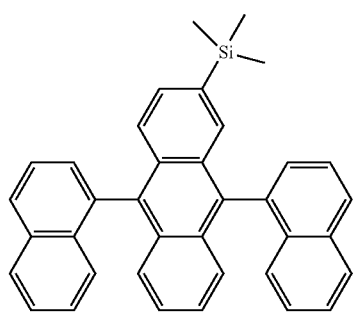
2-56 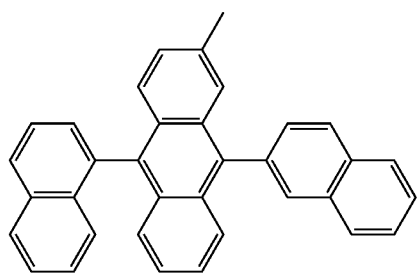
2-57 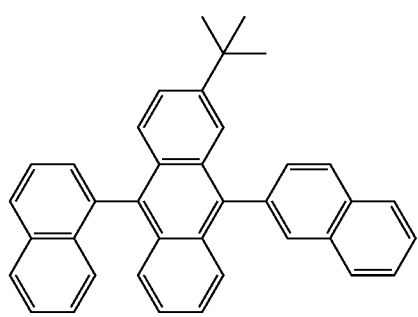
2-58 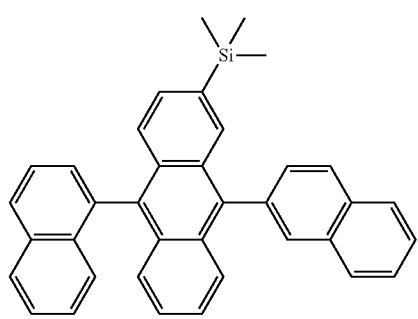

2-59
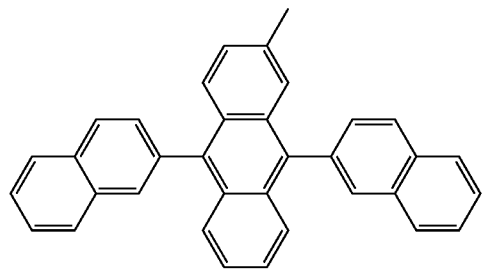
2-60
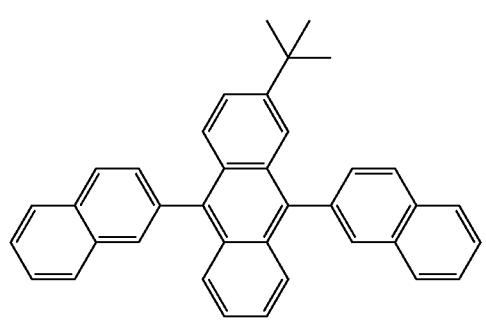
2-61
2-62
2-63
2-64
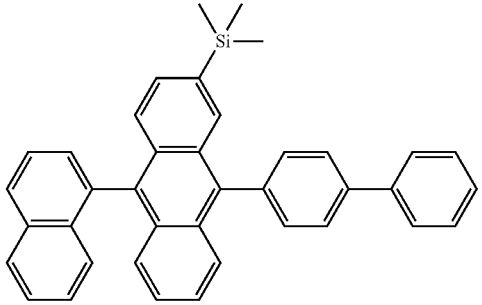
2-65
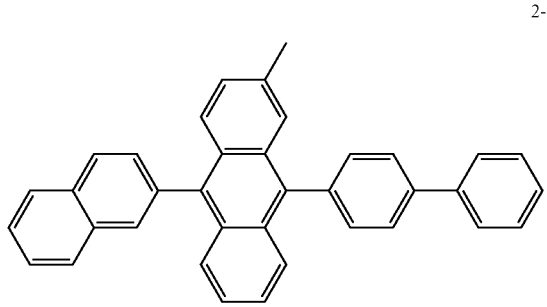
2-66
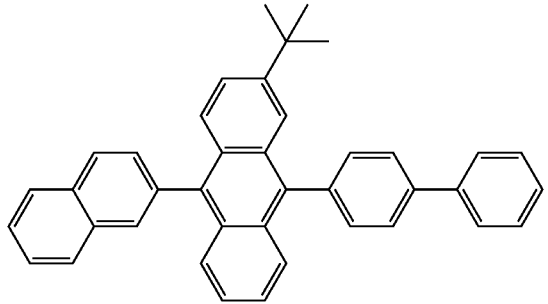
2-67
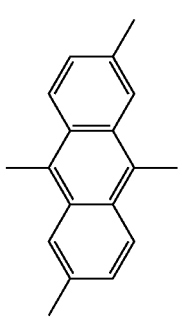
2-68
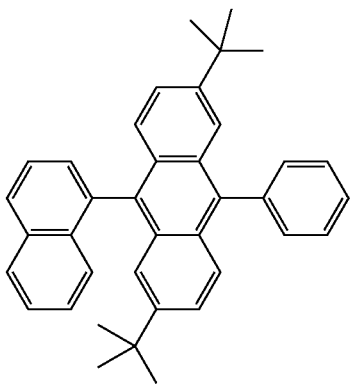

-continued
2-69
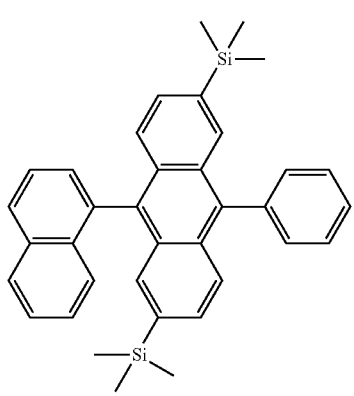
2-70
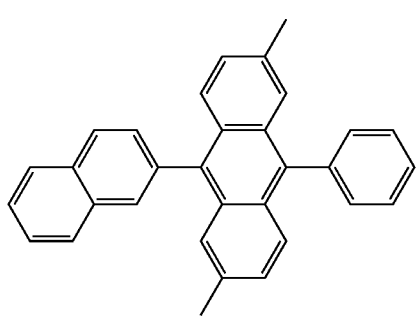
2-71
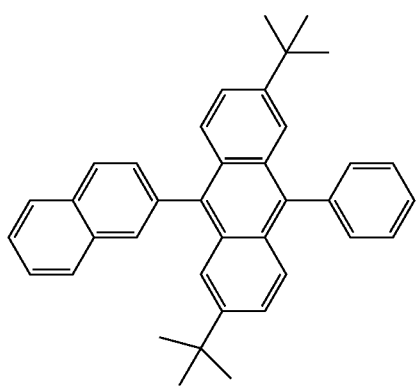
2-72
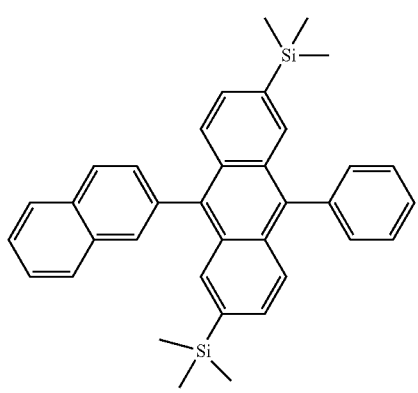
-continued
2-73
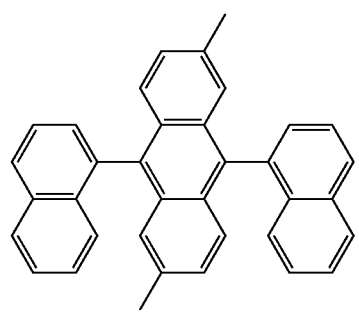
2-74
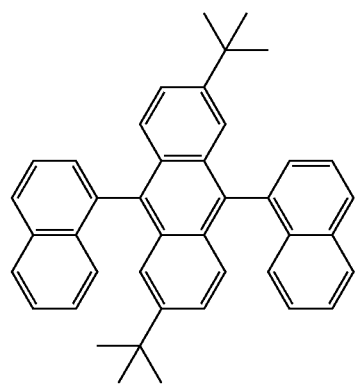
2-75
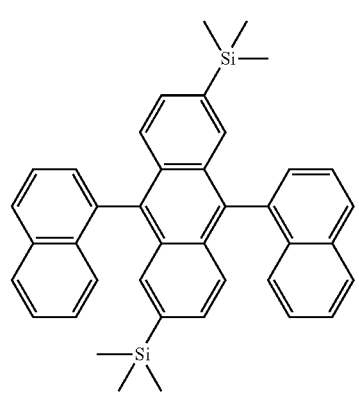
2-76
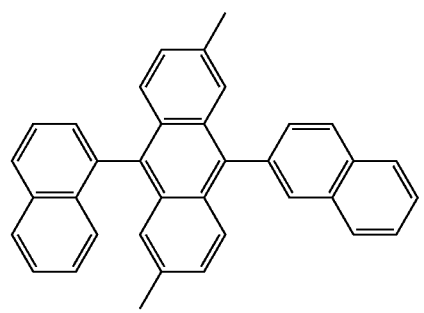

2-77

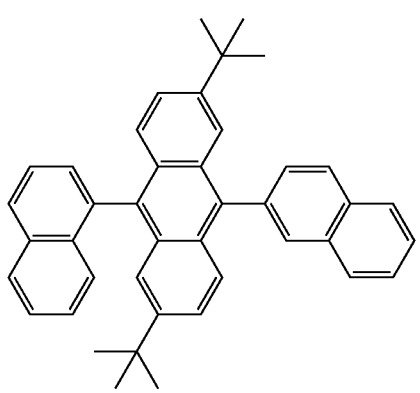

2-78

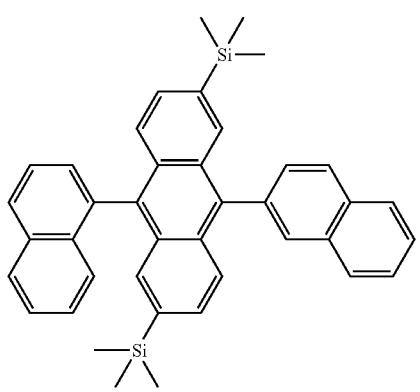

2-79

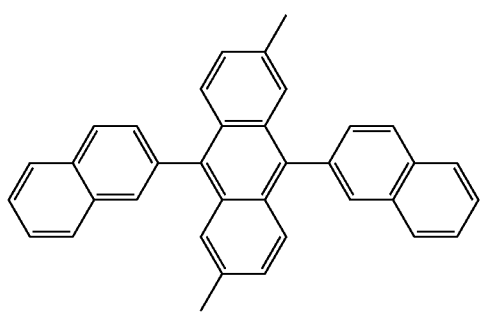

2-80

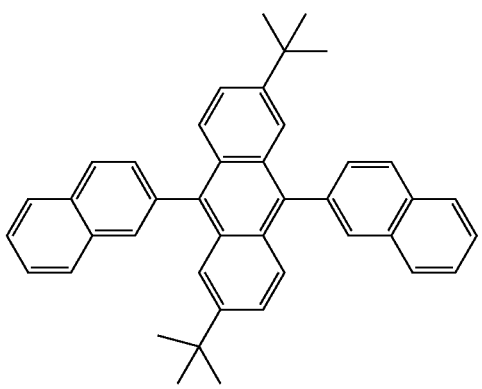

2-81

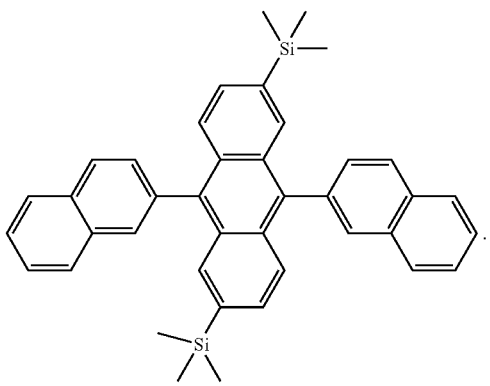

17. The organic light-emitting device of claim 1, wherein:
the first electrode is an anode,
the second electrode is a cathode,
the organic layer comprises a hole transport region between the first electrode and the emission layer and an electron transport region between the emission layer and the second electrode,
the hole transport region comprises at least one selected from a hole injection layer, a hole transport layer, a buffer layer, and an electron blocking layer, and
the electron transport region comprises at least one selected from a hole blocking layer, an electron transport layer, and an electron injection layer.

18. The organic light-emitting device of claim 1, wherein the host is greater in amount than the dopant.

19. The organic light-emitting device of claim 17, wherein a thickness of the emission layer is about 1 nm to about 400 nm.

* * * * *